United States Patent
Ozawa et al.

(10) Patent No.: US 6,635,011 B1
(45) Date of Patent: Oct. 21, 2003

(54) ELECTRONIC ENDOSCOPE SYSTEM

(75) Inventors: Ryo Ozawa, Tokyo (JP); Hideo Sugimoto, Tokyo (JP); Takayuki Enomoto, Saitama (JP)

(73) Assignee: Pentax Corporation, Tokyo (JP)

( * ) Notice: Subject to any disclaimer, the term of this patent is extended or adjusted under 35 U.S.C. 154(b) by 194 days.

(21) Appl. No.: 09/758,161

(22) Filed: Jan. 12, 2001

(30) Foreign Application Priority Data

Jan. 14, 2000 (JP) ..................................... P2000-005674
Aug. 10, 2000 (JP) ..................................... P2000-242554

(51) Int. Cl.⁷ .............................................. A61B 1/00
(52) U.S. Cl. ........................ 600/178; 600/109; 600/126; 600/160; 600/476
(58) Field of Search ................ 600/109, 126, 600/160, 178, 182, 476, 478

(56) References Cited

U.S. PATENT DOCUMENTS 5,749,830 A * 5/1998 Kaneko et al. ............. 600/160
5,891,016 A 4/1999 Utsui et al.
6,099,466 A * 8/2000 Sano et al. ................. 600/160

* cited by examiner

Primary Examiner—Teresa Walberg
Assistant Examiner—Shawntina T. Fuqua
(74) Attorney, Agent, or Firm—Greenblum & Bernstein, P.L.C.

(57) ABSTRACT

In an electronic endoscope system, a scope has an image sensor provided at a distal end thereof to generate image-pixel signals. A proximal end of the scope is connected to an image-signal processing unit, in which the image-pixel signals are processed to produce a video signal. A light source device is provided in the processing unit. An optical light guide extends through the scope. When the connection is established between the scope and the processing unit, the light guide is optically connected to the light source device. The light source device includes a white light lamp, and an ultraviolet lamp, and a mirror for selectively introducing either the white light or the ultraviolet light into the light guide.

14 Claims, 39 Drawing Sheets

ELECTRONIC ENDOSCOPE SYSTEM

BACKGROUND OF THE INVENTION

1. Field of the Invention

The present invention relates to an electronic endoscope system including an elongate flexible scope having a solid-state image sensor provided at a distal end thereof to generate image-pixel signals, and an image-signal processing unit that produces a video signal on the basis of the image-pixel signals.

2. Description of the Related Art

In such an electronic endoscope system, a CCD (charge-coupled-device) image sensor is usually utilized as the solid-state image sensor, and is associated with an objective lens system provided at the distal end of the flexible scope. Also, a flexible optical guide, formed of a bundle of optical fibers, is extended through the flexible scope, and is associated with a lighting lens system provided at the distal end of the flexible scope.

The image-signal processing unit includes a light source, such as a halogen lamp, a xenon lamp or the like, and when the flexible scope is connected to the image-signal processing unit, the proximal end of the optical light guide is optically connected to the light source. Thus, an object to be sensed by the CCD image sensor is illuminated by light radiating from the distal end of the optical light guide, and is focused as an optical image on a light-receiving surface of the CCD image sensor, by the objective lens system.

The focused optical image is converted into a frame of analog image-pixel signals by the CCD image sensor, and the frame of analog image-pixel signals is read from the CCD image sensor at successively given regular time intervals. The successively-read frames of image-pixel signals are then fed to the image-signal processing unit, in which the frames of image-pixel signals are suitably processed to produce a video signal. The video signal is then fed from the image-signal processing unit to a TV monitor, to reproduce an endoscope-image on the screen of the TV monitor.

Recently, in the electronic endoscope system, a specific wavelength light source may be substituted for the white light source to perform a specific medical examination. For example, an ultraviolet lamp is used as the specific wavelength light source to find cancer tissue from among internal tissue of a person. In particular, when internal tissue of a person is irradiated with UV light, the irradiated tissue generates fluorescence. The intensity of the fluorescence, derived from healthy tissue, is greater than that of the fluorescence derived from cancerous tissue. Thus, cancerous tissue cain be found by illuminating internal tissue with the ultraviolet light and by reproducing the fluorescent images on the screen of the TV monitor.

In this case, it is frequently necessary to compare an image, based on the white light illumination, with a fluorescent image based on the ultraviolet light illumination, before a cancer tissue can be accurately and precisely found. Thus, this medical examination necessitates two electronic endoscope systems using a white light source and an ultraviolet source, and thus is very costly.

Furthermore, it is desirable to repeatedly perform a comparison between the normal image and the fluorescent image at frequent intervals, but this method of medical examination is practically impossible because the two scopes usually cannot be inserted in the patient body at the same time.

SUMMARY OF THE INVENTION

Therefore, an object of the present invention is to provide a novel electronic endoscope system utilizing both a usual white light source and a specific wavelength light source, which is constituted such that the usual white light source and the specific wavelength light source are quickly switched between each other.

In accordance with an aspect of the present invention, there is provided an electronic endoscope system, which comprises: a scope having an image sensor provided at a distal end thereof to generate image-pixel signals; an image-signal processing unit, to which a proximal end of the scope is connected, that processes the image-pixel signals to thereby produce a video signal; a light source device provided in the image-signal processing unit; and an optical light guide that extends through the scope, the optical light guide being optically connected to the light source device when the connection is established between the scope and the image-signal processing unit. The light source device includes a first light source that emits white light, a second light source that emits a specific wavelength light, and a light source switcher that selectively introduces either the white light or the specific wavelength light into the optical light guide.

Preferably, the light source switcher may include a light deflector, and a deflector-driving-mechanism that moves the light deflector between a first operative position and a second operative position. In this case, when the light deflector is positioned at the first operative position, the white light is introduced into the optical light guide. Also, when positioning the light deflector at the second operative position, the white light is blocked off by the light deflector, and the specific wavelength light is introduced by the light deflector into the optical light guide.

The light source switcher may further include an illumination mode selection system that selects one of a first illumination mode, in which the white light is introduced into the optical light guide, and a second illumination mode, in which the specific wavelength light is introduced into the optical light guide, and a controller that controls the deflector-driving-mechanism such that the light deflector is positioned at the first operative position when the first illumination mode is selected by the illumination mode selection system, and such that the light deflector is positioned at the second operative position when the second illumination mode is selected by the illumination mode selection system.

The light source device may further include a rotary color-filter/shutter, and a filter/shutter-driving-mechanism that moves the color-filter/shutter between a first operative position at which the color-filter/shutter functions as a rotary color filter and a second operative position at which the color-filter/shutter functions as a rotary shutter. The white light is converted into three primary color lights through the color-filter/shutter, positioned at the first operative position, whereby the three primary color lights are cyclically and sequentially introduced into the optical light guide. The specific wavelength light is cyclically and sequentially introduced into the optical light guide through the color-filter/shutter positioned at the second operative position.

The light source device may further include an illumination mode selection system that selects one of a first illumination mode, in which the white light is introduced into the optical light guide, and a second illumination mode, in which the specific wavelength light is introduced into the optical light guide, and a controller that controls the filter/shutter-driving-mechanism such that the color-filter/shutter is positioned at the first operative position when the first illumination mode is selected by the illumination mode selection system, and such that the color-filter/shutter is positioned at the second operative position when the second illumination mode is selected by the illumination mode selection system.

The rotary color-filter/shutter may comprise a disk element having-three primary color filters circumferentially spaced from each other at regular angular intervals. An area between two adjacent color filters is formed as a light-shielding area, and the light-shielding areas are radially and outwardly extended such that the extended areas form the rotary shutter. Optionally, only one of the light-shielding areas may be radially and outwardly extended such that the extended area forms the rotary shutter.

According to another aspect of the present invention, the light source device comprises a first light source that emits white light, a second light source that emits a-specific wavelength light, a light source switcher that selectively introduces one of the white light and the specific wavelength light into the optical light guide, and a rotary shutter associated with the second light source such that the rotary shutter is interposed in a specific wavelength-light path through which the specific wavelength light passes. The rotary shutter includes at least two light-shielding elements circumferentially spaced from each other at regular angular intervals and having different radial lengths. The light source device further comprises a shutter-driving-mechanism that relatively moves and positions the rotary shutter with respect to the specific-wavelength-light path such that the specific-wavelength-light path is selectively blocked off by the light-shielding elements having the different radial lengths, whereby an exposure time, during which the image sensor is illuminated with the specific wavelength blight, is varied.

Preferably, the light source device further comprises a rotary color filter interposed in a white-light path through which the white light passes, and a rotational frequency of the color filter is an integral multiple of that of the rotary shutter.

Preferably, the rotary shutter is moved by the shutter-driving mechanism between first and second relative positions with respect to the specific-wavelength-light path. When the rotary shutter is positioned at the first relative position, the specific-wavelength-light path is blocked off by a longer one of the light-shielding elements. When the rotary shutter is positioned at the second relative position, the specific-wavelength-light path is blocked off by both the light-shielding elements.

Preferably, the light source device further includes an exposure mode selection system that selects one of a first exposure mode, in which the specific-wavelength-light path is blocked off by the longer one of the light-shielding elements, and a second exposure mode, in which the specific-wavelength-light path being blocked off by both the light-shielding elements, and a controller that controls the shutter-driving-mechanism such that the rotary shutter is positioned at the first operative position when the first exposure mode is selected by the exposure mode selection system, and such that the rotary shutter is positioned at the second operative position when the second exposure mode is selected by the exposure mode selection system.

BRIEF DESCRIPTION OF THE DRAWINGS

The object and other objects of the present invention will be better understood from the following description, referring to the accompanying drawings, in which.

DESCRIPTION OF THE PREFERRED EMBODIMENTS

Figure 1:
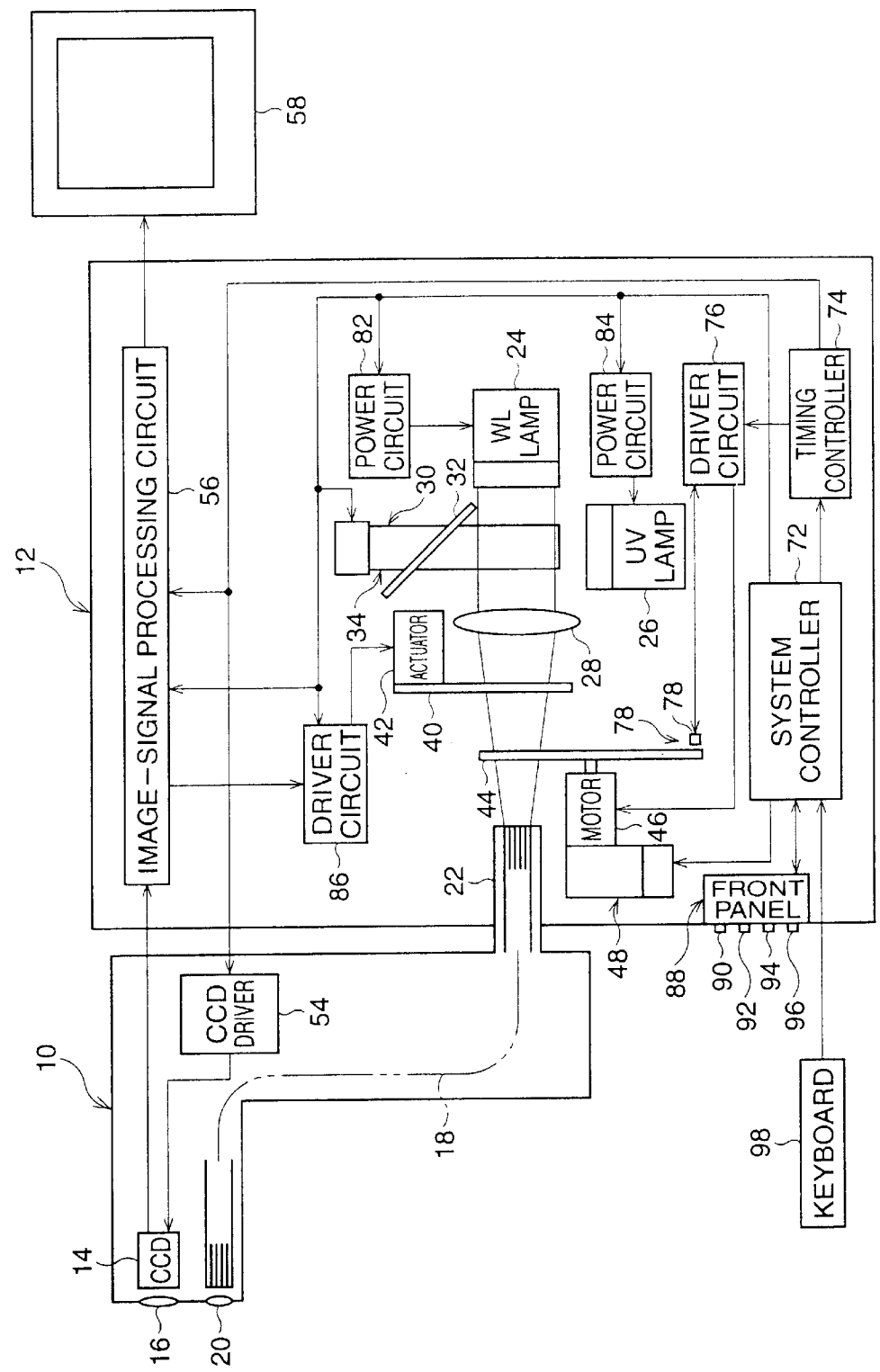
FIG. 1 is a schematic block diagram of a first embodiment of an electronic endoscope system according to the present invention.

With reference to FIG. 1, a first embodiment of an electronic endoscope system according to the present invention is schematically shown as a block diagram. The electronic endoscope system comprises an elongate scope 10 having a flexible conduit, and an image-signal processing unit 12 to which the scope 10 is detachably connected via a suitable connector device (not shown) The scope 10 includes a solid-state image sensor 14, such as a CCD (charge-coupled-device) image sensor, provided at a distal end of the flexible conduit thereof, and the CCD image sensor 14 is associated with an objective lens system 16.

The scope 10 also include-s a flexible optical light guide 18 extended therethrough and formed of a bundle of optical fibers. The optical light guide 18 terminates with a light-radiating end face at the distal end of the flexible conduit of the scope 10, and is associated with a lighting lens system 20 provided thereat. The optical light guide 18 has a connecting-adapter 22 provided at the proximal end thereof. When the connection is established between the scope 10 and the image-signal processing unit 12, the connecting-adapter 22 is received in a socket (not shown) provided in a housing of the image-signal processing unit 12, whereby the proximal end face of the optical light guide 18 is optically connected to a light source device, generally indicated by reference 19, provided in the image-signal processing unit 12. Note, in FIG. 1, a middle portion of the optical light guide 18 is represented by a double-dot-chain line for the shake of convenience.

The light source device 19 include-s two types of light source. Namely, in this embodiment, one type of light source comprises an usual white-light (WL) lamp 24, such as a halogen lamp, xenon lamp or the like, and the other type of light source comprises a specific wavelength light source or ultraviolet (UV) lamp 26. As shown in FIG. 1, the WL lamp 24 is aligned with the proximal end face of the optical light guide 18, and a condenser lens 28 is provided therebetween to converge the white light, emitted from the WL lamp 24, onto the proximal end face of the optical light guide 18. The UV lamp 26 is arranged such that the UV light emitted therefrom is directed to a region between the WL lamp 24 and the condenser lens 28 in a direction perpendicular to an optical axis of the condenser lens 28.

The light source device 19 is provided with a light-source switcher 30 which includes a light deflector or reflective mirror 32, and a driving-mechanism 34 for moving the mirror 32 between a first operative position and a second operative position. Note, in FIG. 1, the mirror 32 is at the first operative position. The mirror 32 is inclined such that a reflective surface thereof defines an angle of 45° with the optical axis of the condenser lens 28.

Figure 2:
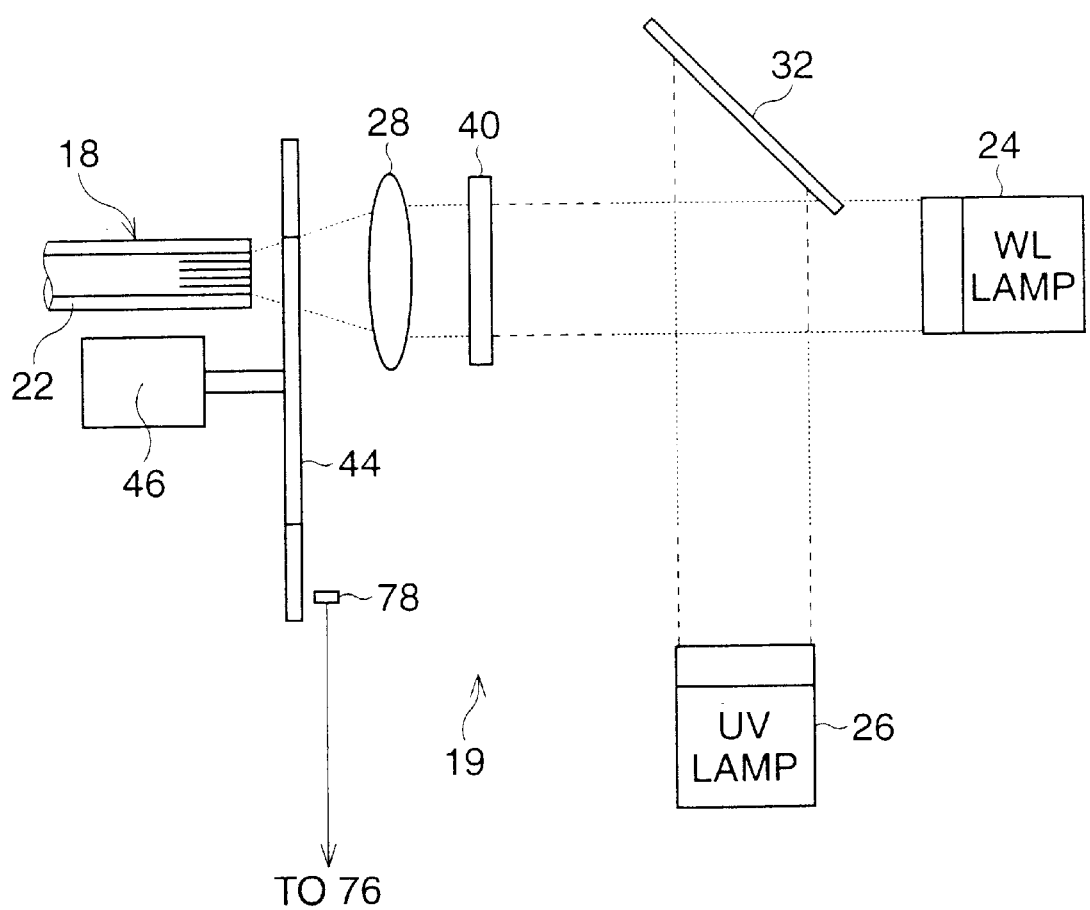
FIG. 2 is a schematic view showing a relative positional relationship of a mirror with respect to a white light lamp and an ultraviolet light lamp, the mirror being at a first operative position.
Figure 3:
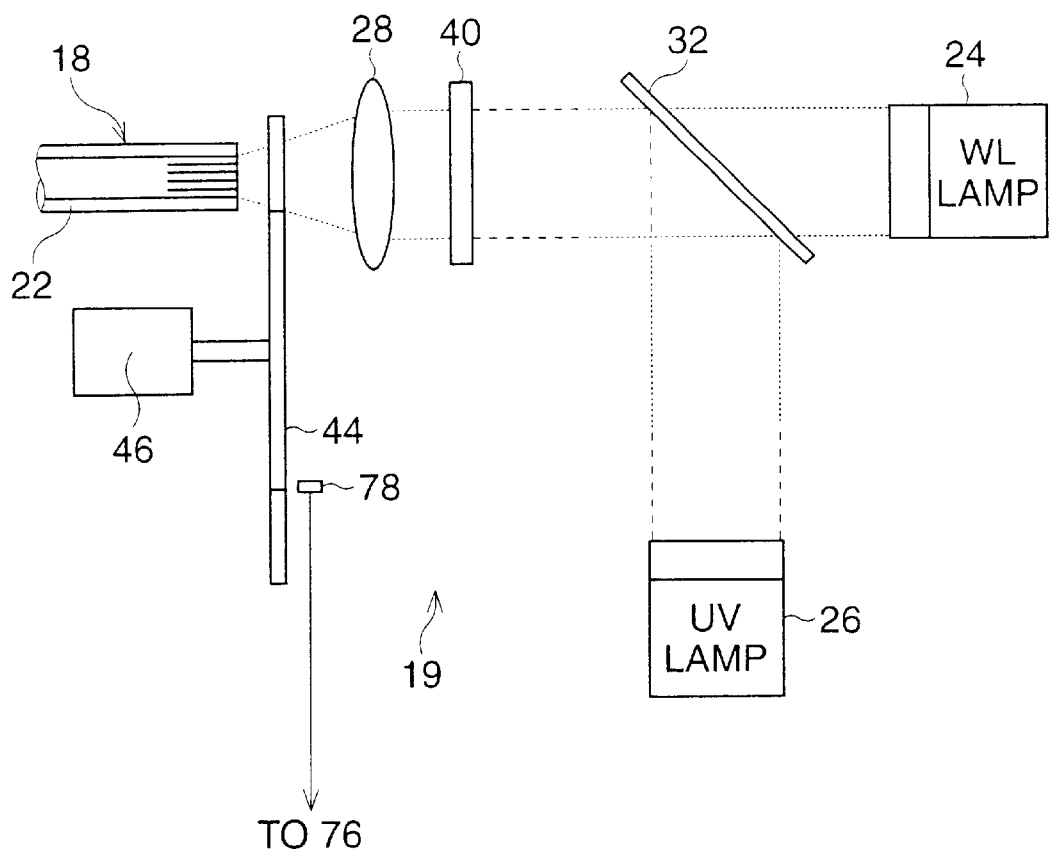
FIG. 3 is a schematic view, similar to FIG. 2, in which the mirror is at a second operative position.

FIGS. 2 and 3 show relative positional relationships of the mirror 32 with respect to the WL and UV lamps 24 and 26. Namely, in FIG. 2, the mirror 32 is shown as being at the first operative position, similar to FIG. 1, and, in FIG. 3, the mirror 32 is shown as being at the second operative position. When the mirror 32 is at the first operative position (FIG. 2), the white light, emitted from the WL lamp 24, is directed to the proximal end face of the optical light guide 18. When the mirror 32 is moved from the first operative position to the second operative position (FIG. 3), i.e. when the mirror 32 is intervened between the WL lamp 24 and the condenser lens 28, the white light, emitted from the WL lamp 24, is blocked off by the rear surface of the mirror 32, and the UV light, emitted from the UV lamp 26, is reflected by the reflective surface of the mirror 32 and directed to the condenser lens 28.

In short, when the mirror 32 is at the first operative position (FIG. 2), the white light is introduced from the WL lamp 24 into the optical light guide 18, and when the mirror 32 is at the second operative position (FIG. 3), the UV light is introduced from the UV lamp 26 into the optical light guide 18.

Figure 4:
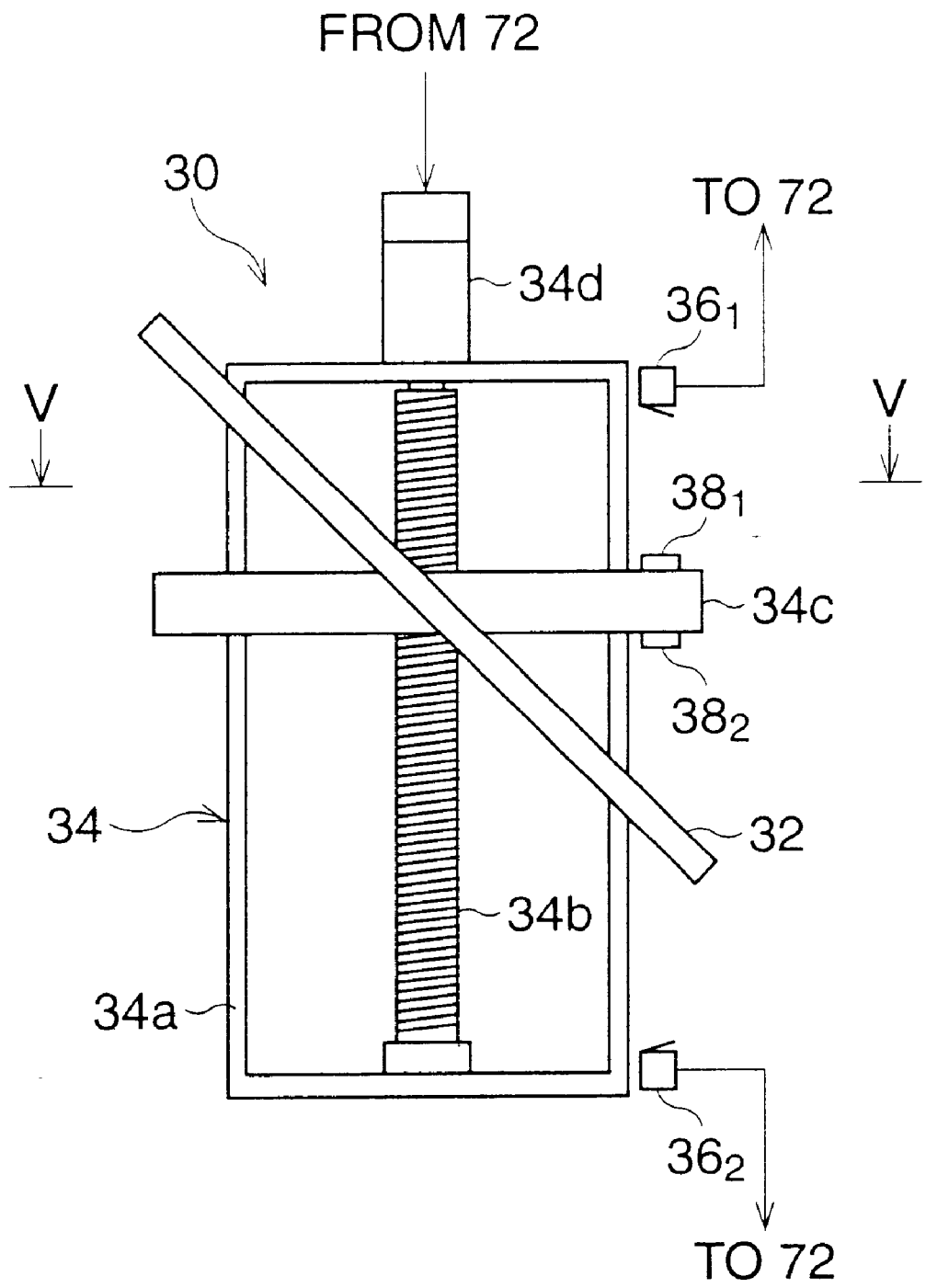
FIG. 4 is a schematic front view of a driving-mechanism for moving the mirror between the first and second operative positions.
Figure 5:
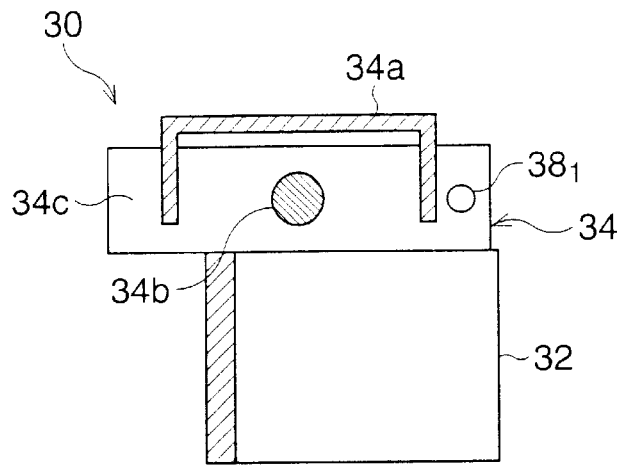
FIG. 5 is a cross-sectional view taken on line V—V of FIG. 4.

FIGS. 4 and 5 show an arrangement for the driving-mechanism 34 for moving the light-deflector 32 between the first and second operative positions. The driving-mechanism 34 includes a rectangular frame member 34a securely supported by an internal frame structure (not shown) of the image-signal processing unit 12, a ball screw 34b rotatably supported by and longitudinally extended through the frame member 34a, and a movable plate member 34c threaded on the ball screw 34b. As shown in FIG. 5, the plate member 34c has two slots formed therein, and lateral side walls of the frame member 34a are slidably received in the slots.

As shown in FIG. 4, the driving-mechanism 34 is provided with an electric motor 34d, such as a servo motor, a stepping motor or the like, mounted on the top of the frame member 34a, and an output shaft of the motor 34d is coupled to an upper end of the ball screw 34b. Thus, when the ball screw 34b is rotated by the motor 34d, the plate member 34c is moved upward and downward along the ball screw 34b, with the direction of movement of the plate member 34c depending on the rotational direction of the ball screw 34b.

As is apparent from FIGS. 4 and 5, the mirror 32 is securely attached to a front face of the plate member 34c such that the reflective surface thereof defines the angle of 45° with the optical axis of the condenser lens 28. Thus, it is possible to move the mirror 32 between the first and second operative positions by suitably controlling the motor 34d.

In order to suitably control the motor 34d to exactly position the mirror 32 at each of the first and second operative positions, as shown in FIG. 4, a first limit switch $36_1$ and a second limit switch $36_2$ are arranged near the upper and lower ends of one of the lateral walls of the frame member 34a, and a first dog $38_1$ and a second dog $38_2$ are securely mounted on upper and lower surfaces of an end portion of the plate member 34c interposed between the first and second limit switches $36_1$ and $36_2$, with the elements $36_1$, $36_2$, $38_1$ and $38_2$ being aligned with each other and parallel to the lateral wall of the frame member 34a. Note, preferably, the first and second limit switches $36_1$ and $36_2$ are securely attached to the lateral wall of the frame member 34a.

The first and second limit switches $36_1$ and $36_2$ are placed at respective locations corresponding to the first and second operative positions for the mirror 32, and are usually in an OFF-state. When the motor 34d is driven such that the plate member 34c is moved toward the first limit switch $36_1$, the first dog $38_1$ comes into contact with the first limit switch $36_1$, thereby turning ON the first limit switch $36_1$. When the first limit switch $36_1$ is turned ON, the motor 34d is stopped, and thus the mirror 32, supported by the plate member 34c, is positioned at the first operative position (FIG. 2). Similarly, when the motor 34d is driven such that the plate member 34c is moved toward the second limit switch $36_2$, the second dog $38_2$ comes into contact with the second limit switch $36_2$, thereby turning ON the second limit switch $36_2$. When the second limit switch $36_2$ is turned ON, the motor 34d is stopped, and thus the mirror 32, supported by the plate member 34c, is positioned at the second operative position (FIG. 3).

Again referring to FIG. 1, the light source device 19 further includes a diaphragm 40 provided between the condenser lens 28 and the proximal end face of the optical light guide 18. The diaphragm 40 is used to adjust an amount of light directed from either the WL lamp 24 or the UV lamp 26 onto the proximal end of the optical light guide 18, i.e. the amount of illuminating-light radiating from the distal end of the optical light guide 18 can be regulated by the diaphragm 40.

In this embodiment, the CCD image sensor 14 is constituted as a monochromatic CCD image sensor. When the mirror 32 is positioned at the first operative position, i.e. when the WL lamp 24 is selected as the light source, an RGB field sequential-type color imaging method is introduced in the electronic endoscope system, thereby obtaining a full color image from the monochromatic CCD image sensor 14. On the other hand, when the mirror 32 is positioned at the second operative position, i.e. when the UV lamp 26 is selected as the light source, a monochromatic image is obtained from the CCD image sensor 14.

To this end, a rotary color-filter/shutter 44 is interposed between the diaphragm 40 and the proximal end face of the optical light guide 18. When the WL lamp 24 is selected, the rotary color-filter/shutter 44 serves as a rotary RGB color filter, and when the UV lamp 26 is selected, the rotary color-filter/shutter 44 serves as a rotary shutter.

Figure 6:
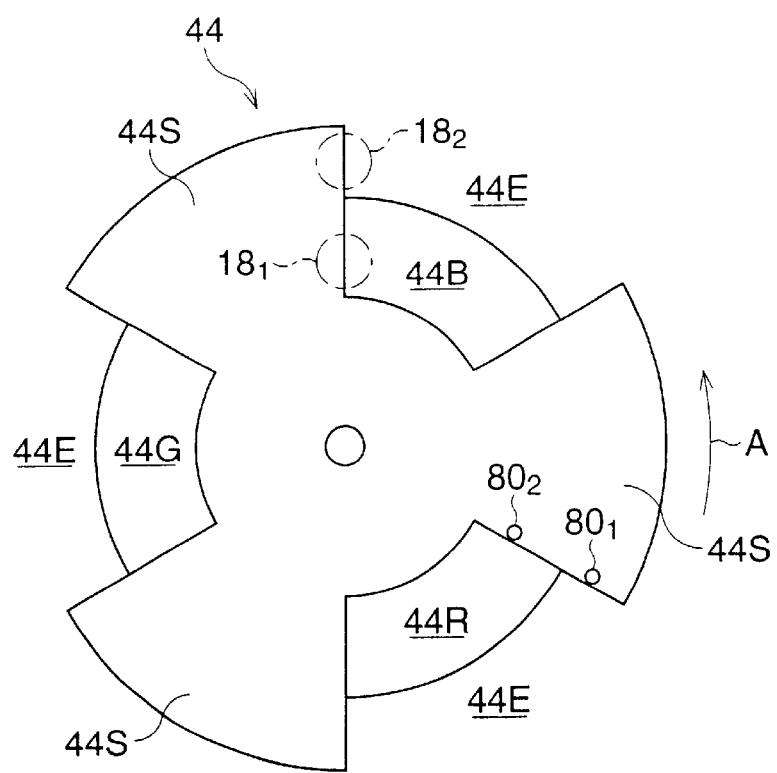
FIG. 6 is a plan view of a rotary color-filter/shutter used in the first embodiment of the electronic endoscope according to the present invention.

As shown in FIG. 6, the rotary color-filter/shutter 44 comprises a disk element having three sector-shaped color filters, i.e. red, green and blue filters 44R, 44G and 44B, which are circumferentially and uniformly arranged such that three centers of the color filters 44R, 44G and 44B are spaced from each other at regular angular intervals of 120 degrees. A sector area between two adjacent color filters is constructed as a light-shielding area 44S, and each light-shielding area 44S is radially and outwardly extended such that a sector-like opening or exposure area 44E is defined between two adjacent light-shielding areas 44S.

As shown in FIG. 1, the rotary color-filter/shutter 44 is securely mounted on an output shaft of a suitable electric motor 46, such as servo-motor, a stepping motor or the like, and is rotated by driving the motor 46 at a given rotational frequency in accordance with a commonly used image-reproduction method, such as the NTSC system, the PAL system and so on. For example, in the NTSC system, the rotational frequency of the rotary color-filter/shutter 44 is 30 Hz, and, in the PAL system, the rotational frequency of the rotary color-filter/shutter 44 is 25 Hz.

The rotary color-filter/shutter 44 is moved between a first operative position shown in FIG. 2 and a second operative position show in FIG. 3, and the motor 46 is associated with a driving-mechanism 48 for the movement of the rotary color-filter/shutter 44 between the first and second operative positions, as shown in FIG. 1.

Figure 7:
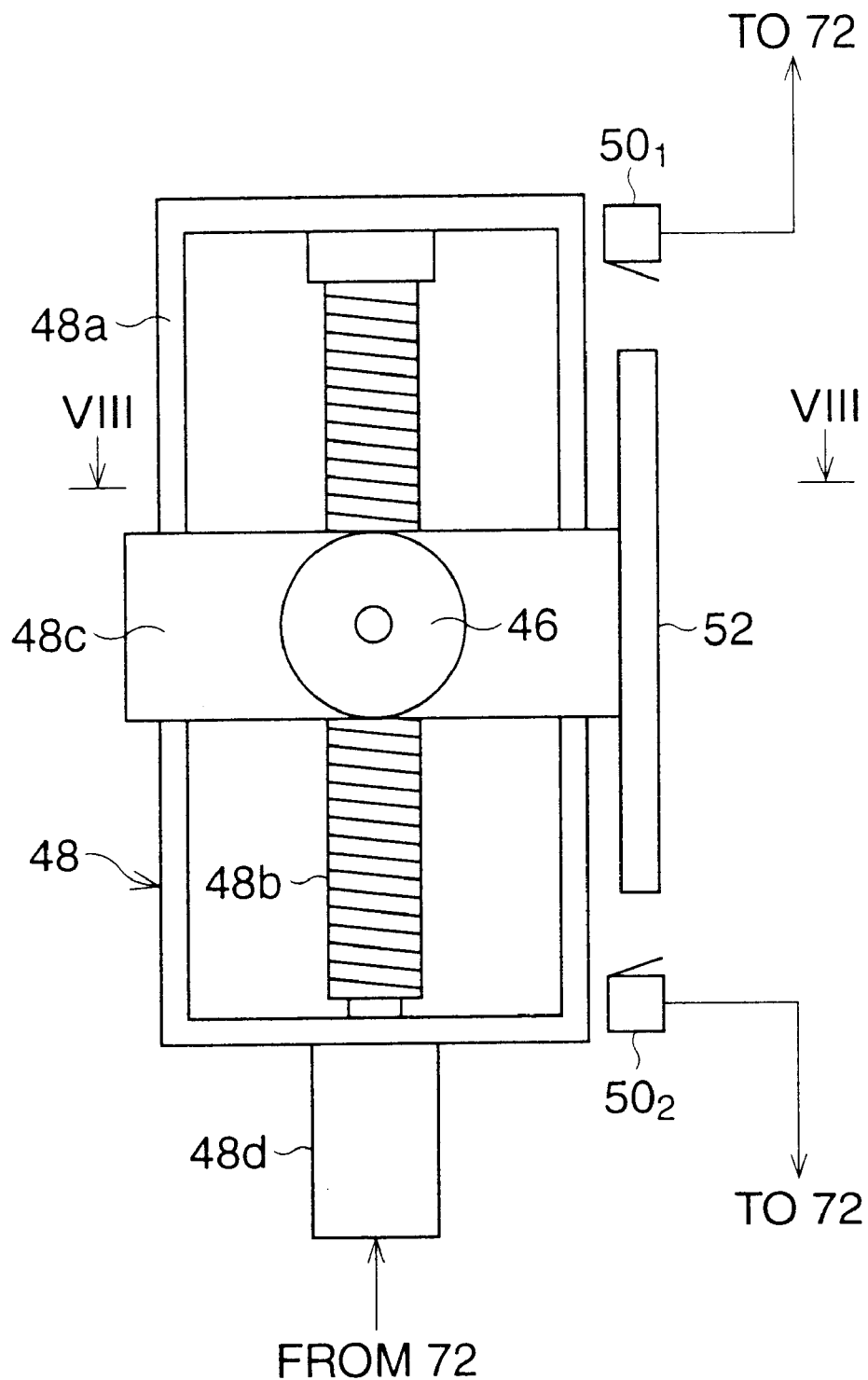
FIG. 7 is a schematic front view of a driving-mechanism for moving the rotary color-filter/shutter between a first operative position and a second operative position.
Figure 8:
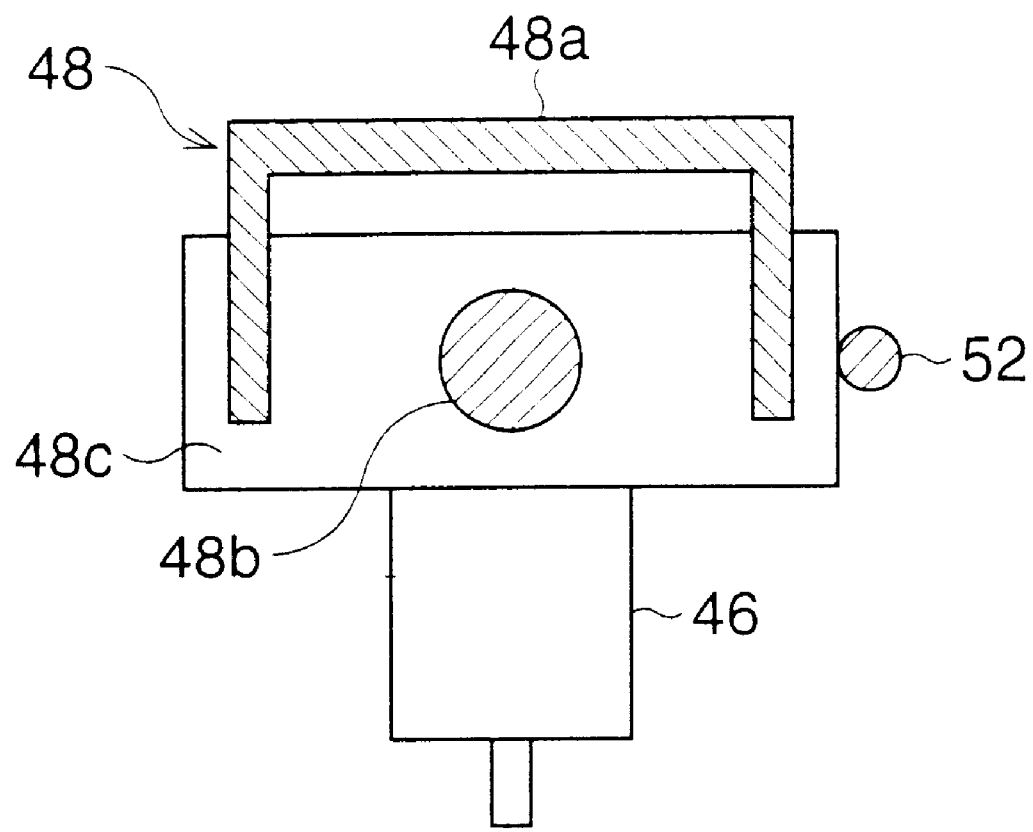
FIG. 8 is a cross-sectional view taken on line VIII—VIII of FIG. 7.

With reference to FIGS. 7 and 8, an arrangement for the driving-mechanism 48 is illustrated. The driving-mechanism 48 includes a rectangular frame member 48a securely supported by the internal frame structure of the image-signal processing unit 12, a ball screw 48b rotatably supported by and longitudinally extended through the frame member 48a, and a movable block member 48c threaded on the ball screw 48b. As shown in FIG. 8, the block member 48c has two slots formed therein, and lateral side walls of the frame member 48 a are slidably received in the slots.

As shown in FIG. 7, the driving-mechanism 48 is provided with an electric motor 48d, such as a servo motor, a stepping motor or the like, mounted on the bottom of the frame member 48a, and an output shaft of the motor 48d is coupled to an lower end of the ball screw 48b. Thus, when the ball screw 48b is rotated by driving the motor 48d, the block member 48c is moved upward and downward along the ball screw 48b, with the direction of movement of the block member 48c depending on the rotational direction of the ball screw 48b.

As is apparent from FIGS. 7 and 8, the motor 46 for the rotary color-filter/shutter 44 is securely attached to a front face of the block member 48c. Thus, it is possible to move the rotary color-filter/shutter 44 between the first and second operative positions by suitably controlling the motor 48d.

In order to suitably control the motor 48d to exactly position the rotary color-filter/shutter 44 at each of the first and second operative positions as shown in FIG. 7, a first limit switch $50_1$ and a second limit switch $50_2$ are arranged near the upper and lower ends of one of the lateral walls of the frame member 48a, and a rod-like dog 52 is securely attached to an end of the block member 48c interposed between the first and second limit switches $50_1$ and $50_2$, with the ends of the rod-like dog 52 being aligned with the first and second limit switches $50_1$ and $50_2$ and parallel to the lateral wall of the frame member 48a. Note, preferably, the first and second limit switches $50_1$ and $50_2$ are securely attached to the lateral wall of the frame member 48a.

The first and second limit switches $50_1$ and $50_2$ are placed at respective locations corresponding to the first and second operative positions for the rotary color-filter/shutter 44, and are usually in an OFF-state. When the motor 48d is driven such that the block member 48c is moved toward the first limit switch $50_1$, the upper end of the rod-like dog 52 comes into contact with the first limit switch $50_1$, thereby turning ON the first limit switch 50. When the first limit switch $50_1$ is turned ON, the motor 48d is stopped, and thus the rotary color-filter/shutter 44, supported by the block member 48c, is positioned at the first operative position (FIG. 2). Similarly, when the motor 48d is driven such that the block member 48c is moved toward the second limit switch $50_2$, the lower end of rod-like dog 52 comes into contact with the second limit switch $50_2$, thereby turning ON the second limit switch $50_2$. When the second limit switch $50_2$ is turned ON, the motor 48d is stopped, and thus the rotary color-filter/ shutter 44, supported by the block member 48c, is positioned at the second operative position (FIG. 3).

The driving-mechanism 30 for the mirror 32 and the driving mechanism 48 for the rotary color-filter/shutter 44 are operated in conjunction with each other. Namely, when the driving-mechanism 30 is operated such that the mirror 32 is positioned at the first position, i.e. that the WL lamp 24 is selected as the illuminating-light source, the driving-mechanism 48 is also operated such that the rotary color-filter/shutter 44 is positioned at the first operative position. Also, when the driving-mechanism 30 is operated such that the mirror 32 is positioned at the second position, i.e. that the UV lamp 2& is selected as the illuminating-light source, the driving-mechanism 48 is also operated such that the rotary color-filter/shutter 44 is positioned at the second operative position.

When the rotary color-filter/shutter 44 is positioned at the first operative position, i.e. when the WL lamp 24 is selected, the proximal end face of the optical light guide 18 is relatively positioned with the rotary color-filter/shutter 44, as illustrated with a single-dot line indicated by reference $18_1$ in FIG. 6. Namely, the proximal end face ($18_1$) of the optical light guide 18 is encompassed by an annular area which is defined by the red, green and blue filters 44R, 44G and 44B. Thus, while the rotary color-filter/shutter 44 is rotated in a direction indicated by arrow A in FIG. 6, red, green and blue lights are cyclically and sequentially made incident on the proximal end face ($18_1$) of the optical light guide 18, i.e. the red, green and blue lights are cyclically and sequentially emitted from the distal end face of the optical light guide 18. Note, this lighting mode is referred to as a WL illumination mode hereinafter.

On the other hand, when the rotary color-filter/shutter 44 is positioned at the second operative position, i.e. when the UV lamp 26 is selected, the proximal end face of the optical light guide 18 is relatively positioned with the rotary color-filter/shutter 44, as illustrated with a single-dot line indicated by reference $18_2$ in FIG. 6. Namely, the proximal end face ($18_2$) of the optical light guide 18 is encompassed by an annular area which is defined by the sector-like exposure areas 44E. Thus, while the rotary color-filter/shutter 44 is rotated in the direction indicated by arrow A in FIG. 6, UV light is cyclically and sequentially made incident on the proximal end face ($18_2$) of the optical light guide 18, i.e. the UV light is cyclically and sequentially emitted from the distal end face of the optical light guide 18. Note, this lighting mode is referred to as a UV illumination mode hereinafter.

As is apparent from the foregoing, in the WL illumination mode, the rotary color-filter/shutter 44 serves as the rotary RGB color filter. If the NTSC system is introduced into the electronic endoscope system, the rotary color-filter/shutter 44 is rotated by the motor 46 at a rotational frequency of 30 Hz. In this case, the rotary color-filter/shutter 44 makes one revolution over a time period of 1/30 sec (about 33.3 ms), and thus the white light, emitted from the WL lamp 24, passes through each of the color filters 44R, 44G and 44B over a time period of 1/180 sec (about 33.3/6 ms). Thus, the red, green and blue lights sequentially and cyclically radiate from the distal end of the optical light guide 18. Namely, red, green and blue optical images are sequentially and cyclically focused on the light-receiving surface of the CCD image sensor 14.

While the red, green and blue optical images are cyclically focused on the light-receiving surface of the CCD image sensor 14, each of the red, green and blue optical images is converted into a frame of monochromatic (red, green, blue) analog image-pixel signals by the CCD image sensor 14, and each frame of monochromatic analog image-pixel signals is read from the CCD image sensor 14 over consecutive light-shielding time periods (about 33.3/6 ms) corresponding to the light-shielding area 44S between two adjacent color filters (44R, 44G, 44B) of the rotary color-filter/shutter 44.

As shown in FIG. 1, the scope 10 is provided with a CCD driver 54, by which the analog image-pixel signals from the CCD image sensor 14 are read. Also, the image-signal processing unit 14 includes an image-signal processing circuit 56, to which the read analog image-pixel signals are fed. In the image-signal processing circuit 56, the image-pixel signals are suitably processed to produce a component-type color video signal. Then, the component-type video signal is output from the image-signal processing unit 14 to a TV monitor 58, and an endoscope-image is reproduced and displayed as a full color image on the screen of the TV monitor. 58 in accordance with the video signal.

Figure 9:
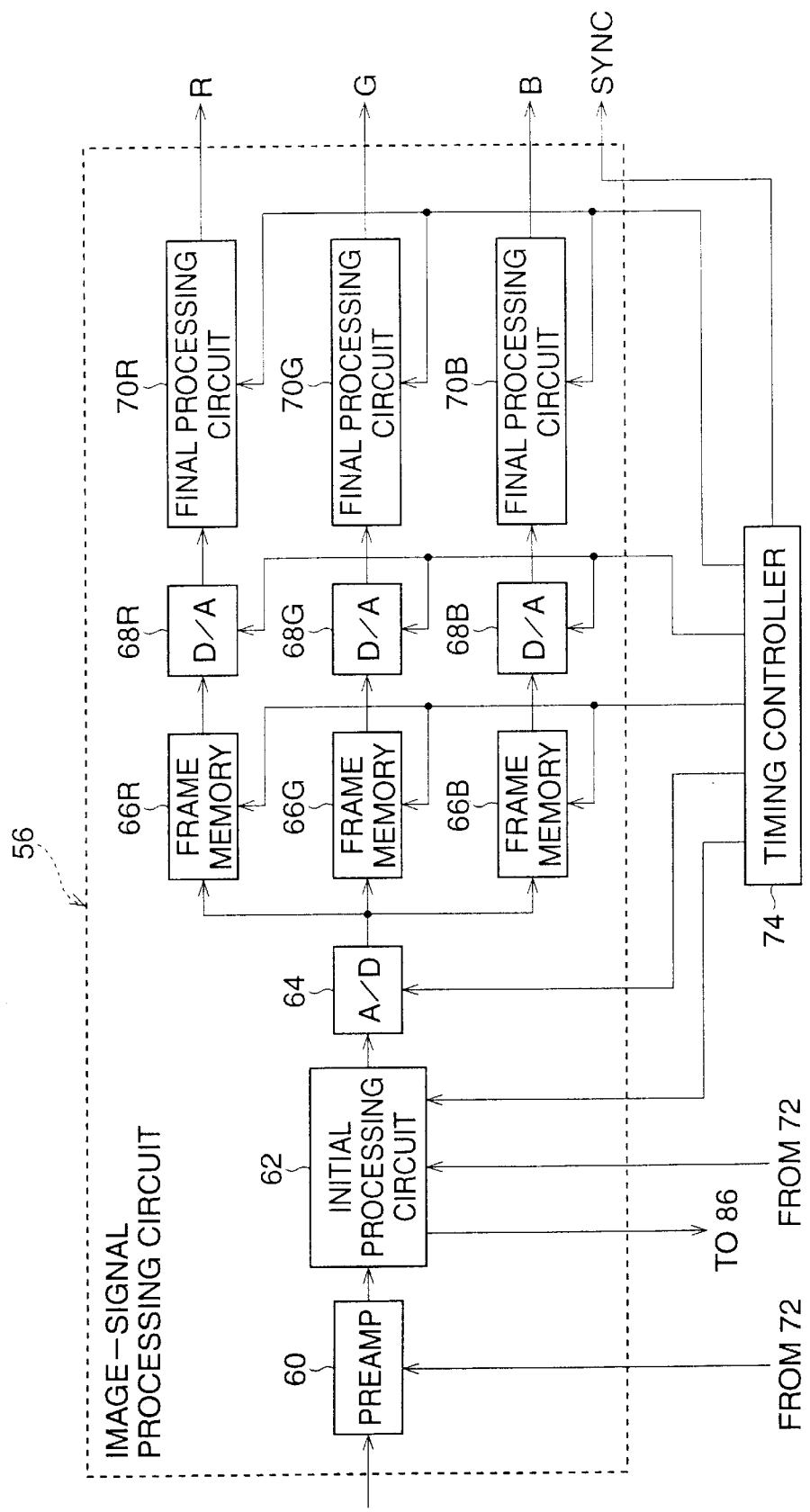
FIG. 9 is a block diagram of an image-signal processing circuit shown in FIG. 1.

With reference to FIG. 9, the image-signal processing circuit 56 is shown as a detailed block diagram.

As shown in FIG. 9, the image-signal processing circuit 56 includes a preamplifier 60, an initial processing circuit 62 and an analog-to-digital (A/D) converter 64. In the WL illumination mode, monochromatic (red, green, blue) analog image-pixel signals, which are successively read from the CCD image sensor 14, are input to the preamplifier 60 in which each analog image-pixel signal is amplified with a predetermined amplification factor. Then, the amplified analog image-pixel signals are suitably processed in the initial processing circuit 62. For example, the monochromatic analog image-pixel signals are subjected to noise-elimination, white-balance correction, gamma-correction, profile-enhancing, black-level-clamping and so on. Then, the processed monochromatic analog image-pixel signals are converted into monochromatic (red, green, blue) digital image-pixel signals by the A/D converter 64.

Note, in this embodiment, the preamplifier 60 is formed as a voltage-controlled amplifier (VCA), an amplification factor of which is altered in accordance with a level of voltage applied thereto.

The image-signal processing circuit 56 also includes frame memories 66R, 66G and 66B for temporarily storing the red, green and blue digital image-pixel signals, respectively. In short, the monochromatic digital image-pixel signals are stored in the frame memory 66R, 66G or 66B that corresponds to the image pixel color. While the color digital image-pixel signals are successively stored in the frame memories 66R, 66G and 66B, the respective red, green and blue digital image-pixel signals are simultaneously read from the frame memories 66R, 66G and 66B, and are output as red, green and blue digital video signal components, respectively.

The image-signal processing circuit 56 further includes digital-to-analog (D/A) converters 68R, 68G and 68B, and final-processing circuits 70R, 70G and 70B. The respective red, green and blue digital video signal components, output from the frame memories 66R, 66G and 66B, are converted by the D/A converters 68R, 68G and 68B into red, green and blue analog video signal components. Then, the respective red, green and blue analog video signal components are suitably processed in the final-processing circuits 70R, 70G and 70B. For example, the respective red, green and blue analog video signal components are subjected to noise-elimination, white-balance correction, gamma-correction, profile-enhancing and so on. The processed red, green and blue analog video signal components (R, G and B) are output from the image-processing circuit 56 to the TV monitor 58.

As shown in FIG. 1, the image-signal processing unit 12 is provided with a system controller 72 which controls the electronic endoscope system as a whole. In this embodiment, the system controller 72 is constituted as a microcomputer comprising a central processing unit (CPU), a read-only memory (ROM) for storing programs and constants, a random-access memory (RAM) for storing temporary data, and an input/output interface circuit (I/O).

The image-signal processing unit 12 is further provided with a timing controller 74, which outputs various series of clock pulses under control of the system controller 72, to operate sequentially and systematically the CCD driver 54 and the image-signal processing circuit 56.

The CCD driver 54 is systematically operated in accordance with a series of timing-clock pulses, output from the timing controller 74, such that the image-pixel signals included in each frame are read from the CCD image sensor 14 in a regular sequence. Namely, whenever a timing-clock pulse is input from the timing controller 74. to the CCD driver 54, a series of reading-clock pulses is output from the CCD driver 54 to the CCD image sensor 14, whereby the reading of the image-pixel signals from the CCD image sensor 14 is performed in accordance with the reading-clock pulses.

As is apparent from FIG. 9, the image-signal processing circuit 56 is systematically operated in accordance with various series of clock pulses, output from the timing controller 74, such that the read image-pixel signals are processed in synchronization with the reading of image-pixel signals from the CCD image sensor.

In particular, in the image-signal processing circuit 56, the initial processing circuit 62 is systematically operated in accordance with a series of clock pulses, output from the timing controller 74, such that the various image processings, such as noise-elimination, white-balance correction, gamma-correction, profile-enhancing, black-level-clamping and so on, are performed in a regular sequence. The A/D converter 64 is systematically operated in accordance with a series of clock pulses output from the timing controller 74, such that the conversion of analog image-pixel signals into digital image-pixel signals is performed in a regular sequence.

Further, the writing of digital image-pixel signal in the memories 66R, 66G and 66B and the reading of digital image-pixel signal from the memories 66R, 66G and 66B are performed in a regular sequence in accordance with series of clock pulses output from the timing controller 74. The D/A converters 68R, 68G and 68B are systematically operated in accordance with a series of clock pulses output from the timing controller 74, so that the conversion of the red, green and blue digital video signal components into the red, green and blue analog video signal components is performed in a regular sequence. The final image processing circuits 70R, 70G and 70B are systematically operated in accordance with a series of clock pulses, output from the timing controller 74, so that the various image processings, such as noise-elimination, white balance correction, gamma-correction, profile-enhancing and so on, are performed in a regular sequence.

As shown in FIG. 9, the timing controller 74 also produces a compound-synchronizing-signal component (SYNC), which includes various synchronizing signals, such as a horizontal synchronizing signal, a vertical synchronizing signal and so on, and is output from the image-signal processing circuit 56, together with the red, green and blue video signal components (R, G and B), to the TV monitor 58. In short, in the image-signal processing circuit 56, the component-type analog video signal is produced on the basis of image-pixel signals successively obtained from the CCD image sensor 14.

On the other hand, in the UV illumination mode, the rotary color-filter/shutter 44 serves as a rotary shutter (FIG. 3), and is rotated at the same rotational frequency (30 Hz) as the WL illumination mode. Namely, the rotary color-filter/shutter or rotary shutter 44 makes one revolution over the time period of 1/30 sec (about 33.3 ms), and thus the UV light, emitted from the UV lamp 26, passes through each of the sector-shaped exposure areas 44E over the time period of 1/180 sec (about 33.3/6 ms). Thus, the UV light sequentially and cyclically radiates from the distal end of the optical light guide 18.

As mentioned hereinbefore, when internal tissue of a person is irradiated with the UV light, the irradiated tissue generates fluorescence. Thus, optical fluorescent images are sequentially and cyclically focused on the light-receiving surface of the CCD image sensor 14.

While the fluorescent images are cyclically focused on the light-receiving surface of the CCD image sensor 14, each of the fluorescent images is converted into a frame of analog image-pixel signals by the CCD image sensor 14, and the frame of analog image-pixel signals is read from the image sensor 14 over consecutive light-shielding time periods (about 3.3/6 ms) corresponding to the light-shielding area 44S between two adjacent sector-like exposure areas (44E) of the rotary color-filter/shutter 44.

The analog image-pixel signals are read from the CCD image sensor 14 in a regular sequence by operating the CCD driver 54 in the same manner as the WL illumination mode, and the read analog image-pixel signals are also processed in the signal-processing circuit 56 in substantially the same manner as the WL illumination mode.

In particular, the respective frame memories 66R, 66G and 66B store three frames of digital-image pixels, which are derived from the three fluorescent images formed on the light-receiving surface of the CCD image sensor 14 every revolution of the rotary color-filter/shutter 44. The respective frames of digital-image pixels are simultaneously read from the frame memories 66R, 66G and 66B, and are converted by the D/A converters 68R, 68G and 68B into monochromatic analog video signal components. Then, the respective monochromatic analog video signal components are processed in the final processing circuits 70R, 70G and 70B. Namely, in the UV illumination mode, the image-signal processing circuit 56 produces the three monochromatic analog video signal components, corresponding to the red, green and blue analog video signal components obtained in the WL illumination mode, but the fluorescent image is reproduced and displayed as a monochromatic image on the screen of the TV monitor 58 on the basis of any one of the three monochromatic analog video signal components and the compound-synchronizing signal component (SYNC).

In short, by using the rotary color-filter/shutter 44 as shown in FIG. 6, it is possible to use the image-signal processing circuit 56 in common in the WL and UV illumination modes, and it is therefore unnecessary to provide a separate image-processing circuit for the UV illumination mode in the image-processing unit 12.

However, although the CCD image sensor 14 is highly sensitive to the red, green and blue light, it exhibits a low sensitivity to the fluorescent light. Accordingly, in the UV illumination mode, a higher amplification factor should be set to the preamplifier 60 in comparison with the WL illumination mode. The setting of the amplification factor to the preamplifier 60 (FIG. 9) is altered by the system controller 72 whenever the WL illumination mode is switched to the UV illumination mode and vice versa.

Also, the amplified image-pixel signals, derived from the ultraviolet illumination, include higher frequency noise than that of the amplified image-pixel signals derived from the white light illumination. Thus, in the initial processing circuit 62, a noise-filtering circuit for the noise-elimination should be set such that the higher frequency noise is eliminated in the UV illumination mode. The setting of the noise-filtering circuit is altered by the system controller 72 whenever the WL illumination mode is switched to the UV illumination mode and vice versa.

Further, in the initial processing circuit 62, a clamp circuit for the black-level-clamping should be set such that respective different black (pedestal) levels are obtained in the WL and UV illumination modes, because the CCD image sensor 14 exhibits different sensitivities to the red, green and blue lights and the fluorescent light. The setting of the clamp circuit is altered by the system controller 72 whenever the WL illumination mode is switched to the UW illumination mode and vice versa.

As is apparent from FIG. 4, the driving-mechanism 34 for the movement of the mirror 32 is operated under control of the system controller 72. Namely, the first and second limit switches $36_1$ and $36_2$ are connected to the system controller 72, and the electric motor 34d is driven under control of the system controller 72. In particular, during the movement of the plate member 34c toward the first limit switch $36_1$, the system controller 72 monitors whether the first limit switch $36_1$ is turned ON by the first dog $38_1$. When the first limit switch $36_1$ is turned ON, the motor 34d is stopped by the system controller 72, and thus the mirror 32 is positioned at the first operative position (FIG. 2). Also, during the movement of the plate member 34c toward the second limit switch $36_2$, the system controller 72 monitors whether the second limit switch $36_2$ is turned ON by the second dog $38_2$. When the second limit switch $36_2$ is turned ON, the motor 34d is stopped by the system controller 72, and thus the mirror 32 is positioned at the second operative position (FIG. 3).

As is apparent from FIG. 7, the driving-mechanism 48 for the movement of the rotary color-filter/shutter 44 is also operated under control of the system controller 72. Namely, the first and second limit switches $50_1$ and $50_2$ are connected to the system controller 72, and the electric motor 48d is driven under control of the system controller 72. In particular, during the movement of the block member 48c toward the first limit switch $50_1$, the system controller 72 monitors whether the first limit switch $50_1$ is turned ON by the upper end of the rod-like dog 52. When the first limit switch $50_1$ is turned ON, the motor 48d is stopped by the system controller 72, and thus the rotary color-filter/shutter 44 is positioned at the first operative position (FIG. 2). Also, during the movement of the block member 48c toward the second limit switch $50_2$, the system controller 72 monitors whether the second limit switch $50_2$ is turned ON by the lower end of the rod-like dog 52. When the second limit switch $50_2$ is turned ON, the motor 48d is stopped by the system controller 72, and thus the rotary color-filter/shutter 44 is positioned at the second operative position (FIG. 3).

As mentioned above, each frame of image-pixel signals are read from the CCD image sensor 14 in a regular sequence by the CCD driver 54, in accordance with the series of timing-clock pulses output from the timing controller 74. It is necessary to always precisely synchronize the output timing of the timing-clock pulses from the timing controller 74 to the CCD driver 54 with the rotation of the rotary color-filter/shutter 44, before the reading of image-pixel signals from the CCD image sensor 14 can be performed at a proper timing. To this end, as shown in FIG. 1, the motor 46 is driven by a driver circuit 76, which is controlled by the system controller 72 and the timing controller 74 such that the output timing of the timing-clock pulses from the timing controller 74 to the CCD driver 54 is synchronized with an output timing of drive pulses from the driver circuit 76 to the motor 46.

However, in reality, it is impossible to obtain precise synchronization between each revolution of the rotary color-filter/shutter 44 and the output timing of the timing-clock pulses from the timing controller 74 to the CCD driver 54, because the motor 46 inevitably involves rotational errors, and because these errors accumulate while the motor 46 is driven.

As shown in FIG. 1, a phase detector 78 is arranged at a suitable location to detect a rotational-phase of the rotary color-filter/shutter 44 in order to facilitate the elimination of the rotational errors of the motor 46. In this embodiment, the phase detector 78 comprises a light-emitting element, such as an light-emitting diode (LED), and a light-receiving element, such as a photodiode (PD).

On the other hand, the rotary color-filter/shutter 44 has first and second small reflective areas $80_1$ and $80_2$ formed thereon, and the reflective areas $80_1$ and $80_2$ are aligned with each other along a radial edge of a light-shielding area 44S, which bounds on the red filter 44R, as shown in FIG. 6. The distance between the first and second small reflective areas $80_1$ and $80_2$ corresponds to that between the first and second operative positions for the rotary color-filter/shutter 44. Note, each of the reflective areas $80_1$ and $80_2$ may be formed by adhering a small piece of aluminum foil on the rotary color-filter/shutter 44.

While the rotary color-filter/shutter 44 is rotated at the first operative position (FIG. 2), the phase detector 78 detects the passage of the first small reflective area $80_1$. Also, while the rotary color-filter/shutter 44 is rotated at the second operative position (FIG. 3), the phase detector 78 detects the passage of the second small reflective area $80_2$. Namely, when the light, emitted from the LED of the phase detector 78, is reflected by the small reflective area (80₁, 80₂), during the rotation of the rotary color-filter/shutter 44, the reflected light is received by the PD of the phase detector 78, whereby the rotational-phase of the rotary color-filter/shutter 44 is detected by the phase detector 78.

When the reflected light is received by the PD of the phase detector 78, the PD outputs a phase-detection pulse to the driver circuit 76. The driver circuit 76 includes a phase-locked-loop (PLL) circuit, and outputs the drive pulses to the motor 46 such that a phase of the phase-detection pulse coincides with a phase of the drive pulses every revolution of the rotary color-filter/shutter 44, thereby eliminating the rotational error of the motor 46. Thus, it is possible to always precisely synchronize the output timing of the timing-clock pulses from the timing controller 74 to the CCD driver 54 with each revolution of the rotary color-filter/shutter 44, whereby the reading of the image-pixel signals from the CCD image sensor 14 can be performed at the proper timing.

Figure 10:
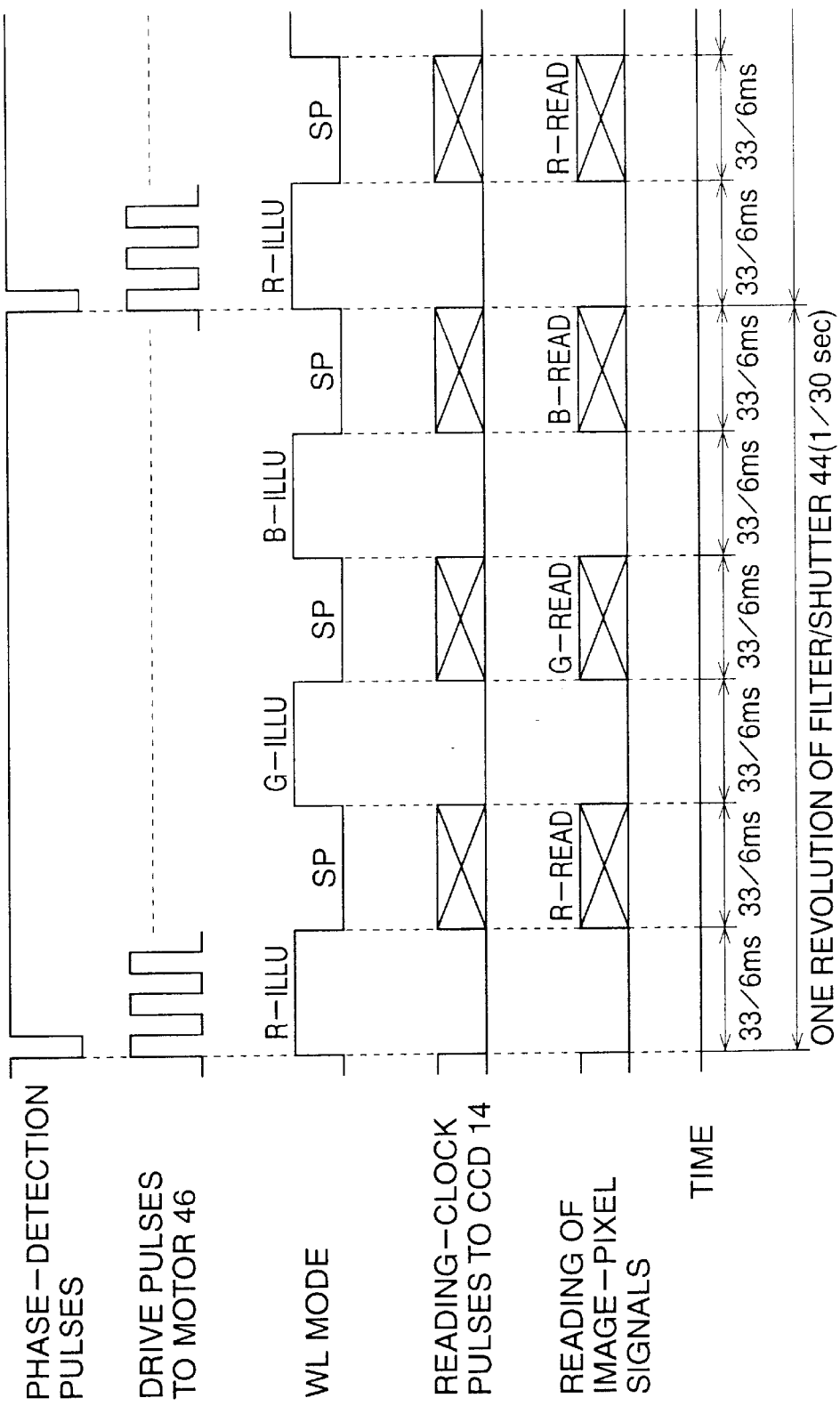
FIG. 10 is a timing chart showing a reading of image-pixel signals from a CCD image sensor in a white light illumination mode.

FIG. 10 shows a timing chart of the reading of the image-pixel signals from the CCD image sensor 14 when the WL illumination mode is selected. As is apparent from this timing chart, the drive pulses for driving the motor 46 are output from the driver circuit 76 such that the phase of the drive pulse coincides with the phase of a phase-detection pulse output from the PD of the phase detector 78, every revolution of the rotary color-filter/shutter 44.

In the timing chart of FIG. 10, a red-light illumination period, during which the red light radiates from the distal end of the optical light guide 18, is indicated by reference "R-ILLU"; a green-light illumination period, during which the green light radiates from the distal end of the optical light guide 18, is indicated by reference "G-ILLU"; a blue-light illumination period, during which the blue light radiates from the distal end of the optical light guide 18, is indicated by reference "B-ILLU"; and a shield period, during which no light radiates from the distal end of the optical light guide 18, is indicated by reference "SP".

As shown in the timing chart of FIG. 10, during each shield period "SP", the series of reading-clock pulses is output from the CCD driver 54 to the CCD image sensor 14 in accordance with the timing-clock pulses output from the timing controller 74 to the CCD driver 54, and a frame of monochromatic (red, green, blue) image-pixel signals is read from the CCD image sensor 14 in accordance with the series of reading-clock pulses. Note, in the timing chart of FIG. 10, a reading period of red image-pixel signals is indicated by reference "R-READ"; a reading period of green image-pixel signals is indicated by reference "G-READ"; and a reading period of blue image-pixel signals is indicated by reference "B-READ".

Figure 11:
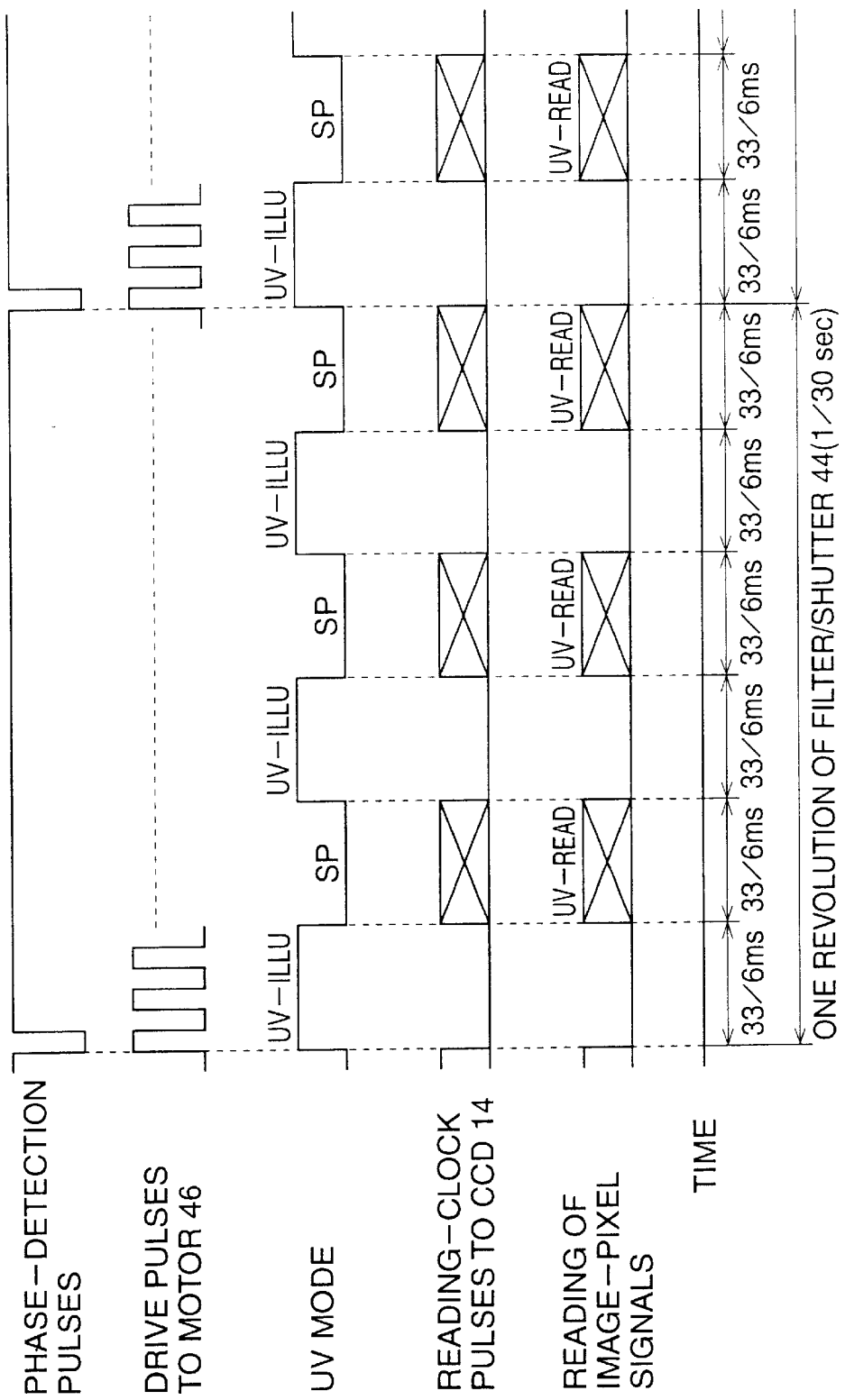
FIG. 11 is a timing chart showing a reading of image-pixel signals from the CCD image sensor in an ultraviolet light illumination mode.

FIG. 11 shows a timing chart of the reading of the image-pixel signals from the CCD image sensor 14 when the UV illumination mode is selected. Similar to the timing chart (WL illumination mode) of FIG. 10, the drive pulses for driving the motor 46 are output from the driver circuit 76 such that a phase of the drive pulse coincides with a phase of a phase-detection pulse output from the PD of the phase detector 78 every revolution of the rotary color-filter/shutter 44.

In the timing chart of FIG. 11, a UV-light illumination period, during which the UV light radiates from the distal end of the optical light guide 18, is indicated by reference "UV-ILLU", and the radiation of the UV light is performed three times during every revolution of the rotary color-filter/shutter 44. Note, a shield period, during which no UV light radiates from the distal end of the optical light guide 18, is indicated by reference "SP".

As shown in the timing chart of FIG. 11, during each shield period "SP", the series of reading-clock pulses is output from the CCD driver 54 to the CCD image sensor 14 in accordance with the timing-clock pulses, output from the timing controller 74 to the CCD driver 54, and a frame of monochromatic fluorescent image-pixel signals is read from the CCD image sensor 14 in accordance with the series of reading-clock pulses. Note, in the timing chart, a reading period of image-pixel signals is indicated by reference "UV-READ".

Of course, the reading of image-pixel signals is performed three times during every revolution of the rotary color-filter/shutter 44, and the three frames of image-pixel signals, read from the CCD image sensor 14, are successively stored as three frames of digital image-pixel signals in the frame memories 66R, 66G and 66B, respectively.

As shown in FIG. 1, the WL lamp 24 is electrically energized by an electric power circuit 82, and a power supply to the WL lamp 24 from the electric power circuit 82 is controlled by the system controller 72. In this embodiment, the WL lamp 24 cannot only be turned ON and OFF but also controlled to vary the amount of light-emission of the WL lamp 24, if necessary. The UV lamp 26 is electrically energized by an electric power circuit 84, and a power supply to the UV lamp 26 from the electric power circuit 86 is controlled by the system controller 72. Similar to the WL lamp 24, the UV lamp 26 cannot only be turned ON and OFF but also controlled to vary the amount of light-emission of the UV lamp 26, if necessary.

Usually, when the WL illumination mode is selected, only the WL lamp 24 is turned ON, and the UV lamp 26 is turned OFF. On the other hand, when the UV illumination mode is selected, only the UV lamp 2.6 is turned ON, and the WL lamp 24 is turned OFF.

However, when the WL illumination mode is switched to the UV illumination mode and vice versa at frequent intervals, e.g. when an endoscope-image, based on the WL light illumination, and an endoscope-image, based on the UV light illumination, are repeatedly compared with each other during a medical examination, it is preferable not to completely turn OFF each of the WL and UV lamps 24 and 26, because the service life of each lamp (24, 26) is significantly shortened by turning ON and OFF them at frequent intervals, and because the light-emission from each lamp (24, 26) is unstable immediately after being turned ON. Thus, while one of the WL and UV lamps 24 and 26 is turned ON, the amount of light-emission from the other lamp should be reduced rather than being turned OFF.

In FIG. 1, reference 86 indicates a driver circuit which drives an actuator 42 for the diaphragm 40, and the driver circuit 86 is operated under control of the system controller 72. The initial processing circuit 62 (FIG. 9) includes an integrating circuit for integrating signal levels of the image-pixel signals included in each frame, and the integrated result is utilized to control an aperture of the diaphragm 40. Namely, the diaphragm 40 is operated by driving the actuator 42 in accordance with the integrated result under control of the system controller 72, so that a constant overall brightness of a reproduced endoscope-image on the TV monitor 58 can be maintained.

In FIG. 1, reference 88 indicates a front panel provided on a housing of the image-signal processing unit 12, and the front panel 88 includes various switches. Switches, which especially relate to the present invention, are a power ON/OFF switch 90, a lamp ON/OFF switch 92, an illumination-mode selection switch 94 and an OFF/reduction-mode selection switch 96.

When the power ON/OFF switch 90 is turned ON, a power source circuit (not shown) of the signal-processing unit 12 is supplied with electric power from a commercial power network.

The lamp ON/OFF switch 92 is common to both the WL and UV lamps 24 and 26, and does not directly and separately control turn-ON and turn-OFF of the lamps 24 and 26. Namely, when the lamp ON/OFF switch 92 is in an OFF-state, both the lamps 24 and 26 are prohibited from being lit, and, when the lamp ON/OFF switch 92 is turned ON, both the lamps 24 and 26 are allowed to be lit. Note, the turn-ON and the turn-OFF of each lamp (24, 26) are controlled as stated in detail hereinafter.

The illumination-mode selection switch 94 is provided for selecting either the WL illumination mode or the TV illumination mode. The illumination-mode selection switch 94 is constituted to alternately output a high level signal or a low level signal to the system controller whenever it is depressed. When the high level signal is output from the illumination-mode selection switch 94, the system controller 72 recognizes that the WL illumination mode is selected. When the low level signal is output from the illumination-mode selection switch 94, the system controller 72 recognizes that the UV illumination mode is selected. Namely, whenever the illumination-mode selection switch 94 is depressed, the WL and UV illumination modes are alternately selected. Note, when the power ON/OFF switch 90 is turned ON, the high level signal is output from the illumination-mode selection switch 94, and the WL illumination mode is forcibly selected as the initial illumination mode.

The OFF/reduction-mode selection switch 96 is provided for selecting either an OFF mode or an illumination reduction mode. When one of the WL and UV illumination modes is selected, it is determined by the OFF/reduction-mode selection switch 96 whether a lamp (24, 26) used in the non-selected illumination mode should be completely turned OFF or the amount of light-emission therefrom should be reduced. Of course, when the OFF mode is selected, the lamp (24, 26) concerned is completely turned OFF, and when the illumination reduction mode is selected, the amount of light-emission from the lamp (24, 26) concerned is reduced.

Similar to the illumination-mode selection switch 94, the OFF/reduction-mode selection switch 96 alternately outputs a high level signal or a low level signal to the system controller whenever it is depressed. When the high level signal is output from the OFF/reduction-mode selection switch 96, the system controller 72 recognizes that the OFF mode is selected. When the low level signal is output from the OFF/reduction-mode selection switch 96, the system controller 72 recognizes that the illumination reduction mode is selected. Namely, whenever the OFF/reduction-mode selection switch 96 is depressed, the OFF mode and the illumination reduction mode are alternately selected. Note, when the power ON/OFF switch 90 is turned ON, the high level signal is output from the OFF/reduction-mode selection switch 96, whereby the OFF mode is initially selected.

As shown in FIG. 1, a keyboard 98 is connected to the system control 72 of the image-signal processing unit 12 to input various commands and various data to the system controller 72. Respective functions, pertaining to the illumination-mode selection switch 94 and the OFF/reduction-mode selection switch 96, may be allocated to two function keys on the keyboard 98. When the illumination-mode selection and the OFF/reduction-mode selection are performed by the function keys on the keyboard 98, the illumination-mode selection switch 94 and the OFF/reduction-mode selection switch 96 may be eliminated from the front panel 88.

Figure 12:
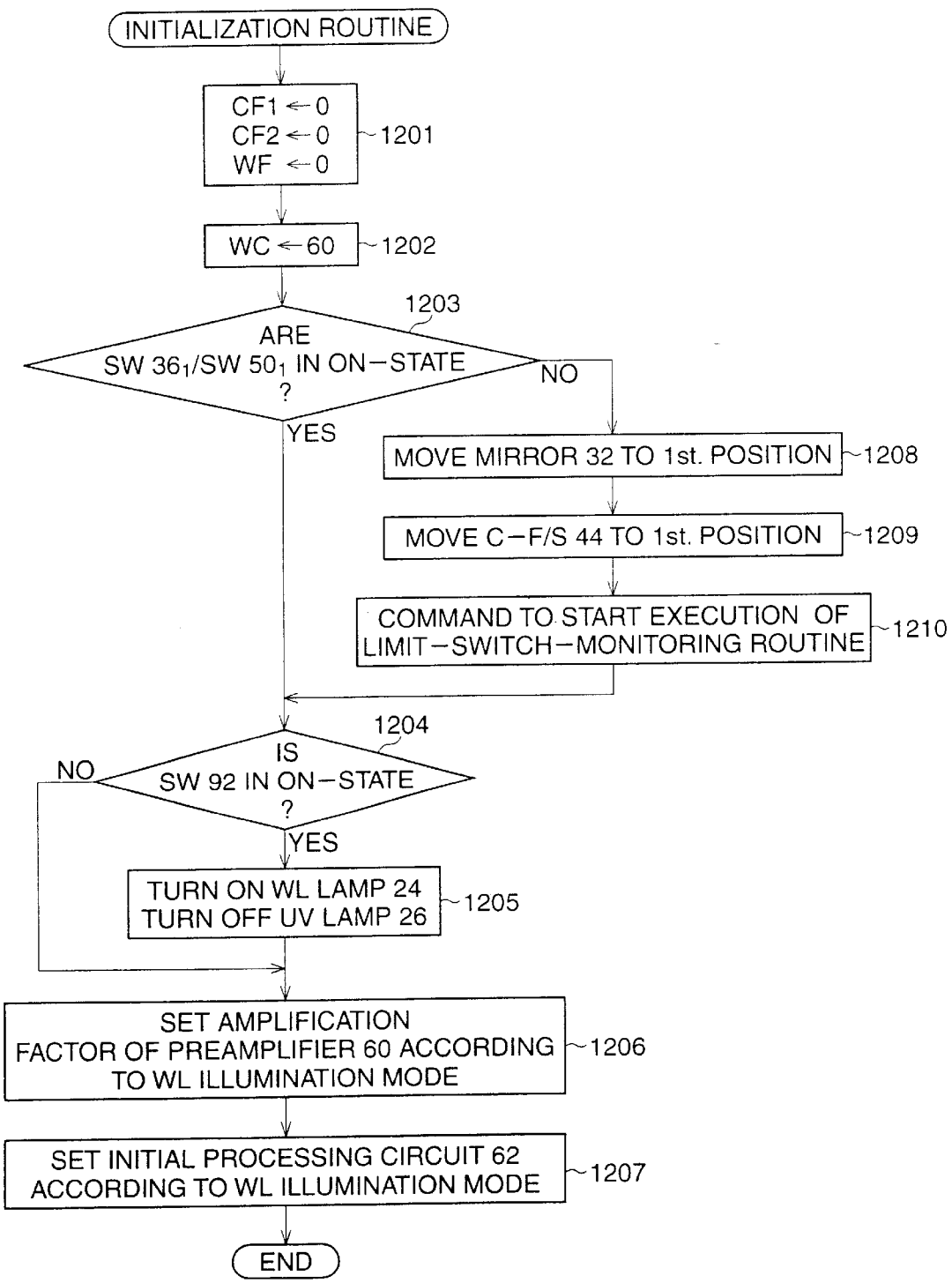
FIG. 12 is a flowchart of an initialization routine.

FIG. 12 shows a flowchart of an initialization routine which is only executed once by the system controller 72, when the power ON/OFF switch 90 is turned ON.

At step 1201, an illumination-mode-indication flag CF1, an OFF/reduction-mode-indication flag CF2 and a standby-indication flag WF are initialized to "0".

The illumination-mode-indication flag CF1 is provided to indicate whether the WL illumination mode or the UV illumination mode is selected. If CF1=0, the flag CF1 indicates that the WL illumination mode is selected. If CF1=1, the flag CF1 indicates that the UV illumination mode is selected. As stated above, at the initial stage, since the WL illumination mode is forcibly selected, the flag CF1 is initialized to "0".

The OFF/reduction-mode-indication flag CF2 is provided to indicate whether the OFF mode or the illumination reduction mode is selected. If CF2=0, the flag CF2 indicates that the OFF mode is selected. If CF2=1, the flag CF2 indicates that the illumination reduction mode is selected. As stated above, at the initial stage, since the OFF mode is forcibly selected, the flag CF2 is initialized to "0".

The standby-indication flag WF is provided to indicate whether switching the WL illumination mode to the UV illumination mode, and vice versa, has been completed when the illumination-mode selection switch 94 is operated.

In particular, whenever the illumination-mode selection switch 94 is depressed, the flag WF is set to "1", thereby disabling the illumination-mode selection switch 94. Thereafter, it is monitored whether a time period of, for example, 3 sec has elapsed since the flag WF is set to "1". During the elapse of the time period of 3 sec, the movement of the mirror 32 from the first operative position (FIG. 2) to the second operative position (FIG. 3) and vice versa, as well as the movement of the rotary color-filter/shutter 44 from the first operative position (FIG. 2) to the second operative position (FIG. 3) and vice versa are completed. As soon as it is confirmed that the time period of 3 sec has elapsed, the flag WF is reset to "0", thereby enabling the illumination-mode selection switch 94.

At step 1202, a standby-time counter WC is initialized to "60". Note, the standby-time counter WC is provided for counting the aforementioned time period of 3 sec, as stated hereinafter.

At step 1203, it is determined whether both the first limit switch $36_1$ of the driving-mechanism 34 for the mirror 32 and the first limit switch $50_1$ of the driving-mechanism 48 for the rotary color-filter/shutter 44 are in an ON-state, i.e. whether the mirror 32 and the rotary color-filter/shutter 44 are positioned at the respective first operative positions (FIG. 2).

If both the limit switches $36_1$ and $50_1$ are in the ON-state, the control proceeds to step 1204, in which it is determined whether the lamp ON/OFF switch 92 is turned ON. If the lamp ON/OFF switch 92 is in an ON-state, the control proceeds to step 1205, in which the WL lamp 24 is turned ON and the UV lamp 26 is turned OFF, as the flags CF1 and CF2 are "0".

At step 1206, the amplification factor of the preamplifier 60 is set in accordance with the WL illumination mode. Then, at step 1207, the initial processing circuit 62 is set in accordance with the WL illumination mode, and the initialization routine ends.

At step 1204, if the lamp ON/OFF switch 92 is in an OFF-state, the control skips step 1205 to step 1206. In this case, the lighting of the WL and UV lamps 24 and 26 is controlled in accordance with a lamp-ON/OFF-switch-monitoring routine after the initialization routine ends. Note, the lamp-ON/OFF-switch-monitoring routine is explained in detail hereinafter with reference to FIG. 13.

At step 1203, when both the limit switches 36$_1$ and 50$_1$ are in an OFF-state, i.e. when both the mirror 32 and the rotary color-filter/shutter 44 are not positioned at the respective first operative positions, the control proceeds to step 1208, in which the motor 34d is driven such that the mirror 32 is moved to the first operative position. Subsequently, at step 1209, the motor 48d is driven such that the rotary color-filter/shutter 44 is moved to the first operative position. Then, at step 1210, starting execution of a limit-switch-monitoring routine is commanded. Thereafter, the control proceeds to step 1204. Note, the limit-switch-monitoring routine is explained in detail hereinafter with reference to FIG. 17.

Figure 13:
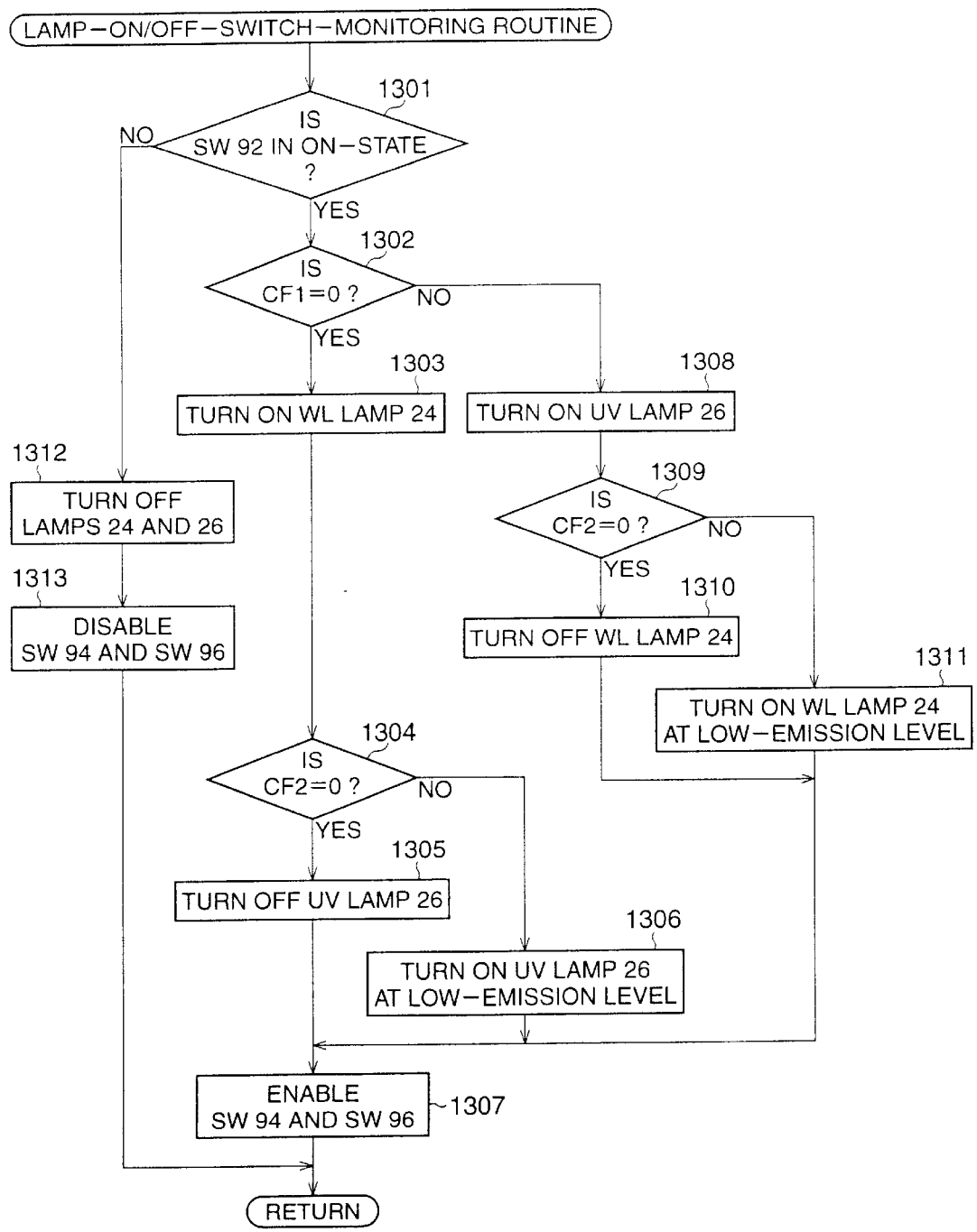
FIG. 13 is a flowchart of a lamp-ON/OFF-switch-monitoring routine.

FIG. 13 is a flowchart of the aforesaid lamp-ON/OFF-switch-monitoring routine, which is formed as a time-interruption routine executed in the system controller 72 at regular suitable intervals of, for example, 50 ms. Note that the execution of the lamp-ON/OFF-switch-monitoring routine is consecutive to the initialization routine of FIG. 12, and is repeated every 50 ms as long as the power ON/OFF switch 90 is turned ON.

At step 1301, the lamp ON/OFF switch 92 is monitored every 50 ms. When it is confirmed that the lamp ON/OFF switch 92 is in an ON-state, the control proceeds to step 1302, in which it is determined whether the illumination-mode-indication flag CF1 is "0" or "1". If CF1=0, i.e. if the WL illumination mode is selected, the control proceeds to step 1303, in which the WL lamp 24 is turned ON.

At step 1304, it is determined whether the OFF/reduction-mode-indication flag CF2 is "0" or "1". If CF2=0, i.e. if the OFF mode is selected, the control proceeds to step 1305, in which the UV lamp 26 is turned OFF. At step 1304, if CF2=1, i.e. if the illumination reduction mode is selected, the control proceeds to step 1306, in which the UV lamp 26 is turned ON at a low-light-emission level, whereby the UV lamp 26 is lit such that the amount of light-emission therefrom is reduced.

At step 1307, the illumination-mode selection switch 94, OFF/reduction-mode selection switch 96 and the corresponding function keys on the keyboard 98, are enabled. Namely, it is possible to select either the WL illumination mode or the UV illumination mode and either the OFF mode or the illumination reduction mode only while the lamp ON/OFF switch 92 is in the ON-state.

At step 1302, if CF1=1, i.e. if the UV illumination mode is selected, the control proceeds to step 1308 in which the UV lamp 26 is turned ON.

At step 1309 it is determined whether the flag CF2 is "0" or "1". If CF2=0, i.e. if the OFF mode is selected, the control proceeds to step 1310, in which the WL lamp 24 is turned OFF. At step 1309, if CF2=1, i.e. if the illumination reduction mode is selected, the control proceeds to step 1311, in which the WL lamp 24 is turned ON at a low-light-emission level, whereby the WL lamp 24 is lit such that the amount of light-emission therefrom is reduced.

At step 1301, when it is confirmed that the lamp ON/OFF switch 92 is in an OFF-state, the control proceeds to step 1312, in which the WL and UV lamps 24 and 26 are turned OFF. Namely, while the lamp ON/OFF switch 92 is in the OFF-state, both the lamps 24 and 26 are prohibited from being lit, as stated above.

At step 1313, the illumination-mode selection switch 94, the OFF/reduction-mode selection switch 96 and the corresponding function keys on the keyboard 98, are disabled. Namely, it is impossible to select either the WL illumination mode or the UV illumination mode and either the OFF mode or the illumination reduction mode only while the lamp ON/OFF switch 92 is in the OFF-state.

Figure 14:
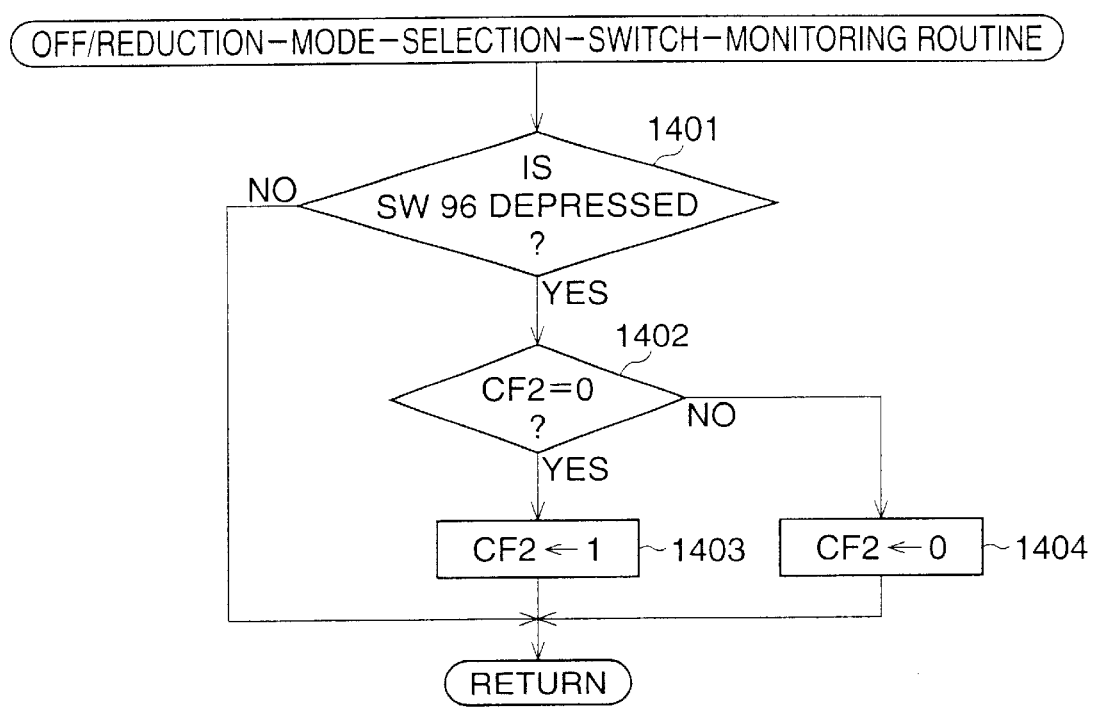
FIG. 14 is a flowchart of an OFF/reduction-mode-selection-switch-monitoring routine.

FIG. 14 is a flowchart of an OFF/reduction-mode-selection-switch-monitoring routine, which is formed as a time-interruption routine executed in the system controller 72 at regular suitable intervals of, for example, 50 ms. Note that the execution of the OFF/reduction-mode-selection-switch-monitoring routine is consecutive to the initialization routine of FIG. 12, and is repeated every 50 ms as long as the power ON/OFF switch 90 is turned ON.

At step 1401, the OFF/reduction-mode selection switch 96, or the corresponding function key on the keyboard 98, is monitored for depression. If depression of either the OFF/reduction-mode selection switch 96 or the corresponding function key is not detected, the routine immediately ends. Although the routine is repeatedly executed every 50 ms, there in no progress until depression of either the OFF/reduction-mode selection switch 96 or the corresponding function key is confirmed.

At step 1401, when depression of either the OFF/reduction-mode selection switch 96 or the corresponding function key is confirmed, the control proceeds to step 1402, in which it is determined whether the OFF/reduction-mode-indication flag CF2 is "0" or "1".

If CF2=0, i.e. if the OFF mode is selected, the control proceeds to step 1403, in which the flag CF2 is set to "1", thereby indicating that the illumination reduction mode is selected.

At step 1402, if CF2=1, i.e. if the illumination reduction mode is selected, the control proceeds from step 1402 to step 1404, in which the flag CF2 is set to "0", thereby indicating that the OFF mode is selected.

Figure 15:
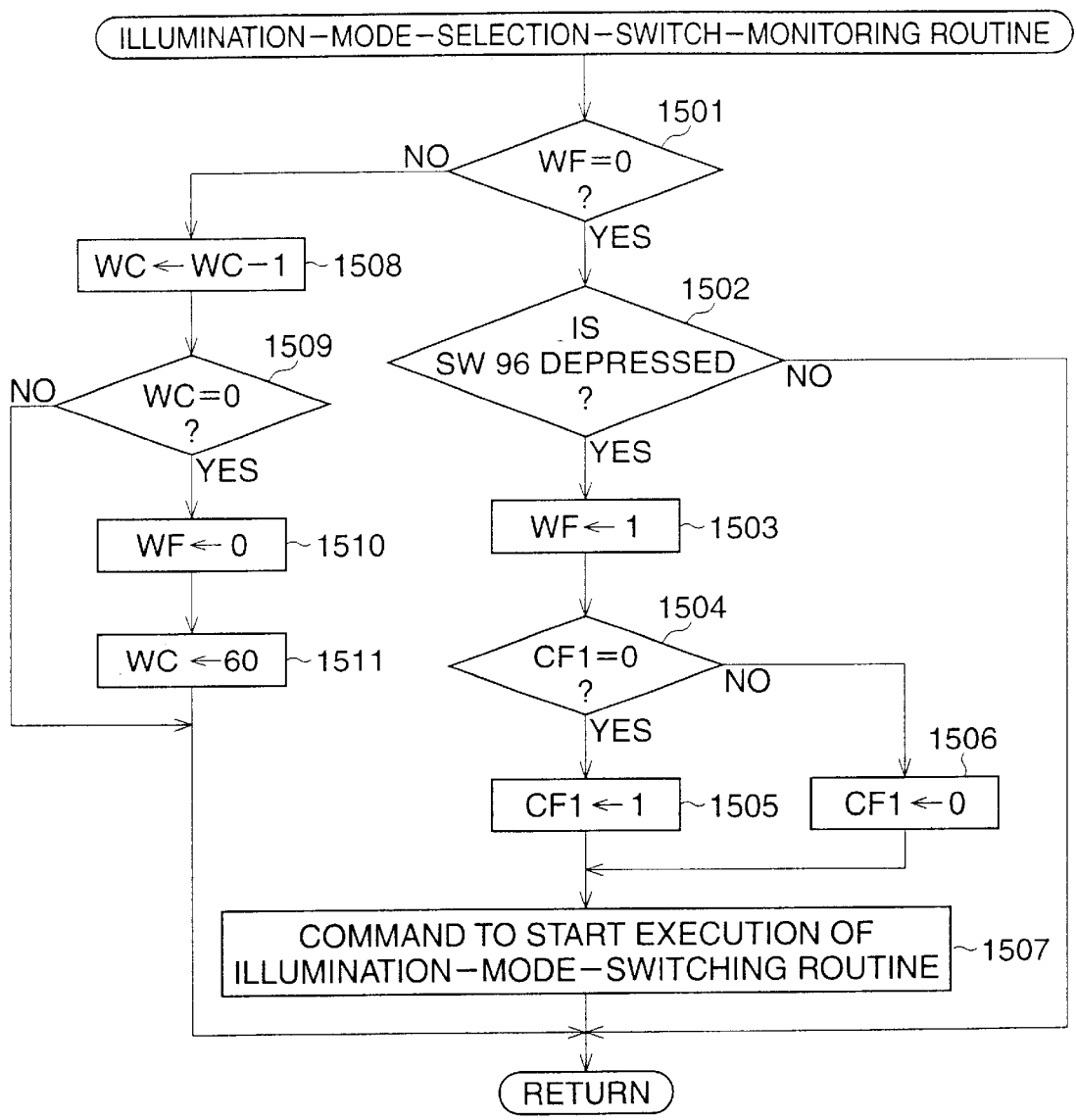
FIG. 15 is a flowchart of an illumination-mode-selection-switch-monitoring routine.

FIG. 15 is a flowchart of an illumination-mode-selection-switch-monitoring routine, which is formed as a time-interruption routine executed in the system controller 72 at regular suitable intervals of, for example, 50 ms. Note that the execution of the illumination-mode-selection-switch-monitoring routine is consecutive to the initialization routine of FIG. 12, and is repeated every 50 ms as long as the power ON/OFF switch 90 is turned ON.

At step 1501, it is determined whether the standby-indication flag WF is "0" or "1". At the initial stage, since WF =0 (step 1201), the control proceeds to step 1502, in which the illumination-mode selection switch 94, or the corresponding function key on the keyboard 98, is monitored for depression. If depression of either the OFF/reduction-mode selection switch 96 or the corresponding function key is not detected, the routine immediately ends. Although the routine is repeatedly executed every 50 ms, there in no progress until depression of either the illumination-mode selection switch 94 or the corresponding function key is confirmed.

At step 1502, when depression of either the illumination-mode selection switch 96 or the corresponding function key is confirmed, the control proceeds to step 1503, in which the standby-indication flag WF is set to "1". Then, at step 1504, it is determined whether the illumination-mode-indication flag CF1 is "0" or "1"

If CF1=0, i.e. if the WL illumination mode is selected, the control proceeds to step 1505, in which the flag CF1 is set to "1", thereby indicating that the UV illumination mode is selected.

At step 1504, if CF1=1, i.e. if the UV illumination mode is selected, the control proceeds from step 1504 to step 1506, in which the flag CF1 is set to "0", thereby indicating that the WL illumination-mode is selected.

In either case, at step 1507, starting execution of an illumination-mode-switching routine is commanded, and the routine ends. Note, the illumination-mode-switching routine is explained in detail hereinafter with reference to FIG. 16.

After the setting of "1" is given to the flag WF (step 1503), the control proceeds from step 1501 to step 1508 (WF=1), in which the value of the standby-time counter WC, which has a setting of "60" as the initial value (step 1202), is decremented by "1". Then, at step 1509, it is determined whether the value of the counter WC has reached "0". If WC>0, the control skips steps 1510 and 1511, and thus the routine ends. Thereafter, although the routine is repeatedly executed every 50 ms, there is no progress until the counter WC reaches "0".

At step 1509, when it is confirmed that the value of the counter WC has reached "0", i.e. when it is confirmed that a time period of 3 sec (50 ms×60) has elapsed, the control proceeds from step 1509 to step 1510, in which the standby-indication flag WF is set to "0". Then, at step 1511, the standby-time counter WC is reset to "60", and the routine ends.

In short, during the elapse of the 3 sec time period, the illumination-mode-switching routine (FIG. 16) is executed (step 1507). Namely, the 3 sec time period is enough to complete the switching of the WL illumination mode to the UV illumination mode and vice versa.

Figure 16:
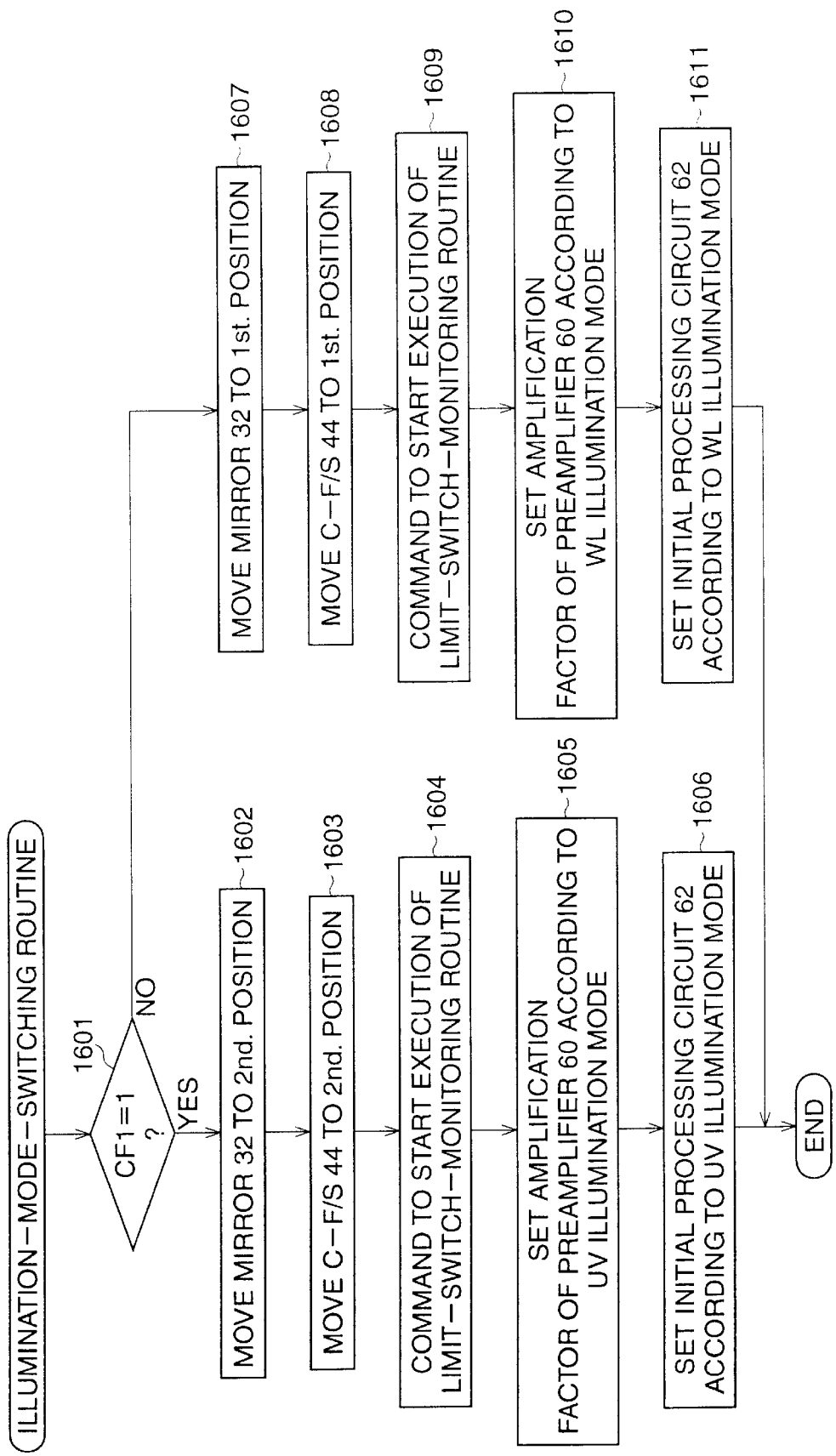
FIG. 16 is a flowchart of an illumination-mode-switching routine.

FIG. 16 is a flowchart of the aforesaid illumination-mode-switching routine, which is executed in the system controller 72 after being commanded at step 1507 of FIG. 15.

At step 1601, it is determined whether the illumination-mode-indication flag CF1 is "1" or "0". If CF1=1, i.e. if the selection of the UV illumination mode has been confirmed, the control proceeds to step 1602, in which the motor 34d is driven such that the mirror 32 is moved from the first operative position to the second operative position. Subsequently, at step 1603, the motor 48d is driven such that the rotary color-filter/shutter 44 is moved from the first operative position to the second operative position. Then, at step 1604, starting execution of the limit-switch-monitoring routine (FIG. 17) is commanded.

At step 1605, the amplification factor of the preamplifier 60 is set in accordance with the UV illumination mode. Then, at step 1606, the initial processing circuit 62 is set in accordance with the UV illumination mode, and the routine ends.

On the other hand, at step 1601, if CF1=0, i.e. if selection of the WL illumination mode has been confirmed, the control proceeds from step 1601 to step 1607, in which the motor 34d is driven such that the mirror 32 is moved from the second operative position to the first operative position. Subsequently, at step 1608, the motor 48d is driven such that the rotary color-filter/shutter 44 is moved from the second operative position to first operative position. Then, at step 1609, starting execution of the limit-switch-monitoring routine (FIG. 17) is commanded.

At step 1610, the amplification factor of the preamplifier 60 is set in accordance with the WL illumination mode.

Then, at step 1611, the initial processing circuit 62 is set in accordance with the WL illumination mode, and the routine ends.

Figure 17:
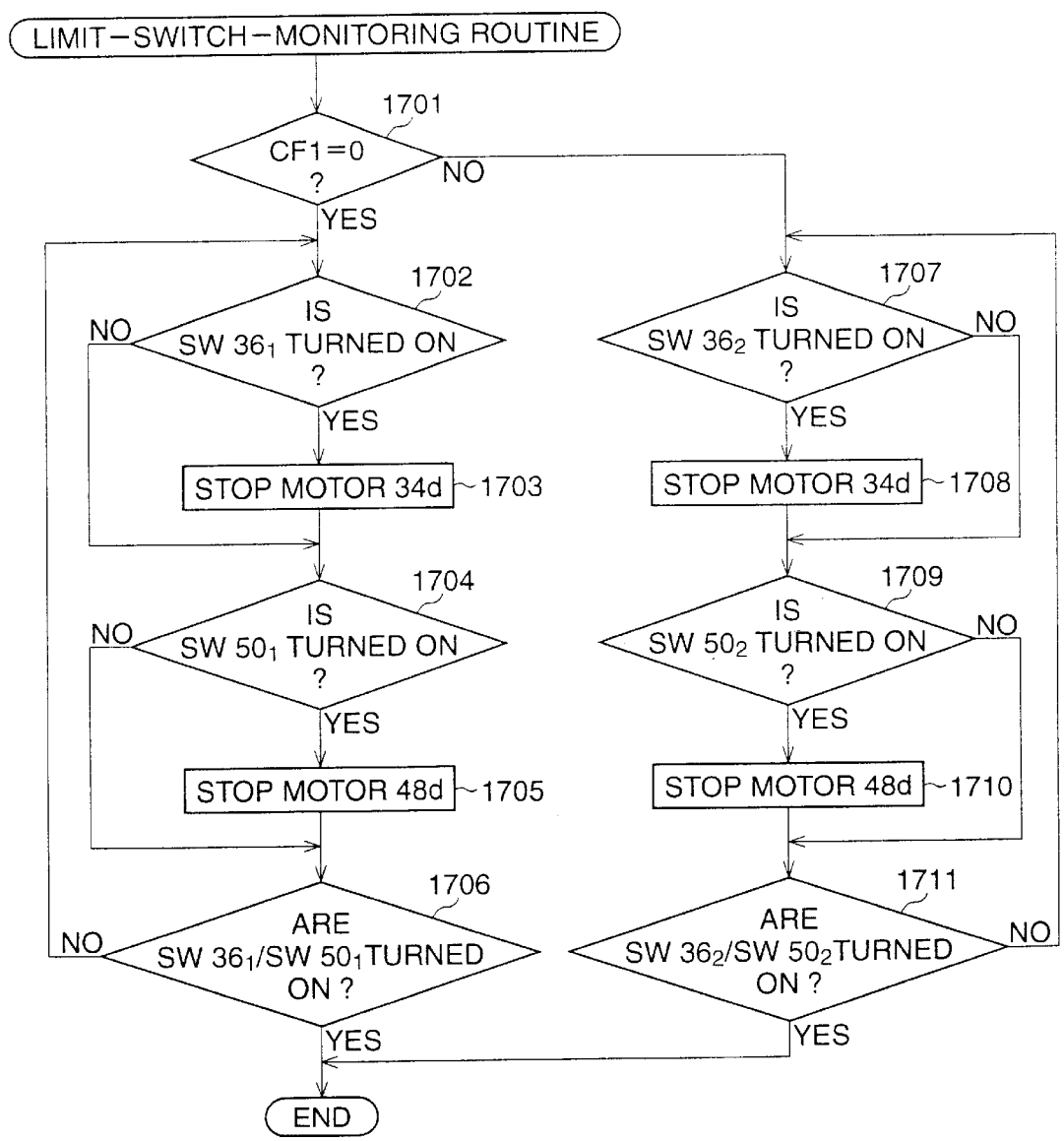
FIG. 17 is a flowchart of an illumination-mode-switching routine.

FIG. 17 is a flowchart of the aforesaid limit-switch-monitoring routine, which is executed in the system controller 72 after being commanded at either step 1210 of FIG. 12, step 1606 or step 1611 of FIG. 15.

At step 1701, it is determined whether the illumination-mode-indication flag CF1 is "0" or "1". If CF1=0, i.e. if the WL illumination mode is selected, the control proceeds to step 1702, in which it is determined whether the limit switch $36_1$ has been turned ON. If the limit switch $36_1$ is in the OFF-state, the control skips step 1703 to step 1704, in which it is determined whether the limit switch $50_1$ has been turned ON. If the limit switch $50_1$ is in the OFF-state, the control skips step 1705 to step 1706, in which it is determined whether both the limit switches $36_1$ and $50_1$ are in the ON-state. Even if only one of the limit switches $36_1$ and $50_1$ is in the OFF-state, the control returns to step 1702.

At step 1702, when it is confirmed that the limit switch $36_1$ has been turned ON, the control proceeds to step 1703, in which the motor 34d is stopped, thereby positioning the mirror 32 at the first operative position. Also, at step 1704, when it is confirmed that the limit switch $50_1$ has been turned ON, the control proceeds to step 1705, in which the motor 48d is stopped, thereby positioning the rotary color-filter/shutter 44 at the first operative position.

At step 1706, when it is confirmed that both the limit switches $36_1$ and $50_1$ are in the ON-state, the limit-switch-monitoring routine ends.

On the other hand, at step 1701, if CF1=0, i.e. if the UV illumination mode is selected, the control proceeds from step 1701 to step 1707, in which it is determined whether the limit switch $36_2$ has been turned ON. If the limit switch $36_2$ is in the OFF-state, the control skips step 1708 to step 1709, in which it is determined whether the limit switch $50_2$ has been turned ON. If the limit switch $50_2$ is in the OFF-state, the control skips step 1710 to step 1711, in which it is determined whether both the limit switches $36_2$ and $50_2$ are in the ON-state. Even if only one of the limit switches $36_2$ and $50_2$ is in the OFF-state, the control returns to step 1707.

At step 1707, when it is confirmed that the limit switch $36_2$ has been turned ON, the control proceeds to step 1708, in which the motor 34d is stopped, thereby positioning the mirror 32 at the second operative position. Also, at step 1709, when it is confirmed that the limit switch $50_1$ has been turned ON, the control proceeds to step 1710, in which the motor 48d is stopped, thereby positioning the rotary color-filter/shutter 44 at the second operative position.

At step 1711, when it is confirmed that both the limit switches $36_2$ and $50_2$ are in the ON-state, the limit-switch-monitoring routine ends.

Note, in the limit-switch-monitoring routine shown in FIG. 17, the routine comprising steps 1702 to 1706, and the routine comprising 1707 to 1711, are repeatedly executed in suitable regular intervals of, for example, 50 ms.

Figure 18:
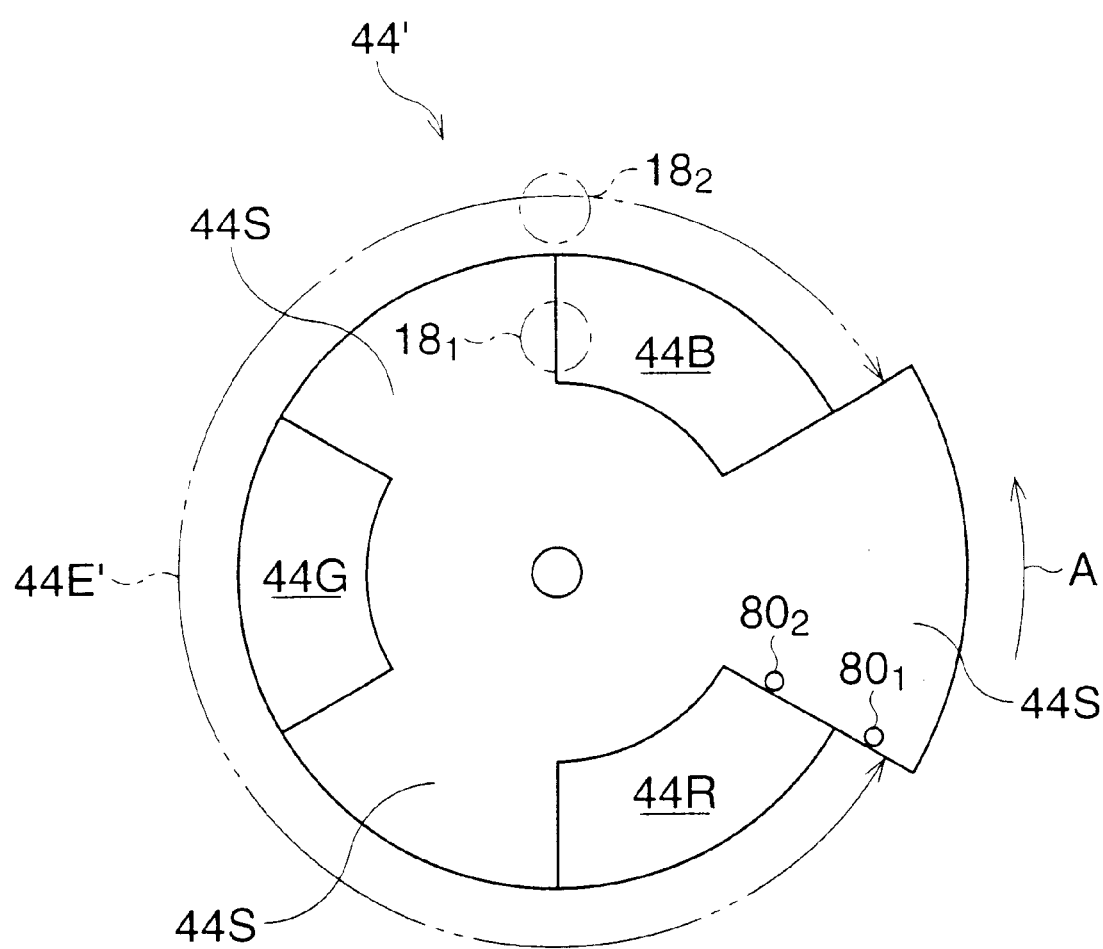
FIG. 18 is a plan view showing a modification of the rotary color-filter/shutter of FIG. 6.

FIG. 18 shows a modification of the rotary color-filter/shutter 44, generally indicated by reference 44'. Note, in this drawing, the features similar to those of FIG. 6 are indicated by the same references.

In the modified rotary color-filter/shutter 44', only one of the light-shielding areas 44S, positioned between the red and blue filters 44R and 44B, is radially and outwardly extended, and an opening or exposure area 44E' is defined as an area between the radial edges of the extended light-shielding area 44S, as indicated by an arrow-headed double-dot-chain line in FIG. 18.

When the modified rotary color-filter/shutter 44' is substituted for the rotary color-filter/shutter 44 in the light source device 19, it functions as the rotary RGB color filter in the WL illumination mode in substantially the same manner as the rotary color-filter/shutter 44. Thus, in the WL illumination mode, three frames of red, green, blue image-pixel signals are read from the CCD image sensor 14, as shown in the timing chart of FIG. 10.

On the other hand, when the UV illumination mode is selected, i.e. when the modified rotary color-filter/shutter 44' is positioned at the second operative position, the rotary color-filter/shutter 44' functions as the rotary shutter. In this case, a frame of monochromatic fluorescent image-pixel signals is read from the CCD image sensor 14 in accordance with a timing chart shown in FIG. 19.

Figure 19:
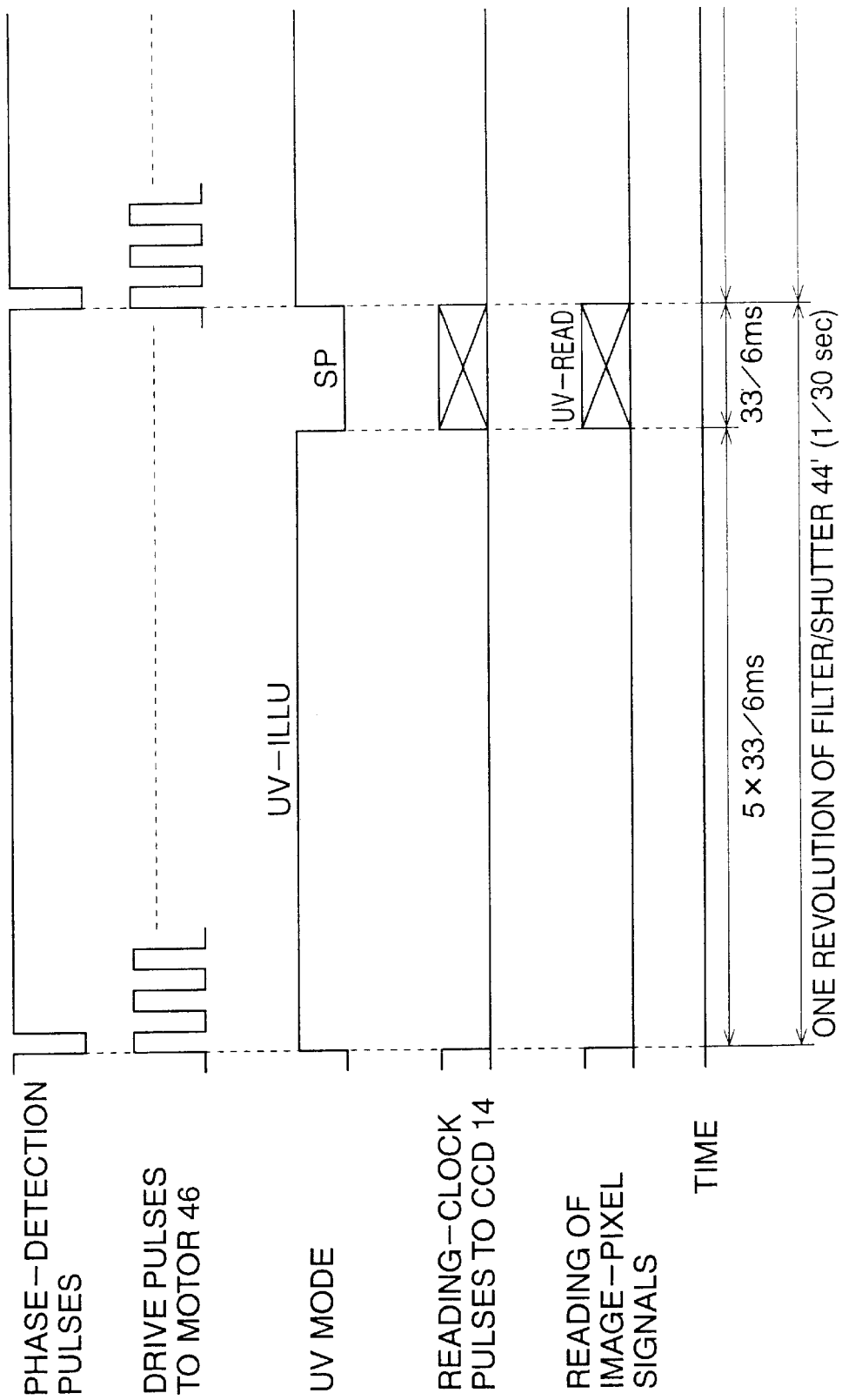
FIG. 19 is a timing chart showing a reading of image-pixel signals from the CCD image sensor in the ultraviolet light illumination mode when using the modified rotary color-filter/shutter of FIG. 18.

In particular, as is apparent from the timing chart of FIG. 19, the UV-light illumination period "UV-ILLU", during which the UV light radiates from the distal end of the optical light guide 18, is substantially extended, and the radiation of UV light is performed once every revolution of the modified rotary color-filter/shutter 44'. The UV-light illumination period, obtained by the modified rotary color-filter/shutter 44', corresponds to the exposure area 44E', and is five times as long as that obtained by the aforesaid rotary color-filter/shutter 44. Thus, a frame of monochromatic fluorescent image-pixel signals is read from the CCD image sensor 14 over a shield period "SP", consecutive to the extended UV-light illumination period "UV-ILLU". Namely, the reading of monochromatic fluorescent image-pixel signals is performed over a reading period "UV-READ", which coincide-s with the shield period "SP".

In short, in a case where the modified rotary color-filter/shutter 44' is substituted for the rotary color-filter/shutter 44, in the UV illumination mode, the series of reading-clock pulses must be output from to the CCD driver 54 to the CCD image sensor 14 in accordance with the timing chart of FIG. 19.

Note, in the timing chart of FIG. 19, the drive pulses for driving the motor 46 are output from the driver circuit 76 such that a phase of the drive pulse coincides with a phase of a phase-detection pulse, output from the photodiode (PD) of the phase detector 78, every revolution of the modified rotary color-filter/shutter 44'.

As is apparent from a comparison between the timing chart of FIG. 19 and the timing chart of FIG. 10, since the timing of the reading of fluorescent image-pixel signals (FIG. 19) from the CCD image sensor 14 coincide-s with the timing of the reading of blue image-pixel signals (FIG. 10) from the CCD image sensor 14, the read fluorescent image-pixel signals can be processed in substantially the same manner as the blue image-pixel signals, read from the CCD image sensor 14 when the WL illumination mode is selected. Accordingly, after the fluorescent image-pixel signals are converted by the A/D converter 64 into digital fluorescent image-pixel signals, these digital fluorescent image-pixel signals are stored in the frame memory 66B. Therefore, in the UV illumination mode, a fluorescent endoscope-image is reproduced and displayed on the TV monitor 58 on the basis of a video signal component output from the final processing circuit 70B. In short, by operating the image-signal processing circuit 56 in the same manner as in the WL illumination mode, it is possible to reproduce and display the fluorescent endoscope-image on the TV monitor 58.

Of course, in the UV illumination mode using the modified rotary color-filter/shutter 44', a video signal component is also output from each of the final processing circuits 70R and 70G, because the image-signal processing circuit 58 is operated in the same manner as in the WL illumination mode. However, the video signal components, output from the final processing circuits 70R and 70G, are unsubstantial. Thus, the unsubstantial video signal components are omitted, and cannot be utilized during the reproduction of the fluorescent endoscope-image on the TV monitor 58.

When the modified rotary color-filter/shutter 44' is used in the light source device 19, it is necessary to partially modify the initialization routine of FIG. 12 and the illumination-mode-switching routine of FIG. 16, before the image-signal processing unit 12 can be properly operated.

Figure 20:
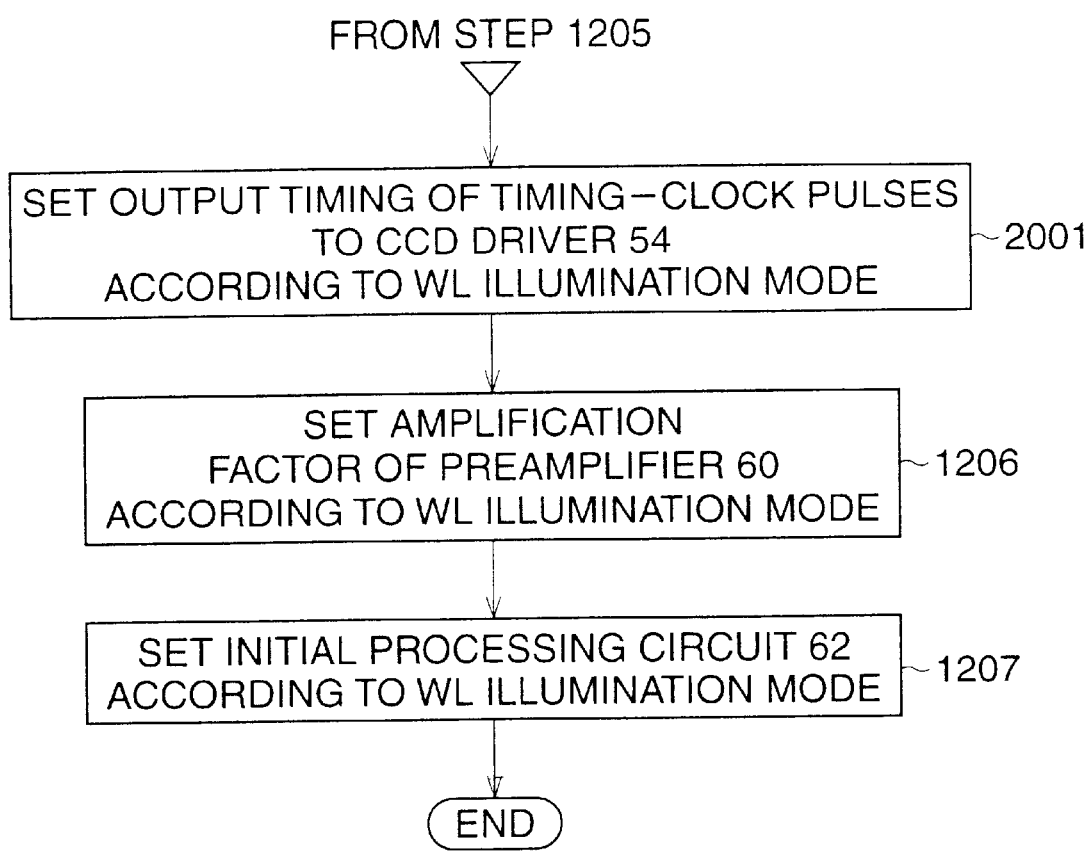
FIG. 20 is a part of flowchart of a partial modification of the initialization routine, shown in FIG. 12, when using the modified rotary color-filter/shutter of FIG. 18.

FIG. 20 shows a part of a flowchart of a partial modification of the initialization routine (FIG. 12), which is executed in the system controller 72 when using the rotary color-filter/shutter 44'.

As is apparent from FIG. 20, step 2001 is intervened between steps 1205 and 1206, and, in this added step, an output timing of timing-clock pulses from the timing controller 74 to the CCD driver 54 is set in accordance with the WL illumination mode, because the WL illumination mode is forcibly selected at the initial stage, as previously stated. In short, the series of reading-clock pulses is output from the CCD driver 54 to the CCD image sensor 14 in accordance with the timing chart of FIG. 10.

Figure 21:
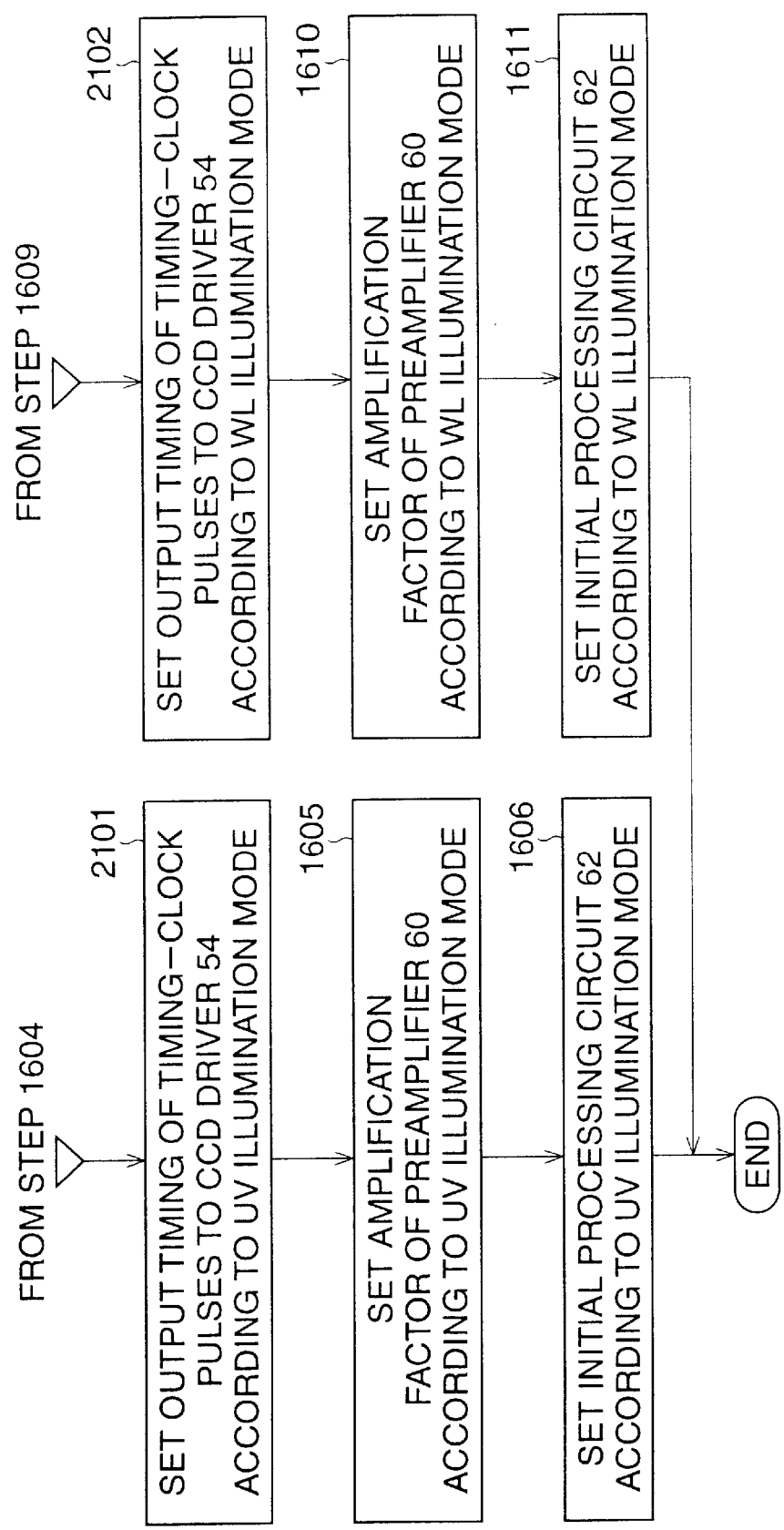
FIG. 21 is a part of a flowchart of a partial modification of the illumination-mode-switching routine, shown in FIG. 16, when using the modified rotary color-filter/shutter of FIG. 18.

FIG. 21 shows a part of a flowchart of a partial modification of the illumination-mode-switching routine (FIG. 16), which is executed in the system controller 72 when using the rotary color-filter/shutter 44'.

As is apparent from FIG. 21, step 2101 is intervened between steps 1604 and 1605, and step 2102 is intervened between steps 1609 and 1610. In the added step 2101, an output timing of timing-clock pulses from the timing controller 74 to the CCD driver 54 is set in accordance with the UV illumination mode such that the series of reading-clock pulses is output from the CCD driver 54 to the CCD image sensor 14 in accordance with the timing chart of FIG. 19. In the added step 2102, an output timing of timing-clock pulses from the timing controller 74 to the CCD driver 54 is set in accordance with the WL illumination mode such that the series of reading-clock pulses is output from the CCD driver 54 to the CCD image sensor 14 in accordance with the timing chart of FIG. 10.

The modified rotary color-filter/shutter 44' is preferable and advantageous for reproducing a fluorescent endoscope-image on the TV monitor 58 at a higher brightness, because the UV-light illumination period "UV-ILLU", for which the UV light radiates from the distal end of the optical light guide 18, is substantially extended to compensate for the low sensitivity of the CCD image sensor 14 to the fluorescent light.

Figure 22:
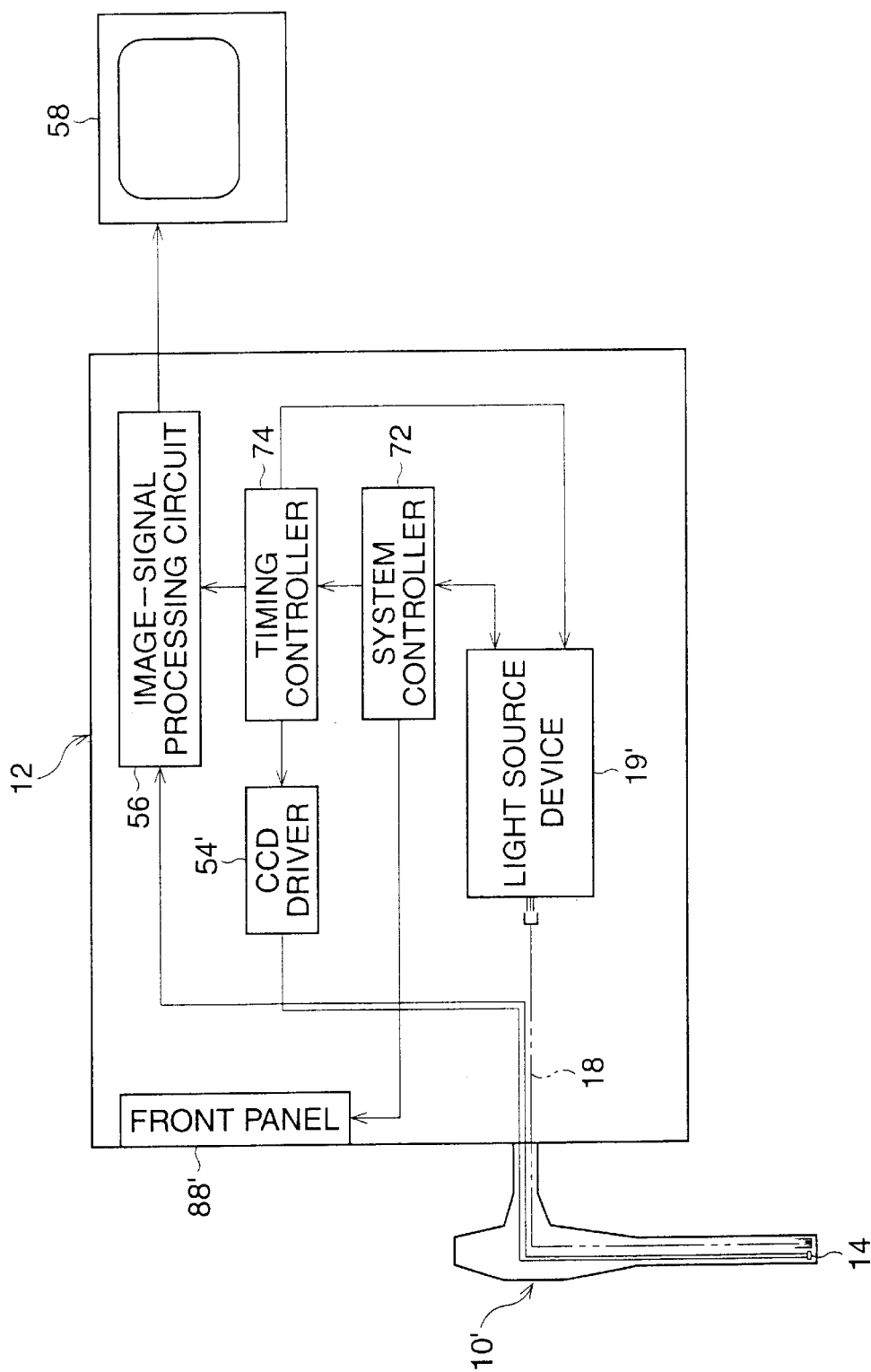
FIG. 22 is a schematic block diagram of a second embodiment of the electronic endoscope system according to the present invention.

With reference to FIG. 22, a second embodiment of an electronic endoscope system according to the present invention is schematically shown as a block diagram. Note, in FIG. 22, the same references as in FIG. 1 represent the same elements, and like elements bear like references primed. Although the scope 10 is provided with the CCD driver 54 in the first embodiment of FIG. 1, a CCD driver 54' may be provided in an image-signal processing unit 12 as shown in FIG. 22. Of course, in the second embodiment, when a scope 10' is connected to the image-signal processing unit 12, the CCD driver 54' is electrically connected to a CCD image sensor 14 of the scope 10'.

The second embodiment features a light source device 19', which is optically connected to a proximal end face of an optical light guide 18 when the connection is established between the scope 10' and the image-signal processing unit 12.

Figure 23:
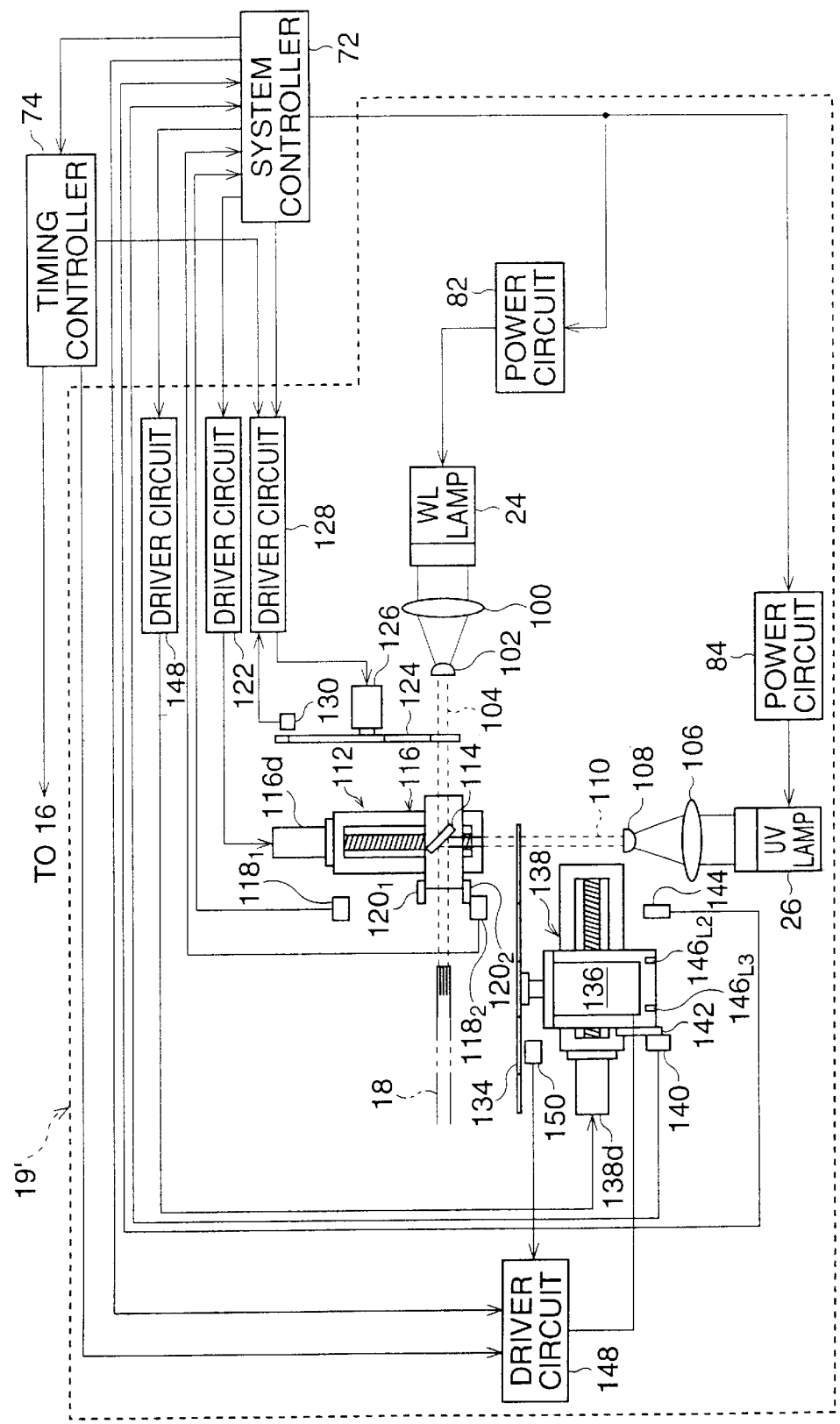
FIG. 23 is a schematic block diagram of a light source device used in the second embodiment.

With reference to FIG. 23, the light source device 19' is shown in detail as a block diagram. Similar to the light source device 19 shown in FIG. 1, the light source device 19' includes a white-light (WL) lamp and an ultraviolet (UV) lamp, indicated by the same references 24 and 26 as in FIG. 1, and the respective WL and UV lamps 24 and 26 are electrically energized by electric power circuits, indicated by the same references 82 and 84 as in FIG. 1. Similar to the first embodiment, a power supply of the WL lamp 24 from the electric power circuit 82 is controlled by a system controller 72, and the WL lamp 24 cannot only be turned ON and OFF but also controlled to vary the amount of light-emission of the WL lamp 24, if necessary. Also, a power supply of the UV lamp 26 from the electric power circuit 86 is controlled by the system controller 72, and the UV lamp 26 cannot only be turned ON and OFF but also controlled to vary the amount of light-emission of the UV lamp 26, if necessary.

As shown in FIG. 23, the WL lamp 24 is aligned with the proximal end face of the optical light guide 18, and a condenser lens 100 and a collimator lens 102 are provided therebetween. The white light, emitted from the WL lamp 24, is converged by the condenser lens 100, and is then converted by the collimator lens 102 into a parallel white light beam which is directed to the proximal end face of the optical light guide 18. Note, in FIG. 23, a path for the parallel white light beam is shown by broken lines, and is indicated by reference 104.

The UV lamp 26 is arranged such that the UV light emitted therefrom is directed to a region between the proximal end face the optical light guide 18 and the collimator lens 102 in a direction perpendicular to an optical axis of the collimator lens 102. The UV lamp 26 is associated with a condenser lens 106 and a collimator lens 108 which are aligned with each other with respect to the UV lamp 26. The UV light, emitted from the UV lamp 26, is converged by the condenser lens 106, and is then converted by the collimator lens 108 into a parallel UV light beam, which intersects the parallel white light beam (104) at a right angle. Note, in FIG. 23, a path for the parallel UV light beam is shown by broken lines, and is indicated by reference 11.

The light source device 19' is provided with a light-source switcher 112 which includes a light-deflector or reflective mirror 114, and a driving-mechanism 116 for moving the mirror 114 between a first operative position and a second operative position. Note, in FIG. 23, the mirror 114 is at the second operative position. The mirror 114 is inclined such that a reflective surface thereof defines an angle of 45° with the optical axis of the collimator lens 102.

Figure 24:
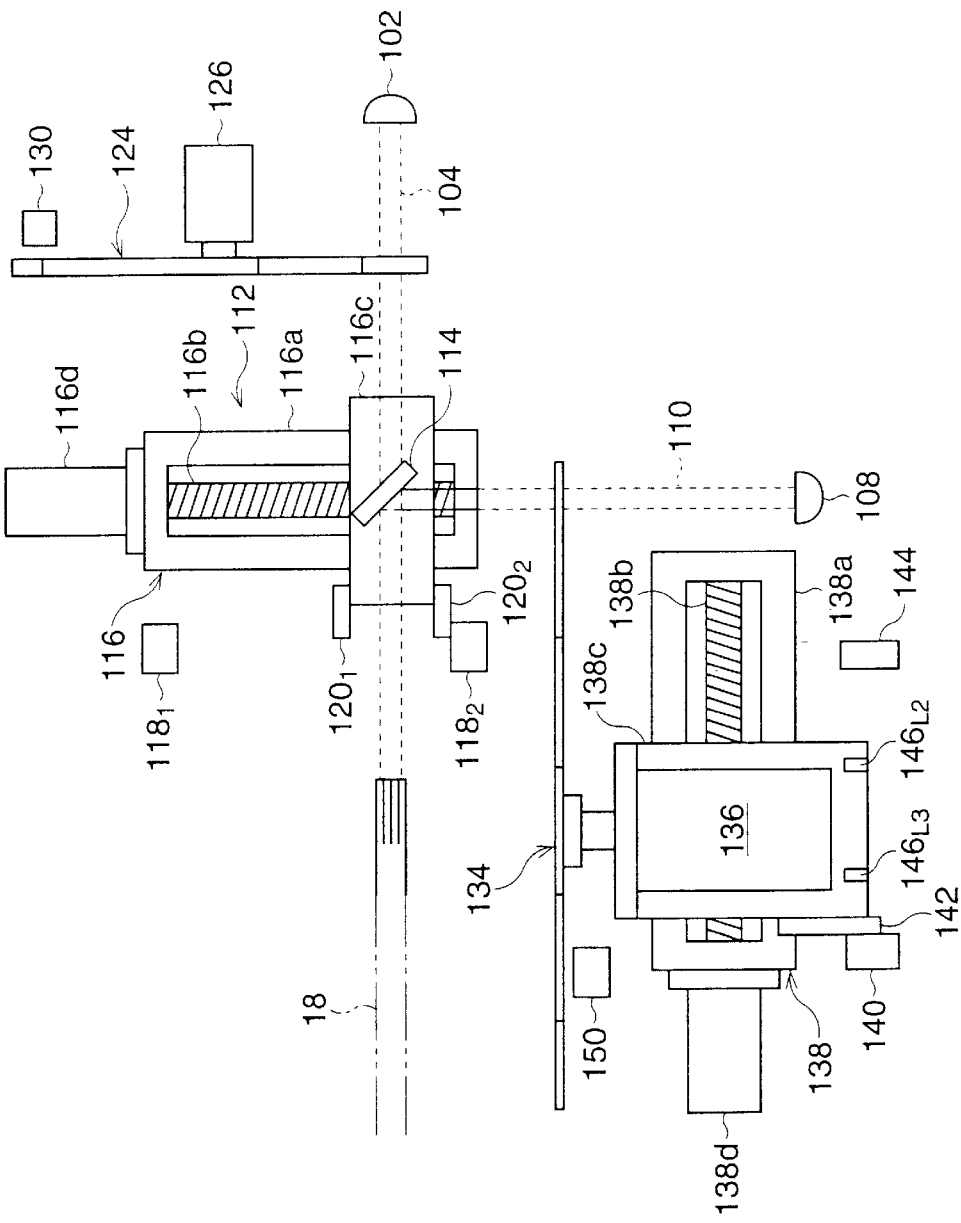
FIG. 24 is an enlarged view of a part of the light source device shown in FIG. 23.

The driving-mechanism 116 is constructed in substantially the same manner as the driving-mechanism 48 for the mirror 32 shown in FIGS. 4 and 5. In particular, as best shown in FIG. 24, the driving mechanism 116 includes a rectangular frame member 116a securely supported by an internal frame structure (not shown) of the image-signal processing unit 12, a ball screw 116b rotatably supported by and longitudinally extended through the frame member 116a, and a movable block member 116c threaded on the ball screw 116b. The driving-mechanism 116 is provided with an electric motor 116d, such as a servo motor, a stepping motor or the like, mounted on the top of the frame member 116a, and an output shaft of the motor 116d is coupled to an upper end of the ball screw 116b. Thus, when the ball screw 116b is rotated by the motor 116d, the block member 116c is moved upward and downward along the ball screw 116b, with the direction of movement of the block member 116c depending on the rotational direction of the ball screw 116b.

As is apparent from FIGS. 23 and 24, the mirror 114 is securely attached to a front face of the block member 116c such that the reflective surface thereof defines the angle of 45° with the optical axis of the collimator lens 102. Thus, it is possible to move the mirror 114 between the first and second operative positions by suitably controlling the motor 116d.

In order to suitably control the motor 116d to exactly position the mirror 114 at each of the first and second operative positions, as best shown in FIG. 24, a first limit switch $118_1$ and a second limit switch $118_2$ are arranged near the upper and lower ends of one of the lateral walls of the frame member 116a, and a first dog $120_1$, and a second dog $120_2$ are securely mounted on upper and lower surfaces of an end portion of the block member 116c intervened between the first and second limit switches $118_1$ and $118_2$, with these elements $118_1$, $118_2$, $120_1$ and $120_2$ being aligned with each other and parallel to the lateral wall of the frame member 116a. Note, preferably, the first and second limit switches $118_1$ and $118_2$ are securely supported by the lateral wall of the frame member 116a.

The first and second limit switches $118_1$ and $118_2$ are placed at respective locations corresponding to the first and second operative positions for the mirror 114, and are usually in an OFF-state. When the motor 116d is driven such that the block member 116c is moved toward the first limit switch $118_1$, the first dog $120_1$ comes into contact with the first limit switch $118_1$, thereby turning ON the first limit switch $118_1$. When the first limit switch $118_1$ is turned ON, the motor 116d is stopped, and thus the mirror 114, supported by the block member 116c, is positioned at the first operative position. Similarly, when the motor 116d is driven such that the block member 116c is moved toward the second limit switch $118_2$, the second dog $120_2$ comes into contact with the second limit switch $118_2$, thereby turning ON the second limit switch $118_2$. When the second limit switch $118_2$ is turned ON, the motor 116d is stopped, and thus the mirror 114, supported by the block member 116c, is positioned at the second operative position (FIGS. 23 and 24).

Similar to the first embodiment, when the mirror 114 is at the first operative position, the white light beam (104), emitted from the WL lamp 24, is directed to the proximal end face of the optical light guide 18, thereby introducing the white light beam (104) into the optical light guide 18. On the other hand, when the mirror 114 is moved from the first operative position to the second operative position (FIGS. 23 and 24), i.e. when the mirror 114 is intervened between the proximal end face of the optical light guide 18 and the collimator lens 102, the white light beam (104), emitted from the WL lamp 24, is blocked off by the rear surface of the mirror 114, and the UV light beam (110), emitted from the UV lamp 26, is reflected by the reflective surface of the mirror 114 and directed to the proximal end f ace of the optical light guide 18, thereby introducing the UV light beam (110) into the optical light guide 18.

In short, when the mirror 114 is at the first operative position, the WL lamp 24 is selected as the illumination lamp, i.e. a WL illumination mode is selected. On the other hand, when the mirror 114 is at the second operative position, the UV lamp 26 is selected as the illumination lamp, i.e. a UV illumination mode is selected.

The driving-mechanism 116 for the movement of the mirror 114 is operated under control of the system controller 72. Namely, as shown in FIG. 23, the motor 116d is connected to and driven by a driver circuit 122 which is operated under control of the system controller 72, and the first and second limit switches $118_1$ and $118_2$ are connected to the system controller 72. During the movement of the block member 116c toward the first limit switch $118_1$, the system controller 72 monitors whether the first limit switch $118_1$ is turned ON by the first dog $120_1$. When the first limit switch $118_1$ is turned ON, the motor 116d is stopped by the system controller 72, and thus the mirror 114 is positioned at the first operative position. Also, during the movement of the block member 116c toward the second limit switch $118_2$, the system controller 72 monitors whether the second limit switch $118_2$ is turned ON by the second dog $120_2$. When the second limit switch $118_2$ is turned ON, the motor 116d is stopped by the system controller 72, and thus the mirror 114 is positioned at the second operative position.

Similar to the first embodiment, the CCD image sensor 14 is constituted as a monochromatic CCD image sensor. When the mirror 114 is positioned at the first operative position, i.e. when the WL illumination mode is selected, an RGB field sequential-type color imaging method is used in the electronic endoscope system, thereby obtaining a full color image from the monochromatic CCD image sensor 14. To this end, a rotary color filter 124 is interposed in the white light beam path 104 between the collimator lens 102 and the second operative position for the mirror 114.

Figure 25:
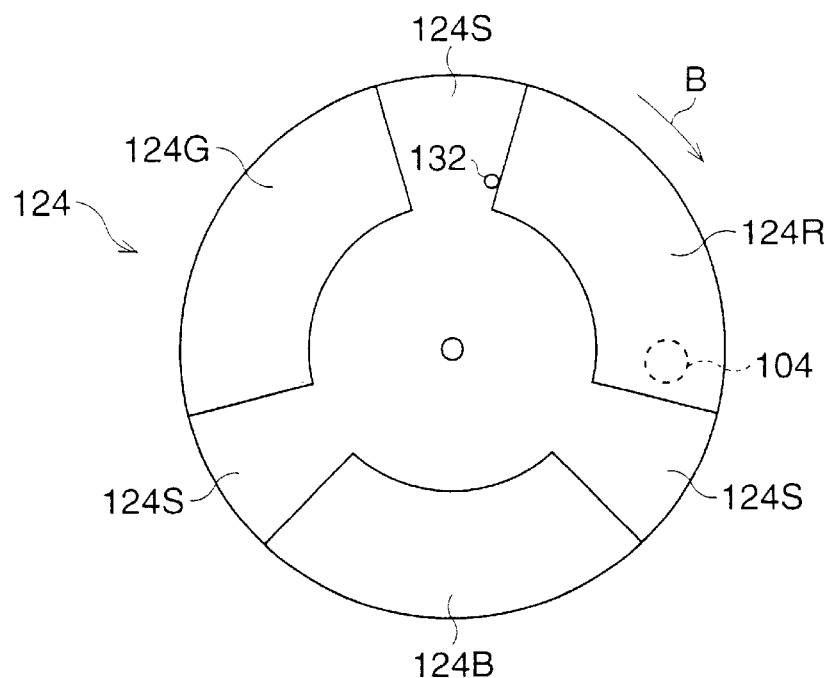
FIG. 25 is a plan view of a rotary color filter used in the second embodiment.

As shown in FIG. 25, the rotary color filter 124 comprises a disk element having three sector-shaped color filters, i.e. red, green and blue filters 124R, 124G and 124B which are uniformly and circumferentially arranged such that three centers of the color filters 124R, 124G and 124B are spaced from each other at regular angular intervals of 120 degrees, with a sector area between two adjacent color filters being constructed as a light-shielding area 124S.

As best shown in FIG. 24, the rotary color filter 124 is securely mounted on an output shaft of a suitable electric motor 126, such as servo-motor, a stepping motor or the like, and is rotated by the motor 126 at a given rotational frequency in accordance with a commonly used image-reproduction method, such as the NTSC system, the PAL system and so on. As explained in the first embodiment, in the NTSC system, the rotational frequency of the rotary color filter 124 is 30 Hz, and, in the PAL system, the rotational frequency of the rotary color filter 124 is 25 Hz.

The rotary color filter 124 is positioned such that a cross-sectional area of the white light beam path 104 is encompassed by an annular area which is defined by the red, green and blue filters 124R, 124G and 124B, as shown by a broken line in FIG. 25. Thus, while the rotary color filter 124 is rotated in a direction indicated by arrow B in FIG. 25, red, green and blue lights are cyclically and sequentially made incident on the proximal end face of the optical light guide 18, i.e. the red, green and blue lights are cyclically and sequentially emitted from a distal end face of the optical light guide 18.

Similar to the rotary color-filter/shutter 44 in the first embodiment, when the rotary color filter 124 is rotated at the rotational frequency 30 Hz (NTSC), the rotary color filter 124 makes one revolution over a time period of 1/30 sec (about 33.3 ms), and thus the white light, emitted from the WL lamp 24, passes through each of the color filters 124R, 124G and 124B over a time period of 1/180 sec (about 33.3/6 ms). Thus, the red, green and blue lights sequentially and cyclically radiate from the distal end of the optical light guide 18. Namely, red, green and blue optical images are sequentially and cyclically focused onto the light-receiving surface of the CCD image sensor 14.

While the red, green and blue optical images are cyclically focused on the light-receiving surface of the CCD image sensor 14, each of the red, green and blue optical images is converted into a frame of monochromatic (red, green, blue) analog image-pixel signals by the CCD image sensor 14, and each frame of monochromatic analog image-pixel signals is read from the CCD image sensor 14 over consecutive light-shielding time periods (about 33.3/6 ms), corresponding to the light-shielding area 124S between two adjacent color filters (124R, 124G, 124B) of the rotary color filter 124. The read color (red, green and blue) image signals are processed in substantially the same manner as in the first embodiment, thereby producing a component-type color video signal.

Similar to the WL illumination mode in the first embodiment, the reading of the image-pixel signals from the CCD image sensor 14 is performed in a regular sequence by the CCD driver 54' in accordance with a series of timing-clock pulses output from the timing controller 74 to the CCD driver 54'. Namely, whenever a timing-clock pulse is input from the timing controller 74 to the CCD driver 54', a series of reading-clock pulses is output from the CCD driver 54' to the CCD image sensor 14, whereby the image-pixel signals are read from the CCD image sensor 14 in accordance with the reading-clock pulses.

Of course, it is necessary to always precisely synchronize the output timing of the timing-clock pulses from the timing controller 74 to the CCD driver 54' with each revolution of the rotary color filter 124, before the reading of the image-pixel signals from the CCD image sensor 14 can be performed at a proper timing. To this end, as shown in FIG. 23, the motor 126 is driven by a driver circuit 128 which is precisely controlled by the system controller 72 and the timing controller 74 such that the output timing of timing-clock pulses from the timing controller 74 to the CCD driver 54, is synchronized with an output timing of drive pulses from the driver circuit 128 to the motor 126.

However, similar to the rotary color-filter/shutter 44 in the first embodiment, in reality, it is impossible to obtain precise synchronization between the revolution of the rotary color filter 124 and the output timing of the timing-clock pulses from the timing controller 74 to the CCD driver 54' for the same reasons as stated above.

Thus, a phase detector 130 is arranged at a suitable location to detect a rotational-phase of the rotary color filter 124. Similar to the phase detector 78 in the first embodiment, the phase detector 130 comprises a light-emitting element, such as an light-emitting diode (LED), and a light-receiving element, such as a photodiode (PD). On the other hand, the rotary color filter 124 has a small reflective area 132 formed thereon, and the reflective area 132 is positioned at a radial edge of a light-shielding area 124S, which bounds on the red filter 124R, as shown in FIG. 25.

While the rotary color filter 124 is rotated, the phase detector 130 detects the passage of the small reflective area 132. Namely, when the light, emitted from the LED of the phase detector 130, is reflected by the small reflective area 132, during the rotation of the rotary color filter 124, the reflected light is received by the PD of the phase detector 130, and thus the rotational-phase of the rotary color filter 124 is detected by the phase detector 13.

When the reflected light is received by the PD of the phase detector 130, the PD outputs a phase-detection pulse to the driver circuit 128. The driver circuit 128 includes a phase-locked-loop (PLL) circuit, and outputs the drive pulses to the motor 126 such that a phase of the phase-detection pulse coincides with a phase of a drive pulse every revolution of the rotary color filter 124, whereby it is possible to always precisely synchronize the output timing of the timing-clock pulses from the timing controller 74 to the CCD driver 54' with each revolution of the rotary color filter 124. Hence, the reading of the image-pixel signals from the CCD image sensor 14 can be performed at the proper timing.

On the other hand, as best shown in FIG. 24, a rotary shutter 134 is interposed in the UV light beam path 110 between the collimator lens 108 and the second operative position for the mirror 114. When the mirror 114, is positioned at the second operative position, i.e. when the UV illumination mode is selected, the rotary shutter 134 is used to cyclically and sequentially radiate the ultraviolet light from the distal end of the optical light guide.

Figure 26:
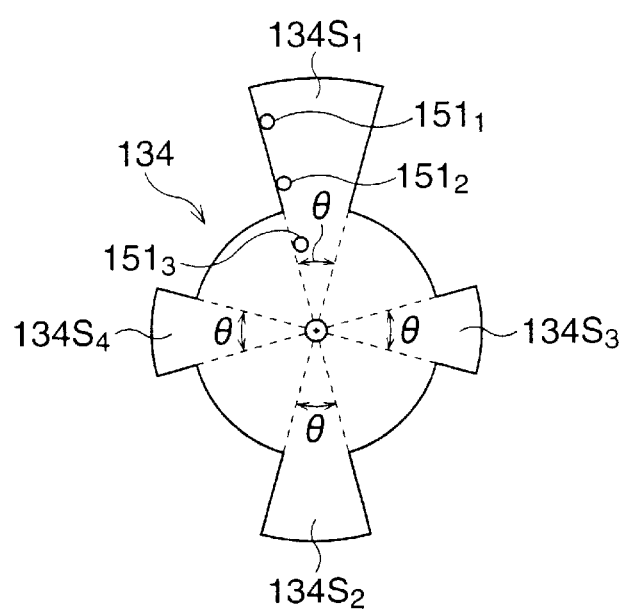
FIG. 26 is a plan view of a rotary shutter used in the second embodiment.

As shown in FIG. 26, the rotary shutter 134 comprises a disk element having four sector-shaped light-shielding areas 134S$_1$, 134S$_2$, 134S$_3$ and 134S$_4$, which are defined by the same center angle of θ, and which are circumferentially and uniformly arranged such that three centers of the light-shielding areas 134S$_1$, 134S$_2$, 134S$_3$ and 134S$_4$ are spaced from each other at regular angular intervals of 90 degrees. The light-shielding areas 134S$_1$ are 134S$_2$ are diametrically opposed to each other, and the light-shielding areas 134S$_3$ and 134S$_4$ are diametrically opposed to each other. The light-shielding area 134S$_1$ has a maximum radial length, and the light-shielding area 134S$_2$ has a middle radial length. The light-shielding areas 134S$_3$ and 134S$_4$ have a same radial length which is shorter than the radial lengths of the light-shielding areas 134S$_1$ are 134S$_2$.

As best shown in FIG. 24, the rotary shutter 134 is securely mounted on an output shaft of a suitable electric motor 136, such as servo-motor, a stepping motor or the like, and a longitudinal axis of the output shaft of the motor 136 is in parallel to the UV light beam path 11. In this second embodiment, the rotary shutter 134 is rotated by the motor 136 at a lower rotational frequency than the rotational frequency of the color filter 124. For example, the rotational frequency of the rotary shutter 134 is set to one-fourth the rotational frequency of the rotary color filter 124. Namely, the rotary shutter 134 is rotated at the rotational frequency of 7.5 Hz (30/4 Hz).

The rotary shutter 134 is moved back and froth with respect to the UV light beam path 110, and is selectively positioned at one of first, second and third operative positions, whereby the light-shielding areas 134S$_1$, 134S$_2$, 134S$_3$ and 134S$_4$ are selectively intervened in the UV light beam path 110. To this end, the motor 136 is associated with a driving-mechanism 138 for the movement of the rotary shutter 134 between the first, second and third operative positions.

As shown in FIGS. 23 and 24, the driving-mechanism 138 includes a rectangular frame member 138a securely supported by the internal frame structure of the image-signal processing unit 12, a ball screw 138b rotatably supported by and longitudinally extended through the frame member 138a, and a movable carriage member 138c threaded on the ball screw 48b.

As shown in FIGS. 23 and 24, the driving-mechanism 138 is provided with an electric motor 138d, such as a servo motor, a stepping motor or the like, mounted on a side end of the frame member 138a, and an output shaft of the motor 138d is coupled to an end of the ball screw 138b. Thus, when the ball screw 138b is rotated by the motor 138d, the carriage member 138c is moved back and froth with respect to the UV light beam path 110, with the direction of movement of the carriage member 138c depending on the rotational direction of the ball screw 138b.

As is apparent from FIGS. 23 and 24, the motor 136 for the rotary shutter 134 is securely supported by the carriage member 138c. Thus, it is possible to move the rotary shutter 134 between the first, second and third operative positions by suitably controlling the motor 138d.

In order to exactly position the rotary shutter 134 at the first operative position, as best shown in FIG. 24, a limit switch 140 is arranged near the side end of the frame member 138a on which the motor 138d is mounted, and a dog 142 is securely attached to a side of the carriage member 138c such that the limit switch 140 can be operated by the dog 142. Note, preferably, the limit switch 140 is securely supported by the frame member 138a.

The limit switch 140 is placed at a location corresponding to the first operative position for the rotary shutter 134, and are usually in an OFF-state. When the motor 138d is driven such that the carriage member 138c is moved toward the limit switch 140, the dog 142 comes into contact with the limit switch 140, thereby turning ON the switch 14. When the limit switch 140 is turned ON, the motor 48d is stopped, and thus the rotary shutter 134, supported by the carriage member 138c, is positioned at the first operative position as shown in FIGS. 23 and 24.

In order to exactly position the rotary shutter 134 at one of the second and third operative positions, as best shown in FIG. 24, a magnetic position-detector 144 is arranged near a passage of a bottom edge of the carriage member 138c, and two detective magnet pieces 146$_{L2}$ and 146$_{L3}$ are securely attached to the bottom edge of the carriage member 138c. Thus, while the motor 138d is driven such that the carriage member 138c is moved from the first operative position toward the magnetic position-detector 144, firstly the detective magnet piece 146$_{L2}$ is detected by the magnetic position-detector 144, and then the detective magnet pieces 146$_{L3}$ is detected by the magnetic position-detector 144. Note, the magnetic position-detector 144 may be securely supported by the frame member 138a.

A relative location of the detective magnet piece 146$_{L2}$ to the magnetic position-detector 144 corresponds to the second operative position for the rotary shutter 134, and a relative location of the detective magnet piece 146$_{L3}$ to the magnetic position-detector 144 corresponds to the third operative position for the rotary shutter 134. Namely, when the detective magnet piece 146$_{L2}$ is detected by the magnetic position-detector 144, the rotary shutter 134 is positioned at the second operative position, and when the detective magnet piece 146$_{L3}$ is detected by the magnetic position-detector 144, the rotary shutter 134 is positioned at the third operative position.

The driving-mechanism 138 for the movement of the rotary shutter 134 is operated under control of the system controller 72. As shown in FIG. 23, the motor 138d is connected to and driven by a driver circuit 148 which is operated under control of the system controller 72, and the limit switch 140 and the magnetic position-detector 144 are connected to the system controller 72.

During the movement of the carriage member 138c toward the limit switch 140, the system controller 72 monitors whether the limit switch 140 is turned ON by the dog 142. When the limit switch 140 is turned ON, the motor 138d is stopped by the system controller 72, thereby positioning the rotary shutter 134 at the first operative position.

On the other hand, during the movement of the carriage member 138c toward the magnetic position-detector 144, the system controller 72 monitors whether either the detective magnet piece $146_{L2}$ or $146_{L3}$ has been detected by the magnetic position-detector 144. If the motor 116d is stopped when the detective magnet piece $146_{L2}$ is detected by the magnetic position-detector 144, the rotary shutter 134 is positioned at the second operative position. Also, if the motor 116d is stopped when the detective magnet piece $146_{L3}$ is detected by the magnetic position-detector 144, the rotary shutter 134 is positioned at the third operative position.

Figure 27:
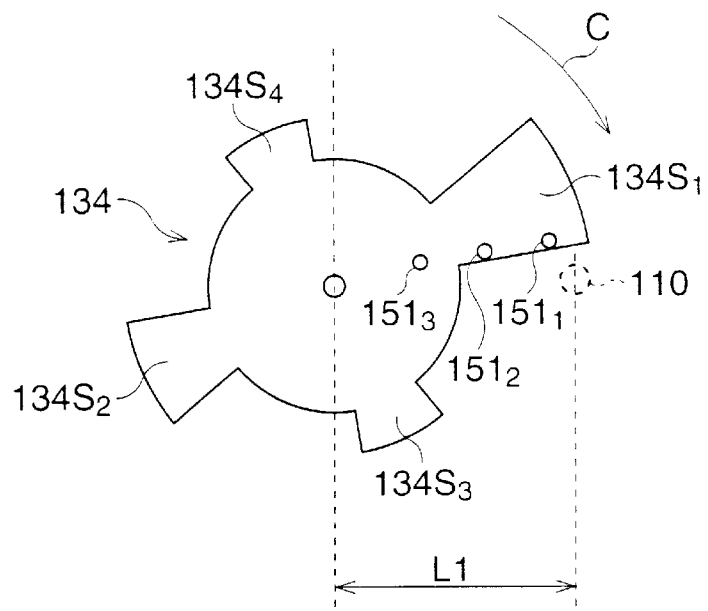
FIG. 27 is a plan view, similar to FIG. 26, showing the rotary shutter at a first operative position.

As shown in FIG. 27, when the rotary shutter 134 is positioned at the first operative position, a distance L1 between the center of the rotary shutter 134 and the center the UV light beam path 110 is somewhat shorter than the maximum radial length of the light-shielding area $134S_1$. Thus, when the rotary shutter 134 is rotated at the first operative position as indicated by arrow C in FIG. 27, only the light-shielding area $134S_1$ passes through the UV light beam path 110.

Figure 28:
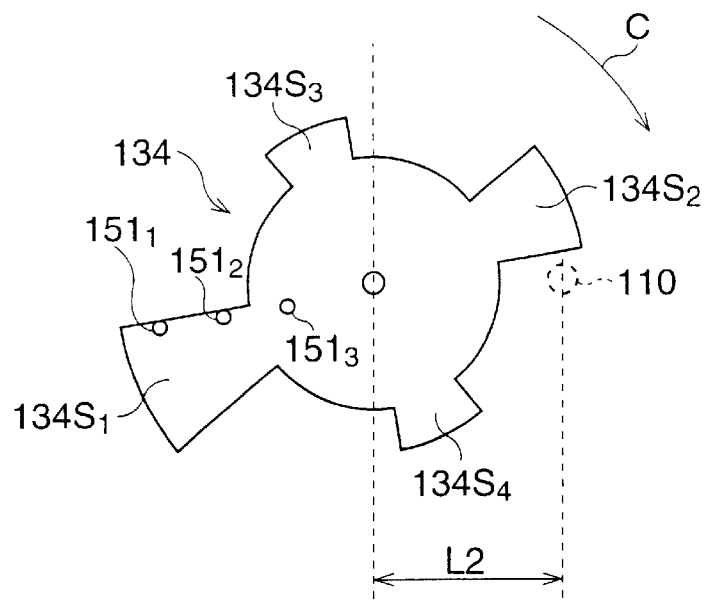
FIG. 28 is a plan view, similar to FIG. 26, showing the rotary shutter at a second operative position.

As shown in FIG. 28, when the rotary shutter 134 is positioned at the second operative position, a distance L2 between the center of the rotary shutter 134 and the center the UV light beam path 110 is somewhat shorter than the middle radial length of the light-shielding area $134S_2$. Thus, when the rotary shutter 134 is rotated at the second operative position as indicated by arrow C in FIG. 28, the light-shielding areas $134S_1$ and $134S_2$ pass through the UV light beam path 110.

Figure 29:
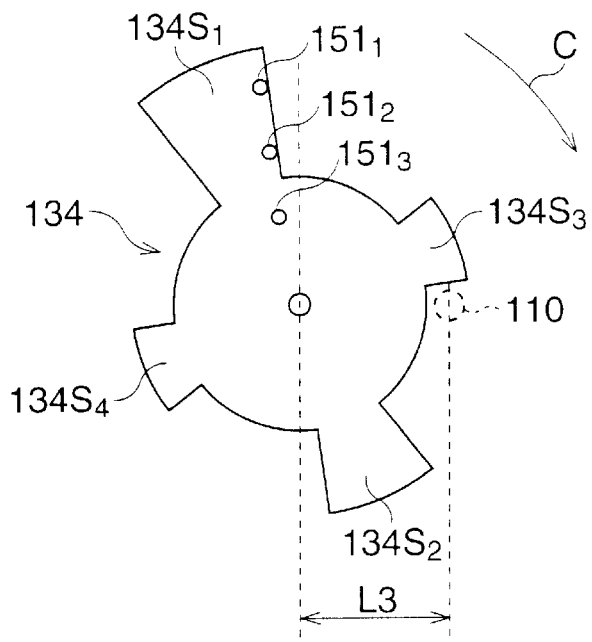
FIG. 29 is a plan view, similar to FIG. 26, showing the rotary shutter at a third operative position.

As shown in FIG. 29, when the rotary shutter 134 is positioned at the third operative position, a distance L3 between the center of the rotary shutter 134 and the center the UV light beam path 110 is somewhat shorter than the minimum radial length of the light-shielding areas $134S_3$ and $134S_4$. Thus, when the rotary shutter 134 is rotated at the third operative position as indicated by arrow C in FIG. 29, all the light-shielding areas $134S_1$, $134S_2$ pass through the UV light beam path 110.

Figure 30:
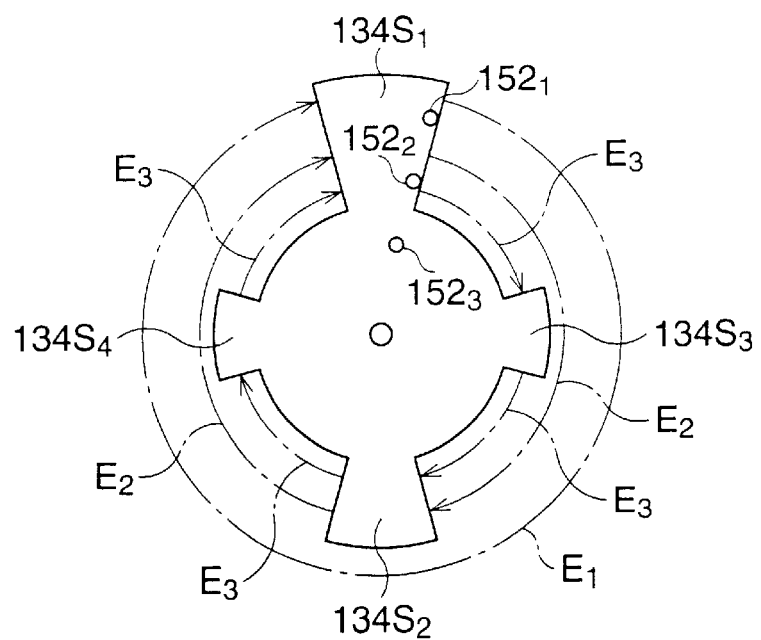
FIG. 30 is a plan view, similar to FIG. 26, showing features of the rotary shutter.

As shown in FIG. 30, an exposure area $E_1$ is defined by the light-shielding area $134S_1$ when positioning the rotary shutter 134 at the first operative position. Accordingly, when the mirror 114 is at the second operative position, and when the rotary shutter 134 is rotated at the first operative position, the UV light, emitted from the UV lamp 26, radiates from the distal end of the optical light guide 18 over an exposure period that corresponds to the exposure area $E_1$, every revolution of the rotary shutter 134. Note, this UV exposure mode is referred to as a first UV exposure mode hereinafter.

Also, as shown in FIG. 30, two exposure areas $E_2$ are defined by the light-shielding areas $134S_1$ and $134S_2$ when positioning the rotary shutter 134 at the second operative position. Accordingly, when the mirror 114 is at the second operative position, and when the rotary shutter 134 is rotated at the second operative position, the UV light, emitted from the LTV lamp 26, radiates two times from the distal end of the optical light guide 18 over two exposure periods that correspond to the exposure areas $E_2$, every revolution of the rotary shutter 134. Note, this UV exposure mode is referred to as a second UV exposure mode hereinafter.

Further, as shown in FIG. 30, four exposure areas $E_3$ are defined by the light-shielding areas $134S_1$, $134S_2$, $134S_3$ and $134S_4$ when positioning the rotary shutter 134 at the third operative position. Accordingly, when the mirror 114 is at the second operative position, and when the rotary shutter 134 is rotated at the third operative position, the UV light, emitted from the UV lamp 26, radiates four times from the distal end of the optical light guide 18 over four exposure periods that correspond to the exposure areas $E_3$, every revolution of the rotary shutter 134. Note, this UV exposure mode is referred to as a third UV exposure mode hereinafter.

Of course, similar to the UV illumination (exposure) mode in the first embodiment, in each of the first, second and third UV exposure modes, during the rotation of the rotary shutter 134, optical fluorescent images are sequentially and cyclically focused on the light-receiving surface of the CCD image sensor 14, and each of the fluorescent images is converted into a frame of fluorescent analog image-pixel signals by the CCD image sensor 14. Each frame of fluorescent analog image-pixel signals is read from the CCD image sensor 14 over a light-shielding period corresponding to one of the light-shielding areas $134S_1$, $134S_2$, $134S_3$ and $134S_4$. The reading of image-pixel signals from the CCD image sensor 14 is performed by the CCD driver 54', which is operated in accordance with a series of timing-clock pulses output from the timing controller 72 to the CCD driver 54'. In short, similar to the aforesaid cases, whenever a timing-clock pulse is input from the timing controller 74 to the CCD driver 54', a series of reading-clock pulses is output from the CCD driver 54' to the CCD image sensor 14, whereby the fluorescent image-pixel signals are read from the CCD image sensor 14 in accordance with the reading-clock pulses.

Similar to the aforesaid cases, in each of the first, second and third UV exposure modes, it is necessary to always precisely synchronize an output timing of the timing-clock pulses from the timing controller 74 to the CCD driver 54' with each revolution of the rotary shutter 134, before the reading of the fluorescent image-pixel signals from the CCD image sensor 14 can be performed a proper timing. To this end, as shown in FIG. 23, the motor 136 is driven by a driver circuit 148, which is precisely controlled by the system controller 72 and the timing controller 74, such that the output timing of timing-clock pulses from the timing controller 74 to the CCD driver 54' is synchronized with an output timing of drive pulses from the driver circuit 148 to the motor 136.

However, similar to the rotary color-filter/shutter 44 in the first embodiment, in reality, it is impossible to obtain precise synchronization between each revolution of the rotary shutter 134 and the output timing of the timing-clock pulses from the timing controller 74 to the CCD driver 54' for the same reasons as stated above.

Thus, a phase detector 150 is arranged at a suitable location to detect a rotational-phase of the rotary shutter 134. Similar to the phase detector 78 in the first embodiment, the phase detector 150 comprises a light-emitting element, such as an light-emitting diode (LED), and a light-receiving element, such as a photodiode (PD). On the other hand, the rotary shutter 134 has first, second and third small reflective areas $151_1$, $151_2$ and $151_3$ formed thereon, and these reflective areas are $151_1$, $151_2$ and $151_3$ positioned at a radial edge of the light-shielding area $134S_1$, as shown in FIGS. 26 to 30. Note, similar to the aforesaid cases, each of the reflective areas $151_1$, $151_2$ and $151_3$ may be formed by adhering a small piece of aluminum foil on the rotary shutter 134.

While the rotary shutter 134 is rotated at the first operative position, i.e. while the first UV exposure mode is selected (FIG. 27), the phase detector 150 detects the passage of the first small reflective area $151_1$. Also, while the rotary shutter 134 is rotated at the second operative position, i.e. while the second UV exposure mode is selected (FIG. 28), the phase detector 150 detects the passage of the second small reflective area $151_2$. Further, while the rotary shutter 134 is rotated at the third operative position, i.e. while the third UV exposure mode is selected (FIG. 29), the phase detector 150 detects the passage of the third small reflective area $151_3$. Namely, when the light, emitted from the LED of the phase detector 150, is reflected by the small reflective area ($151_1$, $151_2$, $151_3$), during the rotation of the rotary shutter 134, the reflected light is received by the PD of the phase detector 150.

When the reflected light is received by the PD of the phase detector 150, the PD outputs a phase-detection pulse to the driver circuit 148. The driver circuit 148 includes a phase-locked-loop (PLL) circuit, and outputs the drive pulses to the motor 136 such that a phase of the phase-detection pulse coincides with a phase of the drive pulses every revolution of the rotary shutter 134, whereby it is possible to always precisely synchronize the output timing of the timing-clock pulses from the timing controller 74 to the CCD driver 54' with each revolution of the rotary shutter 134, whereby the reading of the fluorescent image-pixel signals from the CCD image sensor 14 can be performed at the proper timing in each of the first, second and third UV exposure modes.

Figure 31:
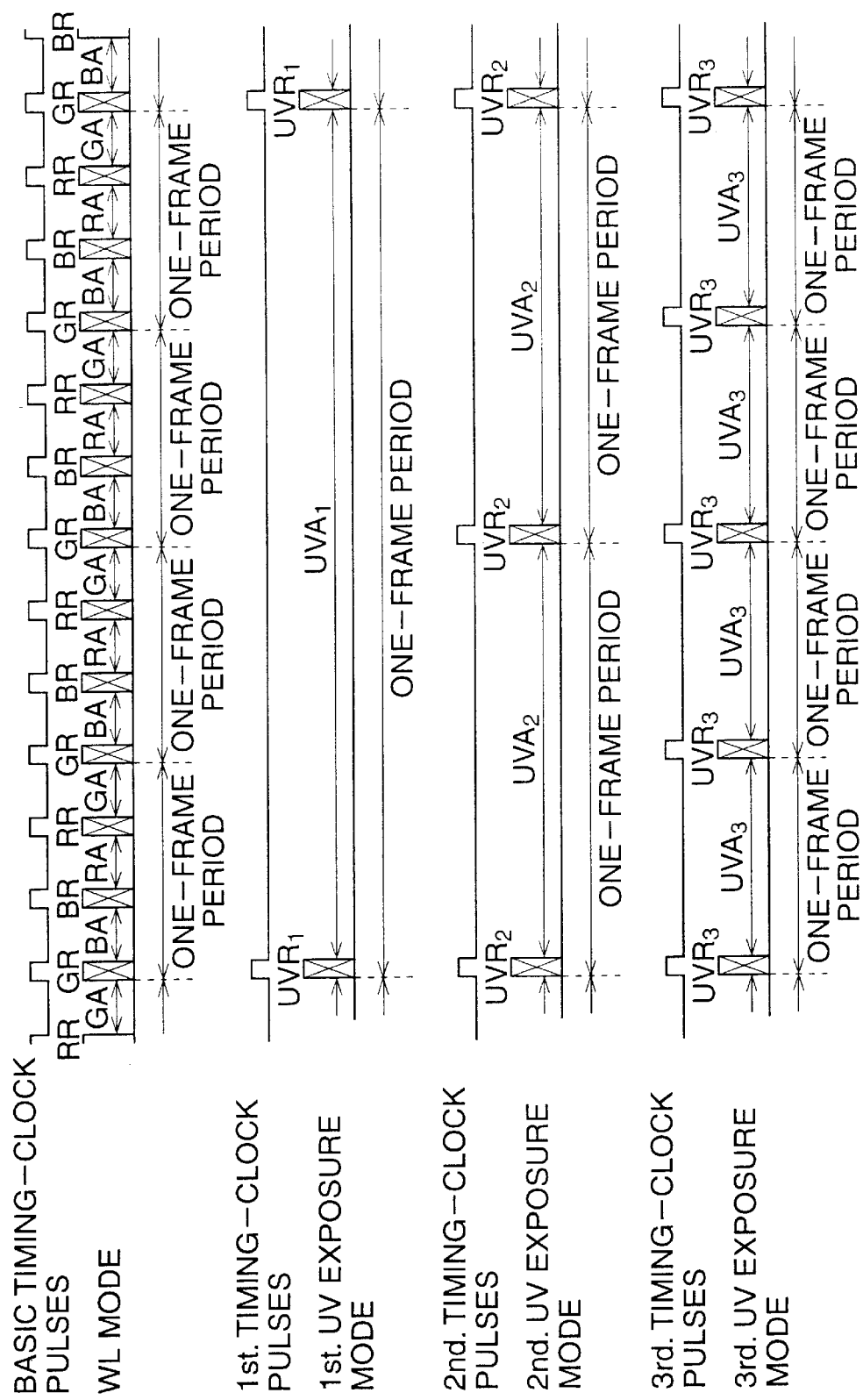
FIG. 31 is a timing chart showing a reading of image-pixel signals from the CCD image sensor in a white light illumination mode and an ultraviolet light illumination mode in the second embodiment.

FIG. 31 shows a timing chart which represents a frame of image-pixel signals being read from the CCD image sensor 14 in the second embodiment.

In the WL illumination mode shown in FIG. 31, a one-frame period corresponds to the time period of 1/30 sec (about 33.3 ms), during which the rotary color filter 124 makes one revolution. In the WL illumination mode, a series of basic timing-clock pulses having a given frequency is output from the timing controller 74 to the CCD driver 54' in synchronization with the output timing of drive pulses from the driver circuit 128 to the motor 126, i.e. the revolution of the rotary color filter 124. Whenever a basic timing-clock pulse is output from the timing controller 74 to the CCD driver 54', a series of reading-clock pulses is output from the CCD driver 54' to the CCD image sensor 14, whereby the reading of a frame of monochromatic (red, green, blue) image-pixel signals from the CCD image sensor 14 is performed in accordance with the reading-clock pulses.

In particular, in the WL illumination mode of FIG. 31, a red-light illumination period, during which the red light radiates from the distal end of the optical light guide 18, is indicated by reference "RA". During the red-light illumination period "RA", an optical red image is formed on the light-receiving surface of the CCD image sensor 14. The optical red image is converted into a frame of red analog image-pixel signals by the CCD image sensor 14, and then the frame of red analog image-pixel signals is read from the CCD image sensor 14 over a consecutive light-shielding period, which corresponds to the light-shielding area 124S between the red filter 124R and the green filter 124G. Note, in FIG. 31, the light-shielding period, during which the red analog image-pixel signals are read from the CCD image sensor 14, is indicated by reference "RR".

Also, in the WL illumination mode shown in FIG. 31, a green-light illumination period, during which the green light radiates from the distal end of the optical light guide 18, is indicated by reference "GA". During the green-light illumination period "GA", an optical green image is formed on the light-receiving surface of the CCD image sensor 14. The optical green image is converted into a frame of green analog image-pixel signals by the CCD image sensor 14, and the frame of green analog image-pixel signals is read from the CCD image sensor 14 over a consecutive light-shielding period, which corresponds to the light-shielding area 124S between the green filter 124G and the blue filter 124B. Note, in FIG. 31, the light-shielding period, during which the green analog image-pixel signals are read from the CCD image sensor 14, is indicated by reference "GR".

Further, in the WL illumination mode shown in FIG. 31, a blue-light illumination period, during which the blue light radiates from the distal end of the optical light guide 18, is indicated by reference "BA". During the blue-light illumination period "BA", an optical blue image is formed on the light-receiving surface of the CCD image sensor 14. The optical blue image is converted into a frame of blue analog image-pixel signals by the CCD image sensor 14, and the frame of blue analog image-pixel signals is read from the CCD image sensor 14 over a consecutive light-shielding period, which corresponds to the light-shielding area 124S between the blue filter 124B and the red filter 124R. Note, in FIG. 31, the light-shielding period, during which the blue analog image-pixel signals are read from the CCD image sensor 14, is indicated by reference "BR".

In the first UV exposure mode shown in FIG. 31, a one-frame period corresponds to the time period of 4/30 sec (about 133.2 ms), during which the rotary shutter 134 makes one revolution, because the rotational frequency of the rotary shutter 134 is set to one-fourth the rotational frequency of the rotary color filter 124, as stated above. Namely, the rotary shutter 134 is rotated at the rotational frequency of 7.5 Hz (30/4 Hz). In the first UV exposure mode, a first series of timing-clock pulses, having a lower frequency than that of the basic timing-clock pulses used in the WL illumination mode, is output from the timing controller 74 to the CCD driver 54'. Whenever a first timing-clock pulse is output from the timing controller 74 to the CCD driver 54', a series of reading-clock pulses is output from the CCD driver 54' to the CCD image sensor 14, whereby a frame of fluorescent image-pixel signals is read from the CCD image sensor 14 in accordance with the reading-clock pulses.

In the first UV exposure mode shown in FIG. 31, an ultra-violet light illumination period, during which the ultra-violet light radiates from the distal end of the optical light guide 18, is indicated by reference "$UVA_1$". During the ultraviolet light illumination period "$UVA_1$", a fluorescent image is formed on the light-receiving surface of the CCD image sensor 14, and is converted into a frame of fluorescent analog image-pixel signals by the CCD image sensor 14. The frame of fluorescent analog image-pixel signals is then read from the CCD image sensor 14 over a consecutive light-shielding period, which corresponds to the light-shielding area $134S_1$ of the rotary shutter 134. Note, in FIG. 31, the light-shielding period, during which the fluorescent analog image-pixel signals are read from the CCD image sensor 14, is indicated by reference "$UVR_1$".

In the second UV exposure mode shown in FIG. 31, a one-frame period corresponds to the time period of 2/30 sec (about 66.6 ms), during which the rotary shutter 134 makes one-half revolution. In the second UV exposure mode, a second series of timing-clock pulses, having twice the frequency as that of the first series of timing-clock pulses used in the first UV exposure mode, is output from the timing controller 74 to the CCD driver 54'. Whenever a second timing-clock pulse is output from the timing controller 74 to the CCD driver 54', a series of reading-clock pulses is output from the CCD driver 54' to the CCD image sensor 14, whereby a frame of fluorescent image-pixel signals is read from the CCD image sensor 14 in accordance with the reading-clock pulses.

In the second UV exposure mode shown in FIG. 31, an ultraviolet light illumination period, during which the ultraviolet light radiates from the distal end of the optical light guide 18, is indicated by reference "$UVA_2$". During the ultraviolet light illumination period "$UVA_2$", a fluorescent image is formed on the light-receiving surface of the CCD image sensor 14, and is converted into a frame of fluorescent analog image-pixel signals by the CCD image sensor 14. The frame of fluorescent analog image-pixel signals is read from the CCD image sensor 14 over a consecutive light-shielding period, which corresponds to either the light-shielding area $134S_1$ or $134S_2$. Note, in FIG. 31, the light-shielding period, during which the fluorescent analog image-pixel signals are read from the CCD image sensor 14, is indicated by reference "$UVR_2$".

In the third UV exposure mode shown in FIG. 31, a one-frame period corresponds to the time period of 1/30 sec (about 33.3 ms), during which the rotary shutter 134 makes one-fourth revolution.

In the third UV exposure mode, a third series of timing-clock pulses, having four times the frequency as that of the first series of timing-clock pulses used in the first UV exposure mode, is output from the timing controller 74 to the CCD driver 54'. Whenever a third timing-clock pulse is output from the timing controller 74 to the CCD driver 54', a series of reading-clock pulses is output from the CCD driver 54' to the CCD image sensor 14, whereby a frame of fluorescent image-pixel signals is read from the CCD image sensor 14 is performed in accordance with the reading-clock pulses.

In the third UV exposure mode shown in FIG. 31, an ultra-violet light illumination period, during which the ultra-violet light radiates from the distal end of the optical light guide 18, is indicated by reference "$UVA_3$". During the ultra-violet light illumination period "$UVA_3$", a fluorescent image is formed on the light-receiving surface of the CCD image sensor 14, and is converted into a frame of fluorescent analog image-pixel signals by the CCD image sensor 14. The frame of fluorescent analog image-pixel signals is then read from the CCD image sensor 14 over a consecutive light-shielding period, which corresponds to either the light-shielding area $134S_1$, $134S_2$, $134S_3$ and $134S_4$. Note, in FIG. 31, the light-shielding period, during which the fluorescent analog image-pixel signals are read from the CCD image sensor 14, is indicated by reference "$UVR_3$".

Note, the timing controller 74 is provided with a suitable frequency divider for producing the first, second and third series of timing-clock pulses on the basis of the basic timing-clock pulses used in the WL illumination mode.

Note, similar to the first embodiment, in the second embodiment, the image-signal processing circuit 56 is arranged as shown in FIG. 9.

As apparent from the timing chart of FIG. 31, the timing ($UVR_1$, $UVR_2$, $UVR_3$), at which fluorescent image-pixel signals are read from the CCD image sensor 14, coincides with the timing (GR), at which green image-pixel signals are read from the CCD image sensor 14 in the WL illumination mode, because the rotational frequency of the rotary color filter 124 is four times (integral multiples) greater than that of the rotary shutter 134. Thus, the fluorescent image-pixel signals, read from the CCD image sensor 14, can be processed in substantially the same manner as the green image-pixel signals read from the CCD image sensor 14 in the WL illumination mode. Accordingly, after the fluorescent image-pixel signals are converted by the A/D converter 64 (FIG. 9) into digital fluorescent image-pixel signals, these digital image-pixel signals are stored in the frame memory 66G. Therefore, in each of the first, second and third UV exposure modes, by operating the image-signal processing circuit 56 in the same manner as in the WL illumination mode, a fluorescent endoscope-image can be reproduced and displayed on the TV monitor 58 on the basis of a video signal component output from the final processing circuit 70G. In other words, it is possible to use the image-signal processing circuit 56 in common in the WL illumination mode, and first, second and third UV exposure modes, and it is therefore unnecessary to provide a separate image-processing circuit for the first, second and third UV exposure modes in the image-processing unit 12.

As is apparent from the timing chart of FIG. 31, in the first UV exposure mode, a frame of fluorescent digital image-pixel signals is renewed in the frame memory 66G every the one-frame period of 4/30 ms. Thus, the same frame of fluorescent digital image-pixel signals is read four times from the frame memory 66G during the one-frame period of 4/30 ms in accordance with the NTSC method. Accordingly, a fluorescent endoscope-image, reproduced and displayed on the TV monitor 58 in the first UV exposure mode, is awkward as a motion picture, but the reproduced fluorescent endoscope-image is clearest because the ultra-violet illumination period "$UVA_1$" is longest.

Also, in the second UV exposure mode, a frame of fluorescent digital image-pixel signals is renewed in the frame memory 66G every the one-frame period of 2/30 ms. Thus, the same frame of fluorescent digital image-pixel signals is read twice from the frame memory 66G during the one-frame period of 2/30 ms in accordance with the NTSC method. Accordingly, the motion of the fluorescent endoscope-image, reproduced and displayed on the TV monitor 58 in the second UV exposure mode, is somewhat improved in comparison to the first TV illumination, but the clarity of the reproduced fluorescent endoscope-image is reduced in comparison to the first LTV exposure mode, because the ultra-violet illumination period "$UVA_2$" is shorter than the ultra-violet illumination "$UVA_1$".

Further, in the third UV exposure mode, since a frame of fluorescent digital image-pixel signals is renewed in the frame memory 66G every the one-frame period of 1/30 ms, the motion of the fluorescent endoscope-image, reproduced and displayed on the TV monitor 58 in the third UV exposure mode, is natural, similar to a motion picture obtained by the NTSC method, but the clarity of the reproduced fluorescent endoscope-image is further reduced because the ultra-violet illumination period "$VA_3$" is shorter than in the first and second UV exposure modes.

In the second embodiment, it is necessary to set a different amplification factor to the preamplifier 60 in accordance with each selected illumination or exposure mode, because the CCD image sensor 14 exhibits a higher sensitivity to the red, green and blue light in comparison with the fluorescent light, and because the ultra-violet light illumination periods "$UVA_1$", "$UVA_2$" and "$UVA_3$" are different from each other. The setting of the amplification factor to the preamplifier 60 (FIG. 9) is altered by the system controller 72 whenever one of the WL illumination mode, and first, second and third UV exposure modes is selected.

Also, similar to the first embodiment, the amplified image-pixel signals, derived from the ultra-violet illumination, include higher frequency noise than that of the amplified image-pixel signals derived from the white light illumination. Thus, in the initial processing circuit 62, a noise-filtering circuit for the noise-elimination should be set such that the higher frequency noise is eliminated in each of the first, second and third UV exposure modes. The setting of the noise-filtering circuit is altered by the system controller 72 whenever one of the WL illumination mode, and first, second and third UV exposure modes is selected.

Further, in the initial processing circuit 62, a clamp circuit for the black-level-clamping should be set such that respective different black (pedestal) levels are obtained in the WL illumination mode, and first, second and third UV exposure modes, because the CCD image sensor 14 exhibits different sensitivities to the red, green and blue lights and the fluorescent light. The setting of the clamp circuit is altered by the system controller 72 whenever one of the WL illumination mode, and first, second and third UV exposure modes is selected.

Note, in FIG. 23, although a diaphragm for adjusting an amount of light directed from either the WL lamp 24 or the UV lamp 26 onto the proximal end of the optical light guide 18 is omitted, the diaphragm is incorporated in the light source device 19'.

In FIG. 22, reference 88' indicates a front panel provided on a housing of the image-signal processing unit 12, and various switch buttons and indicator windows are provided in the front panel 88'.

Figure 32:
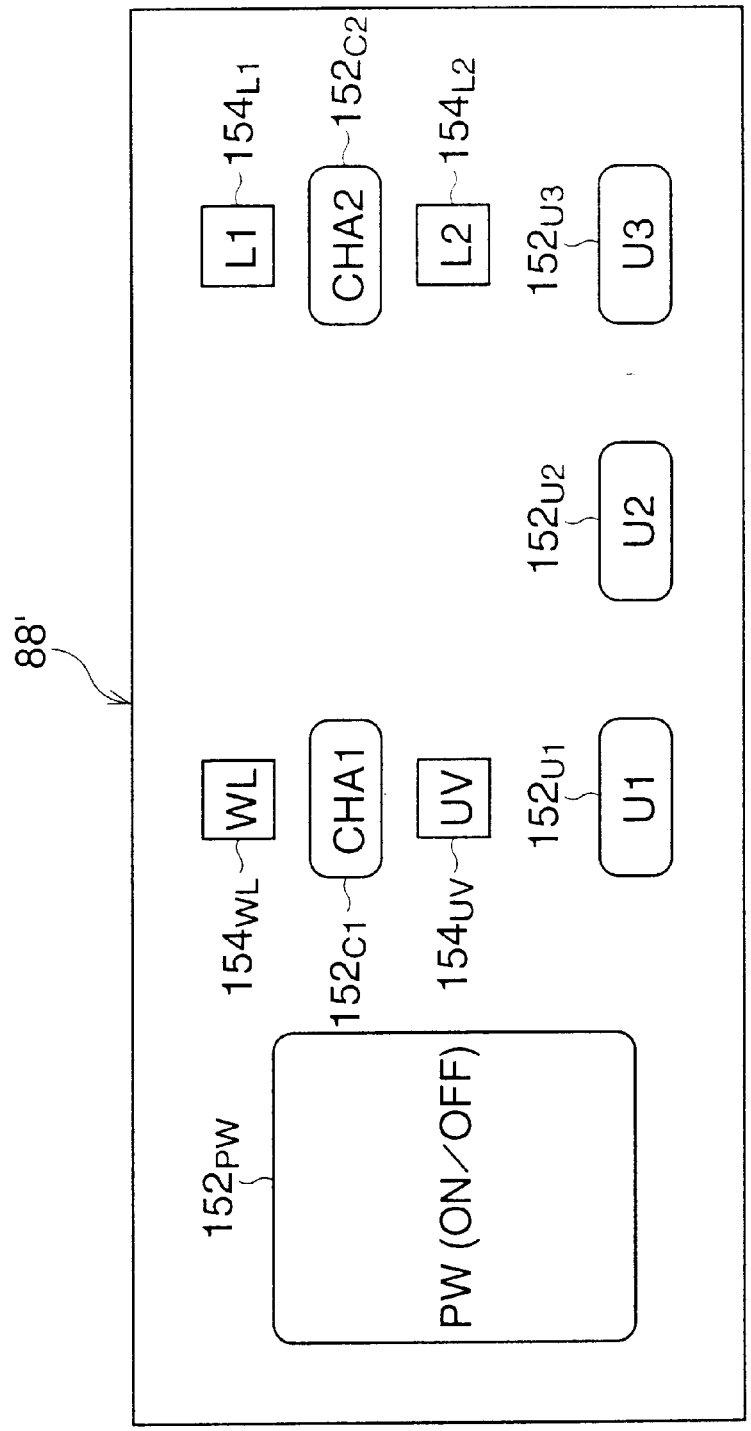
FIG. 32 is a front view showing a front panel of the image-signal processing unit.

With reference to FIG. 32, the front panel 88' is shown as a front view, and is provided with switch buttons $152_{PW}$, $152_{C1}$, $152_{C2}$, $152_{U1}$, $152_{U2}$ and $152_{U3}$ and indicator windows $154_{WL}$, $154_{UV}$, $154_{L1}$ and $154_{L2}$, which especially relate to the present invention.

Figure 33:
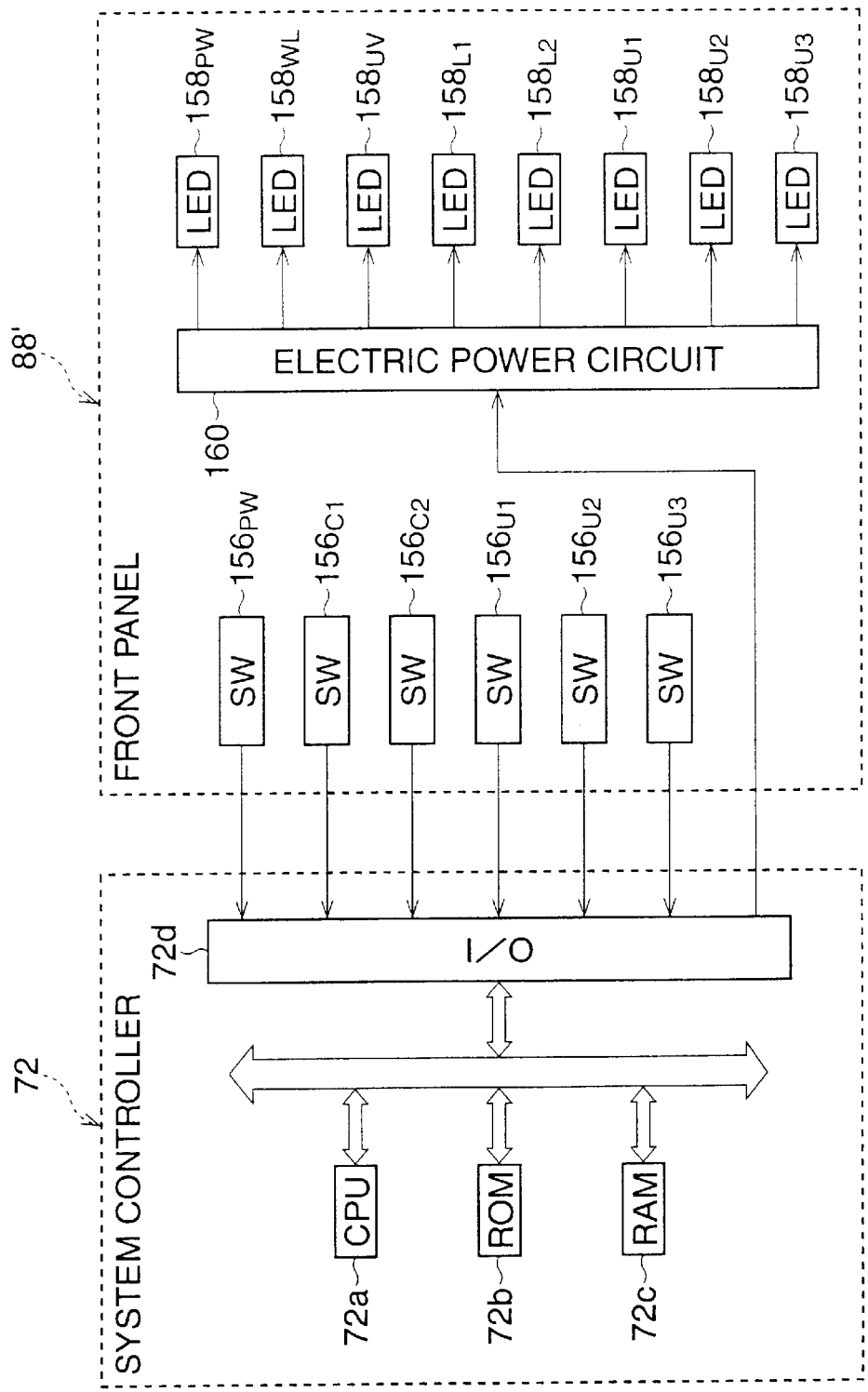
FIG. 33 is a block diagram showing a relationship between the system controller and the front panel in the second embodiment.

Also, with reference to FIG. 33, a relationship between the system controller 72 and the front panel 88' is shown as a block diagram. Note, in this drawing, the respective CPU, ROM, RAM and I/O of the system controller 72 are indicated by references 72a, 72b, 72c and 72d. The front panel 88' is provided with a printed circuit board having switches $156_{PW}$, $156_{C1}$, $156_{C2}$, $156_{U1}$, $156_{U2}$ and $156_{U3}$, which are connected to the I/O 72d. Also, the printed circuit board of the front panel 88' has light-emitting diodes (LED) $158_{PW}$, $156_{C1}$, $156_{C2}$, $156_{U1}$, $156_{U2}$ and $156_{U3}$, and an electric power circuit 160 for these LED's, which is operated under control of the system controller 72.

The switch button $152_{PW}$ is formed as a self-return type switch button, and is associated with the switch $156_{PW}$, which serves as a power ON/OFF switch. When the power ON/OFF switch $156_{PW}$ is in an OFF-state, it is turned ON by depressing the switch button $152_{PW}$. Also, when the power ON/OFF switch $156_{PW}$ is in the ON-state, it is turned OFF by depressing the switch button $152_{PW}$. When the power ON/OFF switch $156_{PW}$ is turned ON, a power source circuit (not shown) of the signal-processing unit 12 is supplied with electric power from a commercial power network.

The switch button $152_{PW}$ is made of a suitable translucent synthetic resin, and the LED $158_{PW}$ is arranged at the rear side of the switch button $152_{PW}$. When the power ON/OFF switch $156_{PW}$ is turned ON, the LED $158_{PW}$ is lit, thereby indicating that the power ON/OFF switch $156_{PW}$ is in the ON-state. When the power ON/OFF switch $156_{PW}$ is turned OFF, the LED $158_{PW}$ is put OFF, thereby indicating that the power ON/OFF switch $156_{PW}$ is in the OFF-state.

The switch button $152_{C1}$ is formed as a self-return type switch button, and is associated with the switch $156_{C1}$, which serves as an illumination-mode selection switch for selecting either the WL illumination mode or the UV illumination mode. The switch $156_{C1}$ is constituted to alternately output a high level signal or a low level signal to the system controller whenever the switch button $152_{C1}$ is depressed. When the high level signal is output from the illumination-mode selection switch $156_{C1}$, the system controller 72 recognizes that the WL illumination mode is selected. When the low level signal is output from the illumination-mode selection switch $156_{C1}$, the system controller 72 recognizes that the UV illumination mode is selected. Namely, whenever the switch button $152_{C1}$ is depressed, the WL and UV illumination modes are alternately selected.

Note, when the power ON/OFF switch $156_{PW}$ is turned ON, the high level signal is output from the illumination-mode selection switch $156_{C1}$, whereby the WL illumination mode is initially selected.

As shown in FIG. 32, the respective indicator windows $154_{WL}$ and $154_{UV}$ are placed adjacent to the upper and lower sides of the switch button 152c, and are made of a suitable translucent synthetic resin. The respective LED's $158_{WL}$ and $158_{UV}$ are arranged at the rear sides of the indicator windows $154_{WL}$ and $154_{UV}$. When the WL illumination mode is selected by the illumination-mode selection switch $156_{C1}$, only the LED $158_{WL}$ is lit, thereby indicating that the WL illumination mode is selected. When the UV illumination mode is selected by the illumination-mode selection switch $156_{C1}$, only the LED $158_{UV}$ is lit, thereby indicating that the UV illumination mode is selected.

The switch button $152_{C2}$ is formed as a self-return type switch button, and is associated with the switch $156_{C2}$, which serves as an OFF/reduction-mode selection switch for selecting either an OFF mode or an illumination reduction mode. Similar to the first embodiment, when one of the WL and UV illumination modes is selected, it is determined by the OFF/reduction-mode selection switch $156_{C2}$ whether a lamp (24, 26) used in the non-selected illumination mode should be completely turned OFF or the amount of light-emission therefrom should be reduced. Of course, when the OFF mode is selected, the lamp (24, 26) concerned is completely turned OFF, and when the illumination reduction mode is selected, the amount of light-emission from the lamp (24, 26) concerned is reduced.

Similar to the illumination-mode selection switch $156_{C1}$, the OFF/reduction-mode selection switch $156_{C2}$ alternately outputs a high level signal or a low level signal to the system controller whenever the switch button $152_{C2}$ is depressed. When the high level signal is output from the OFF/reduction-mode selection switch $156_{C2}$, the system controller 72 recognizes that the OFF mode is selected. When the low level signal is output from the OFF/reduction-mode selection switch $156_{C2}$, the system controller 72 recognizes that the illumination reduction mode is selected. Namely, whenever the switch button $152_{C2}$ is depressed, the OFF mode and the illumination reduction mode are alternately selected.

Note, when the power ON/OFF switch $156_{PW}$ is turned ON, the high level signal is output from the OFF/reduction-mode selection switch $156_{C2}$, whereby the OFF mode is initially selected.

As shown in FIG. 32, the respective indicator windows $154_{L1}$ and $154_{L2}$ are placed adjacent to the upper and lower sides of the switch button $152_{C2}$, and are made of a suitable translucent synthetic resin. The respective LED's $158_{L1}$ and $158_{L2}$ are arranged at the rear sides of the indicator windows $154_{L1}$ and $154_{L2}$. When the OFF mode is selected by the OFF/reduction-mode selection switch $156_{C2}$ only the LED $158_{L1}$ is lit, thereby indicating that the OFF mode is selected. When the illumination reduction mode is selected by the OFF/reduction-mode selection switch $156_{C2}$, only the LED $158_{L2}$ is lit, thereby indicating that the illumination reduction mode is selected.

Each of the switch buttons $152_{U1}$, $152_{U2}$ and $152_{U3}$ is formed as a self-return type switch button, and the respective switch buttons $152_{U1}$, and $152_{U2}$ and $152_{U3}$ are associated with the switches $156_{U1}$, $156_{U2}$ and $156_{U3}$ for selecting either the first, second or third UV exposure modes. Namely, the switch $156_{U1}$ serves as a first UV-exposure-mode selection switch; the switch $156_{U2}$ serves as a second UV-exposure-mode selection switch; and the switch $156_{U3}$ serves as a third UV-exposure-mode selection switch.

Only while each of the switch buttons $152_{U1}$, $152_{U2}$ and $152_{U3}$ is depressed, an output level of a corresponding UV-exposure-mode selection switch ($156_{U1}$, $156_{U2}$, $156_{U3}$) is changed from a low level to a high level. As soon as the switch button concerned is released from the depression, the output level of the corresponding UV-exposure-mode selection switch immediately reverts from the high level to the low level. In short, only while each of the switch buttons $152_{U1}$ and $152_{U2}$ and $152_{U3}$ is depressed, the corresponding UV-exposure-mode selection switch ($156_{U1}$, $156_{U2}$, $156_{U3}$) outputs a high level signal to the system controller 72.

While the WL illumination mode is selected, the first, second and third UV-exposure-mode selection switches $156_{U1}$, $156_{U2}$ and $156_{U3}$ are disabled. The first, second and third UV-exposure-mode selection switches $156_{U1}$, $156_{U2}$ and $156_{U3}$ are enabled only while the UV illumination mode is selected. During the selection of the UV illumination mode, the system controller 72 monitors which switch ($156_{U1}$, $156_{U2}$, $156_{U3}$) outputs the high level signal. When the high level signal is output from the first UV-exposure-mode selection switch $156_{U1}$ the system controller 72 recognizes that the first UV exposure mode is selected. When the high level signal is output from the second UV-exposure-mode selection switch $156_{U2}$, the system controller 72 recognizes that the second UV exposure mode is selected. When the high level signal is output from the third UV-exposure-mode selection switch $156_{U3}$, the system controller 72 recognizes that the third UV exposure mode is selected.

Each of the switch buttons $152_{U1}$, $152_{U2}$ and $152_{U3}$ is made of a suitable translucent synthetic resin, and the respective LED's $158_{U1}$, $158_{U2}$ and $158_{PW}$ are arranged at the rear sides of the switch buttons $152_{U3}$, $152_{U2}$ and $152_{U3}$. When the switch button $152_{U1}$ is depressed, only the LED $158_{U1}$ is lit, thereby indicating that the first UV exposure mode is selected. When the switch button $152_{U2}$ is depressed, only the LED $158_{U2}$ is lit, thereby indicating that the second UV exposure mode is selected. When the switch button $152_{U3}$ is depressed, only the LED $158_{U3}$ is lit, thereby indicating that the third UV exposure mode is selected.

As stated hereinafter, at the initial stage, the rotary shutter 134 is positioned at the first operative position. Thus, when the UV illumination mode is first selected after the power ON/OFF switch $156_{PW}$ is turned ON, the first UV exposure mode is initially selected, with only the LED $158_{U1}$ being lit.

Figure 34:
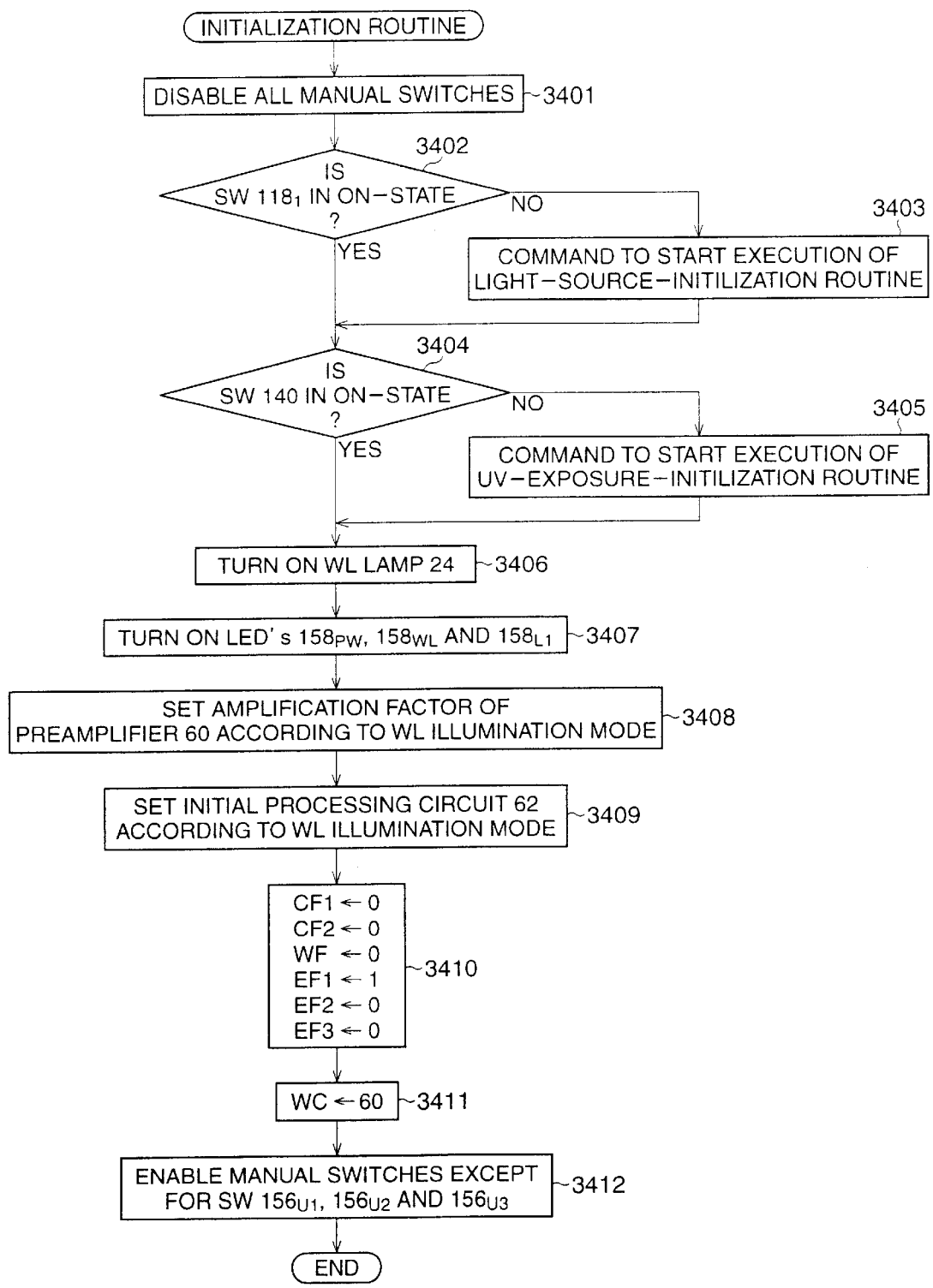
FIG. 34 is a flowchart of an initialization routine executed in the second embodiment.

FIG. 34 shows a flowchart of an initialization routine, which is only-executed once by the system controller 72 in the second embodiment, when the power ON/OFF switch $152_{PW}$ is turned ON.

At step 3401, all the manual switches (except for the power ON/OFF switch $152_{PW}$), provided on the front panel 88', are disabled.

At step 3402, it is determined whether the first limit switch 1181 of the driving-mechanism 116 for the mirror 114 is in an ON-state, i.e. whether the mirror 114 is positioned at the first operative position. When it is confirmed that the mirror 114 is not positioned at the first operative position, the control proceeds to step 3403, in which stating execution of a light-source-initialization routine is commanded to move the mirror 114 to the first operative position. As mentioned above, the mirror 114 is initially positioned at the first operative position because the WL illumination is forcibly selected at the initial stage. Note, the light-source-initialization routine is explained hereinafter with reference to FIG. 35.

In either case, at step 3404, it is determined whether the limit switch 140 is an ON-state, i.e. whether the rotary shutter 134 is positioned at the first operative position. When it is confirmed that the mirror 114 is not positioned at the first operative position, the control proceeds to step 3405, in which starting execution of a UV-exposure-initialization routine is commanded to move the rotary shutter 134 to the first operative position. As mentioned above, the rotary shutter 134 is initially positioned at the first operative position, because the first UV-exposure mode is forcibly selected when the WL illumination mode is first switched to the UV illumination mode. Note, the UV-exposure-initialization routine is explained hereinafter with reference to FIG. 36.

At step 3406, the WL lamp 24 is turned ON. Then, at step 3407, the LED's $158_{PL}$, $158_{WL}$ and $158_{L1}$ are turned ON. Of course, the turn-ON of the LED $158_{PW}$ indicates that the image-signal processing unit 12 is electrically powered ON, the turn-ON of the LED $158_{WL}$ indicates that the WL illumination mode is selected, and the turn-ON of the LED $158_{L1}$ indicates that the OFF mode is selected.

At step 3408, the amplification factor of the preamplifier 60 is set in accordance with the WL illumination mode. Then, at step 3409, the initial processing circuit 62 is set in accordance with the WL illumination mode.

At step 3410, an illumination-mode-indication flag CF1, an OFF/reduction-mode-indication flag CF2 and a standby-indication flag WF are initialized to "0". Also, at step 3410, a first UV-exposure-mode-indication flag EF1 is initialized to "1", and second and third UV-exposure-mode-indication flags EF2 and EF3 are initialized to "0".

The illumination-mode-indication flag CF1 is provided to indicate whether the WL illumination mode or the UV illumination mode is selected. If CF1=0, the flag CF1 indicates that the WL illumination mode is selected. If CF1=1, the flag CF1 indicates that the UV illumination mode is selected. As stated above, at the initial stage, since the WL illumination mode is forcibly selected, the flag CF1 is initialized to "0".

The OFF/reduction-mode-indication flag CF2 is provided to indicate whether the OFF mode or the illumination reduction mode is selected. If CF2=0, the flag CF2 indicates that the OFF mode is selected. If CF2=1, the flag CF2 indicates that the illumination reduction mode is selected. As stated above, at the initial stage, since the OFF mode is forcibly selected, the flag CF2 is initialized to "0".

The standby-indication flag WF is provided to indicate whether the switching of the WL illumination mode to the UV illumination mode and vice versa, has been completed when the illumination-mode selection switch button $152_{C1}$ is operated, as explained in detail hereinafter with reference to an illumination-mode-selection-switch-monitoring routine shown in FIG. 38. Also, the standby-indication flag WF is used to indicate whether selecting one of the first, second and third UV-exposure modes has been completed when one of the first, second and third UV-exposure-mode selection switches $156_{U1}$, $156_{U2}$ and $156_{U3}$ is operated, as explained in detail hereinafter with reference to a UV-exposure-selection-monitoring routine shown in FIG. 41.

The first UV-exposure-mode-indication flag EF1 is provided to indicate whether the first UV-exposure mode is selected. If EF1=0, the flag EF1 indicates that the first UV-exposure mode is not selected. If EF1=1, the flag EF1 indicates that the first UV-exposure mode is selected. As stated above, since the first UV-exposure mode is forcibly selected when the WL illumination mode is first switched to the UV illumination mode, the UV-exposure-mode-indication flag EF1 is initialized to "1" (step 3410).

The second UV-exposure-mode-indication flag EF2 is used to indicate whether the second UV-exposure mode is selected. If EF2 =0, the flag EF2 indicates that the second UV-exposure mode is not selected. If EF2=1, the flag EF2 indicates that the second UV-exposure mode is selected.

The third UV-exposure-mode-indication flag EF2 is used to indicate whether the third UV-exposure mode is selected. If EF3 =0, the flag EF3 indicates that the third UV-exposure mode is not selected. If EF3=1, the flag EF3 indicates that the third UV-exposure mode is selected.

At step 3411, a standby-time counter WC is initialized to "60". Note, the standby-time counter WC is provided for counting a time period of 3 sec, as stated in detail hereinafter.

At step 3412, all the manual switches except for the first, second and third UV-exposure-mode selection switches $156_{U1}$, $156_{U2}$ and $156_{U3}$ are enabled.

Figure 35:
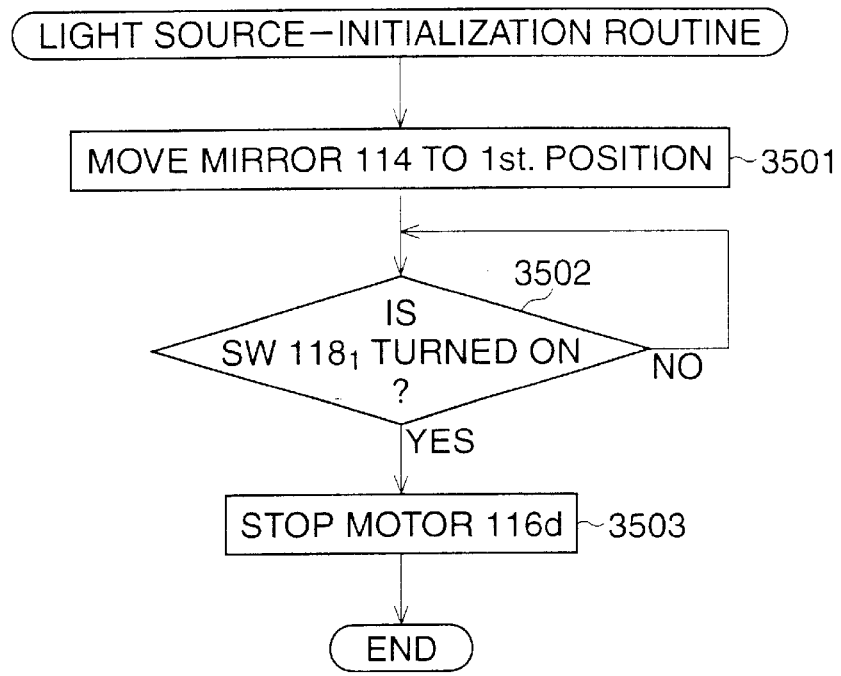
FIG. 35 is a flowchart of a light-source-initialization routine executed in the second embodiment.

FIG. 35 shows a flowchart of the aforesaid light-source-initialization routine, which is executed in the system controller 72 after being commanded at step 3403 of the initialization routine of FIG. 34.

At step 3501, the motor 116d is driven such that the mirror 114 is moved toward the first operative position. Then, at step 3502, it is monitored at suitable regular intervals of, for example, 50 ms whether the first limit switch 118l has been turned ON. When it is confirmed that the first limit switch 118l is turned ON, the control proceeds to step 3503, in which the motor 116d is stopped, thereby positioning the mirror 114 at the first operative position.

Figure 36:
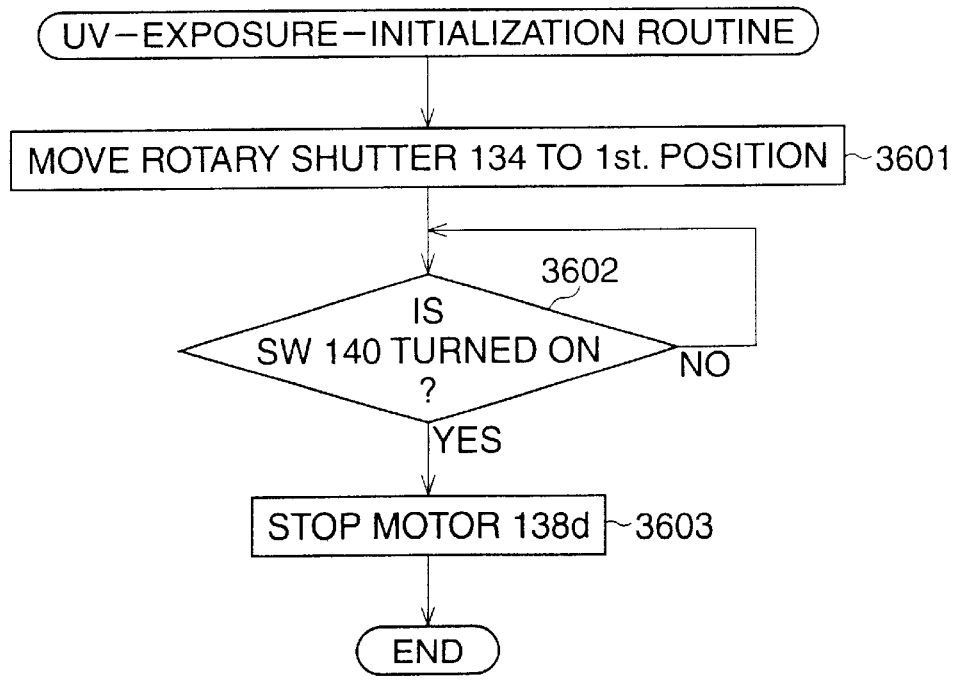
FIG. 36 is a flowchart of a UV-exposure-initialization routine executed in the second embodiment.

FIG. 36 shows a flowchart of the aforesaid UV-exposure-initialization routine, which is executed in the system controller 72 after being commanded at step 3405 of the initialization routine of FIG. 34.

At step 3601, the motor 138d is driven such that the rotary shutter 134 is moved toward the first operative position. Then, at step 3602, it is monitored at suitable regular intervals of, for example, 50 ms whether the limit switch 140 has been turned ON. When it is confirmed that the limit switch 140 is turned ON, the control proceeds to step 3603, in which the motor 138d is stopped, thereby positioning the rotary shutter 134 at the first operative position.

Figure 37:
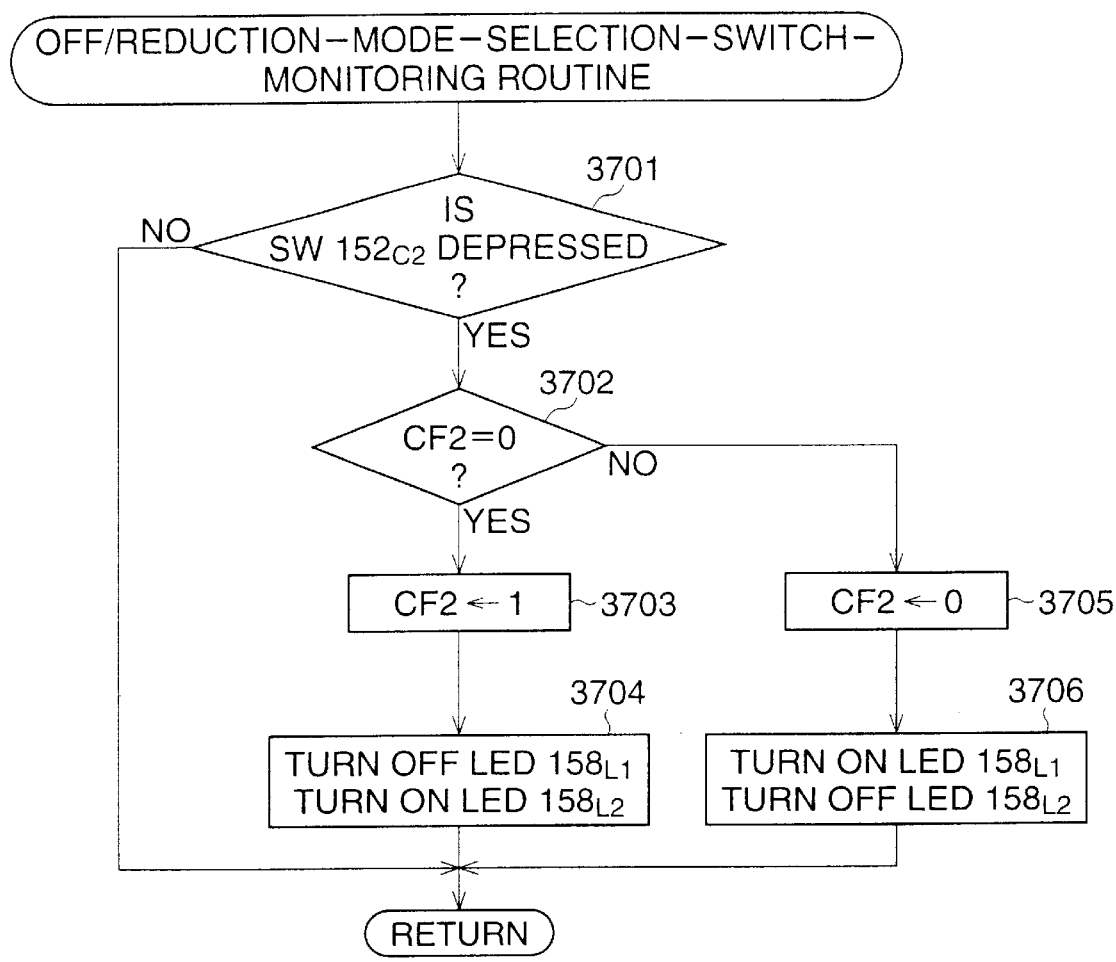
FIG. 37 is a flowchart of an OFF/reduction-mode-selection-switch-monitoring routine executed in the second embodiment.

FIG. 37 is a flowchart of an OFF/reduction-mode-selection-switch-monitoring routine, which is formed as a time-interruption routine executed in the system controller 72 at regular suitable intervals of, for example, 50 ms. Note that the execution of the OFF/reduction-mode-selection-switch-monitoring routine is consecutive to the initialization routine of FIG. 34, and is repeated every 50 ms as long as the power ON/OFF switch $156_{PW}$ is turned ON.

At step 3701, it is monitored whether the switch button $152_{C2}$ has been depressed. If depression of the switch button $152_{C2}$ is not detected, the routine immediately ends. Although the routine is repeatedly executed every 50 ms, there in no progress until depression of the switch button $152_{C2}$ is confirmed.

At step 3701, when depression of the switch button $152_{C2}$ is confirmed, the control proceeds to step 3702, in which it is determined whether the OFF/reduction-mode-indication flag. CF2 is "0" or "1".

If CF2=0, i.e. if the OFF mode is selected, the control proceeds to step 3703, in which the flag CF2 is set to "1", thereby indicating that the illumination reduction mode is selected. Then, at step 3704, the LED $158_{L1}$ is turned OFF, and the LED $158_{L2}$ is turned ON, thereby visually indicating that the illumination reduction mode is selected.

At step 3702, if CF2=1, i.e. if the illumination reduction mode is selected, the control proceeds from step 3702 to step 3705, in which the flag CF2 is set to "0", thereby indicating that the OFF mode is selected. Then, at step 3706, the LED $158_{L1}$ is turned ON, and the LED $158_{L2}$ is turned OFF, thereby visually indicating that the OFF mode is selected.

Figure 38:
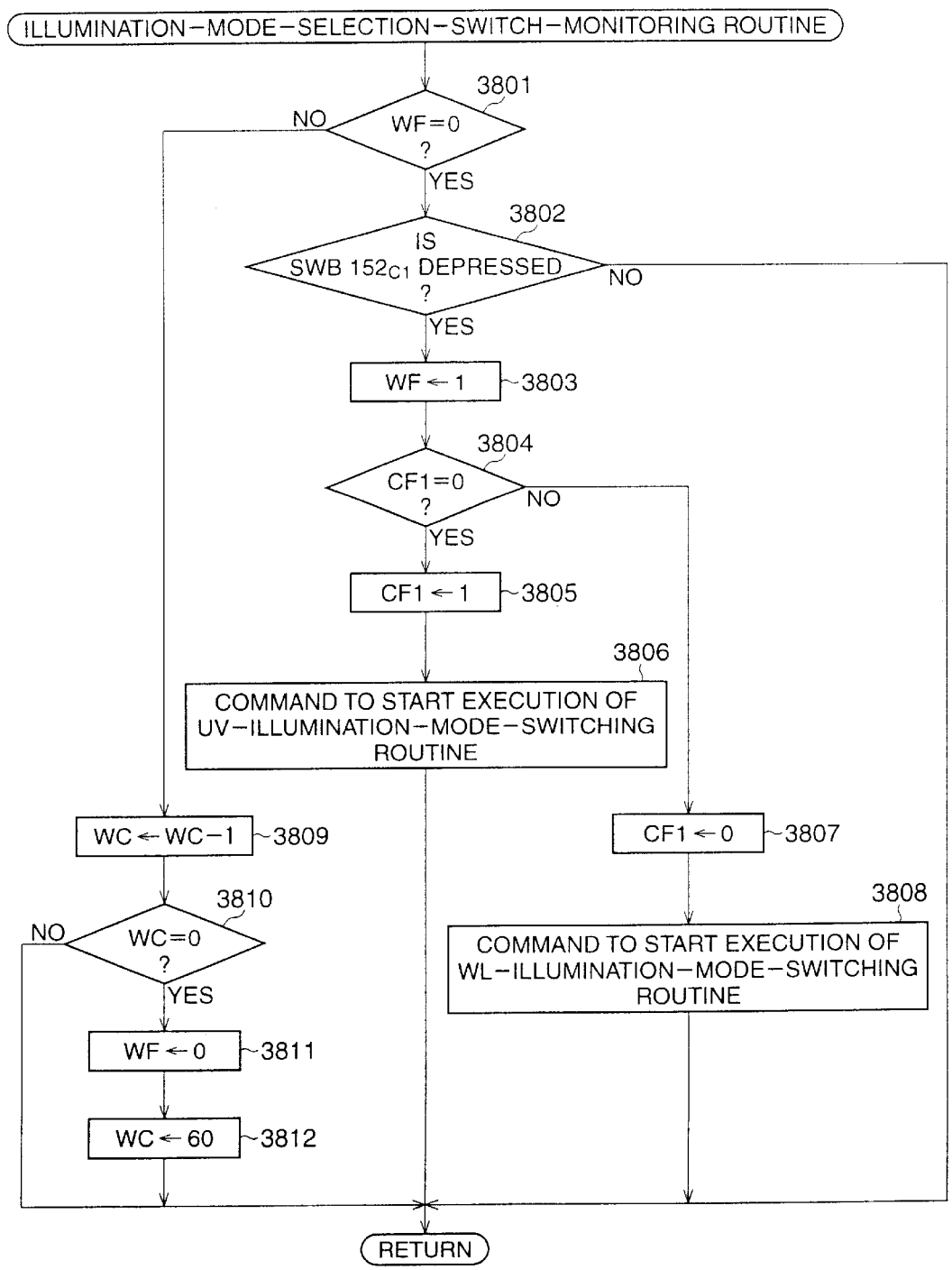
FIG. 38 is a flowchart of an illumination-mode-selection-switch-monitoring routine executed in the second embodiment.

FIG. 38 is a flowchart of the aforesaid illumination-mode-selection-switch-monitoring routine, which is formed as a time-interruption routine executed in the system controller 72 at regular suitable intervals of, for example, 50 ms. Note that the execution of the illumination-mode-selection-switch-monitoring routine is consecutive to the initialization routine of FIG. 34, and is repeated every 50 ms as long as the power ON/OFF switch $156_{PW}$ is turned ON.

At step 3801, it is determined whether the standby-indication flag WF is "0" or "1". At the initial stage, since WF =0 (step 3410), the control proceeds to step 3802, in which it is monitored whether the switch button $152_{C1}$ has been depressed. If depression of the switch button $152_{C3}$ is not detected, the routine immediately ends. Although the routine is repeatedly executed every 50 ms, there in no progress until depression of the switch button $152_{C1}$ is confirmed.

At step 3802, when the depression of the switch button $152_{C1}$ is confirmed, the control proceeds to step 3803, in which the standby-indication flag WF is set to "1". Then, at step 3804, it is determined whether the illumination-mode-indication flag CF1 is "0" or "1".

If CF1=0, i.e. if the WL illumination mode is selected, the control proceeds to step 3805, in which the flag CF1 is set to "1", thereby indicating that the UV illumination mode is selected. Then, at step 3806, stating execution of a UV illumination-modes-witching routine is commanded, and the routine ends. Note, the UV-illumination-modes-witching routine is explained in detail hereinafter with reference to FIG. 39.

At step 3804, if CF1=1, i.e. if the UV illumination mode is selected, the control proceeds from step 3804 to step 3807, in which the flag CF1 is set to "0", thereby indicating that the WL illumination mode is selected. Then, at step 3808, starting execution of a WL-illumination-modes-witching routine is commanded, and the routine ends. Note, the WL-illumination-modes-witching routine is explained in detail hereinafter with reference to FIG. 40.

After the flag WF is set to "1" (step 3803), the control proceeds from step 3801 to step 3809 (WF=1,), in which the value of the standby-time counter WC, which has a setting of "60" as the initial value (step 3411), is decremented by "1". Then, at step 3810, it is determined whether the value of the counter WC has reached "0". If WC>0, the control skips steps 3811 and 3812, and thus the routine ends. Thereafter, although the routine is repeatedly executed every 50 ms, there is no progress until the counter WC reaches "0".

At step 3810, when it is confirmed that the value of the counter WC has reached "0", i.e. when it is confirmed that a time period of 3 sec (50 ms×60) has elapsed, the control proceeds from step 3810 to step 3811, in which the standby-indication flag WF is set to "0". Then, at step 3812, the standby-time counter WC is reset to "60", and the routine ends.

Figure 39:
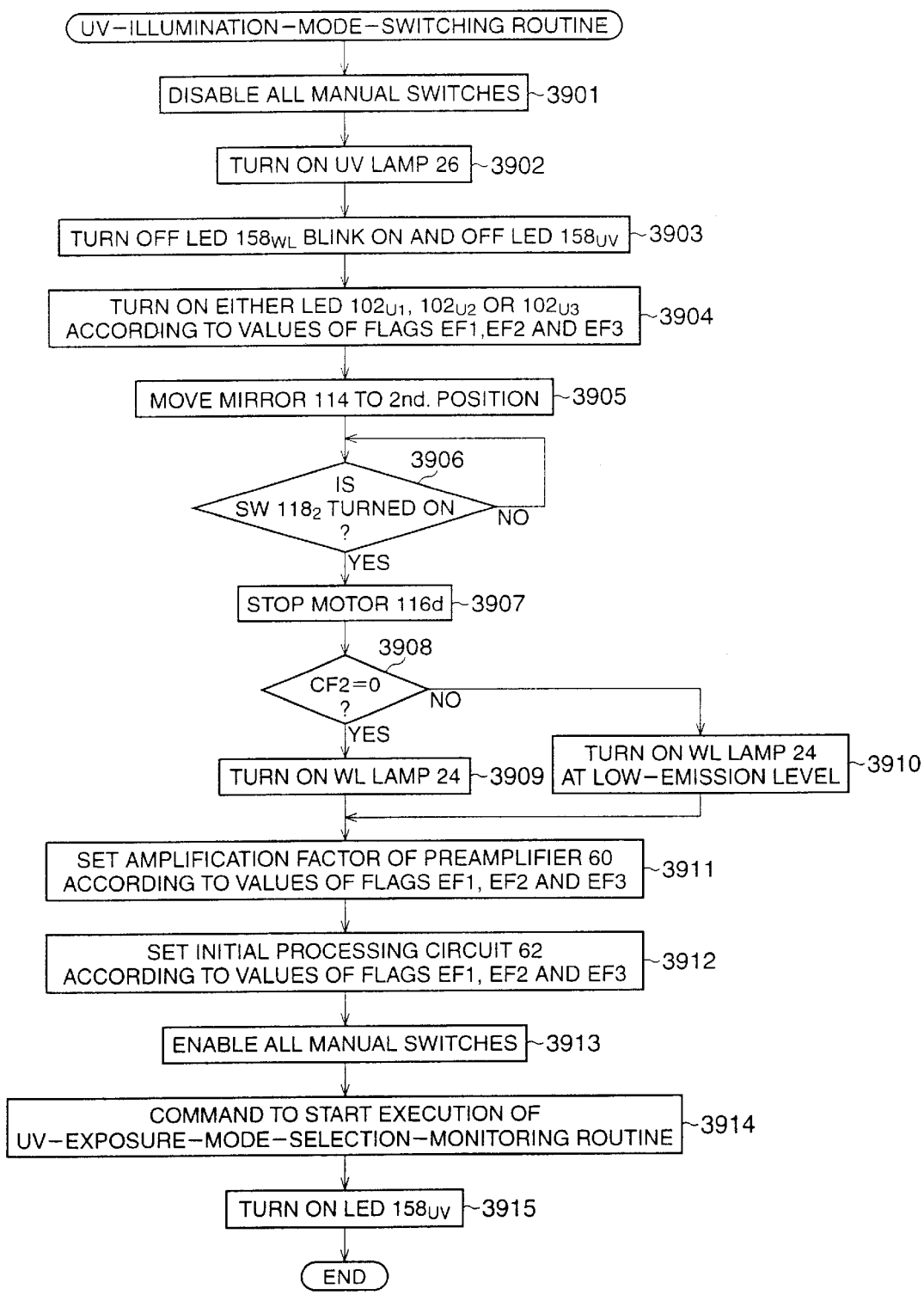
FIG. 39 is a flowchart of a UV-illumination-mode-switching routine executed in the second embodiment.
Figure 40:
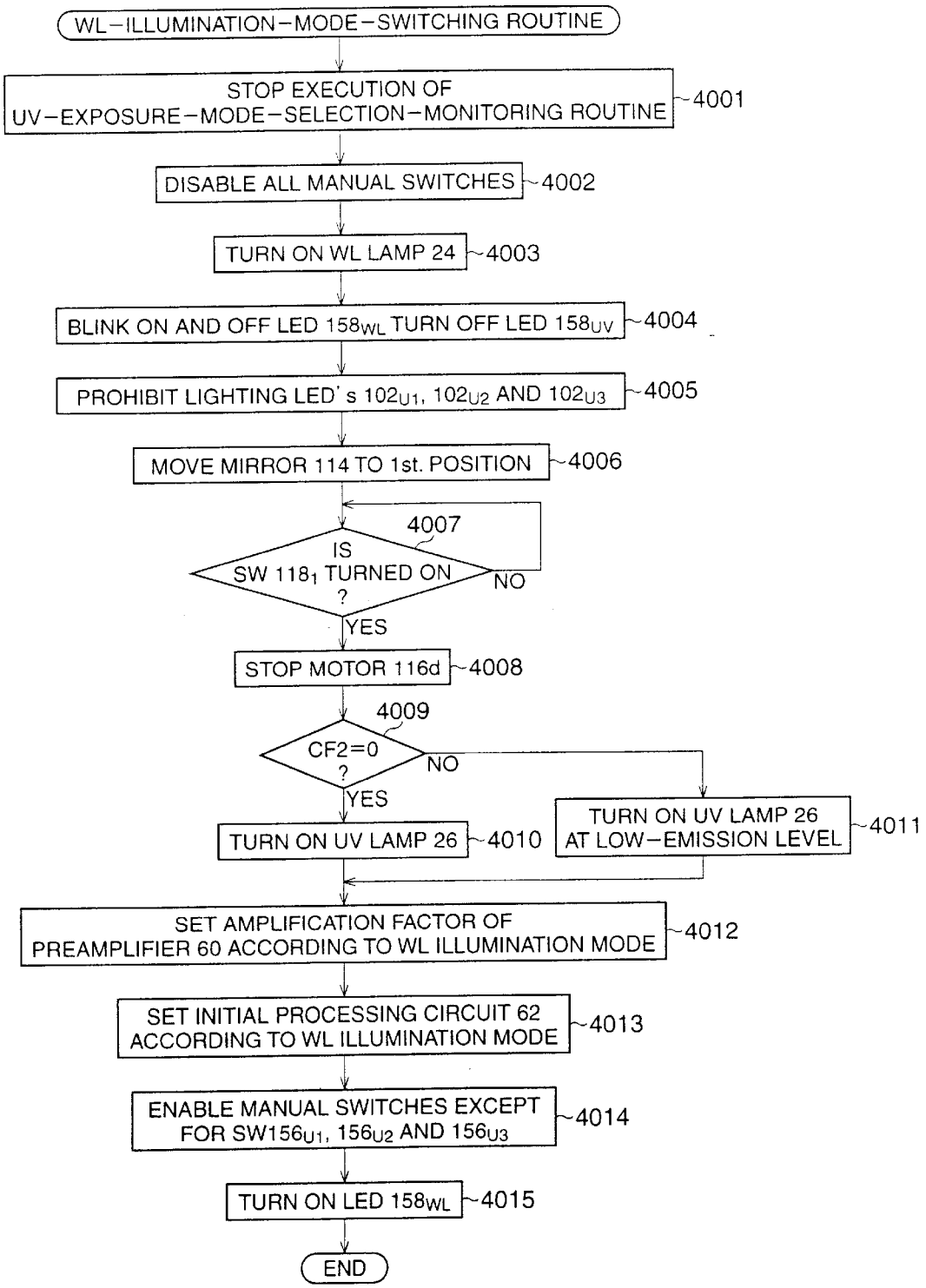
FIG. 40 is a flowchart of a WL-illumination-mode-switching routine executed in the second embodiment.

In short, during the elapse of the 3 sec time period, either the UV-illumination-modes-witching routine shown in FIG. 39 or the WL-illumination-modes-witching routine shown in FIG. 40 is executed (step 3806 or step 3808). Namely, the 3 sec time period is enough to complete the switching from the WL illumination mode to the UV illumination mode and vice versa.

FIG. 39 is a flowchart of the aforesaid UV-illumination-modes-witching routine, which is executed in the system controller 72 after being commanded at step 3806 of the illumination-mode-selection-switch-monitoring routine of FIG. 38.

At step 3901, all the manual switches (except for the power ON/OFF switch $152_{PW}$), provided on the front panel 88', are disabled. Then, at step 3902, the UV lamp 26 is turned ON. Subsequently, at step 3903, the LED $158_{WL}$ is turned OFF, and the LED $158_{UV}$ is blinked ON and OFF, thereby indicating that the WL illumination mode is being switched to the UV illumination mode.

At step 3904, either the LED $158_{U1}$, $158_{U2}$ or $158_{U3}$ is turned ON in accordance with values of the first, second and third UV-exposure-mode-indication flags EF1, EF2 and EF3. Namely, if EF1 =1, EF2=0 and EF3=0, i.e. if the first UV-exposure mode is selected, only the LED $158_{U1}$ is turned ON; if EF1=0, EF2=1, and EF3=0, i.e. if the second UV-exposure mode is selected, only the LED $158_{U2}$ is turned ON; and if EF1=0, EF2=0 and EF3=1, i.e. if the third UV-exposure mode is selected, only the LED $158_{U3}$ is turned ON.

At step 3905, the motor 116d is driven such that the mirror 114 is moved from the first operative position toward the second operative position. Then, at step 3906, it is monitored at suitable regular intervals of, for example, 50 ms whether the second limit switch 1182 has been turned ON. When it is confirmed that the second limit switch 1182 is turned ON, the control proceeds to step 3907, in which the motor 116d is stopped, thereby positioning the mirror 114 at the second operative position.

At step 3908, it is determined whether the OFF/reduction-mode-indication flag CF2 is "0" or "1". If CF2=0, i.e. if the OFF mode is selected, the control proceeds to step 3909, in which the WL lamp 24 is turned OFF. At step 3908, if CF2=1, i.e. if the illumination reduction mode is selected, the control proceeds to step 3910, in which the WL lamp 24 is turned ON at a low-light-emission level, whereby the WL lamp 24 is lit such that the amount of light-emission therefrom is reduced.

At step 3911, the amplification factor of the preamplifier 60 is set in accordance with the values of the first, second and third UV-exposure-mode-indication flags EF1, EF2 and EF3. Namely, if the first UV-exposure mode is selected (EF1=1, EF2=0 and EF3 =0), the setting of the factor is performed in accordance with the first UV-exposure mode; if the second UV-exposure mode is selected (EF1=0, EF2=1, and EF3=0) the setting of the factor is performed in accordance with the second UV-exposure mode; and if the third UV-exposure mode is selected (EF1=0, EF2=0 and EF3=1), the setting of the factor is performed in accordance with the third UV-exposure mode.

At step 3912, the initial processing circuit 62 is set in accordance with the values of the first, second and third UV-exposure-mode-indication flags EF1, EF2 and EF3. Namely, if the first UV-exposure mode is selected (EF1=1, EF2=0 and EF3=0), the setting of the circuit 62 is performed in accordance with the first UV-exposure mode; if the second UV-exposure mode is selected (EF0, EF2=1 and EF3=0), the setting of the circuit 62 is performed in accordance with the second UV-exposure mode; and if the third UV-exposure mode is selected (EF1=0, EF2=0 and EF3 =1), the setting of the circuit 62 is performed in accordance with the third UV-exposure mode.

At step 3913, all the manual switches are enabled. Then, at step 3914, stating the execution of the UV-exposure-mode-selection routine (FIG. 41) is commanded. Subsequently, at step 3915, the binked LED $158_{UV}$ is turned ON, thereby indicating that the WL illumination mode has been switched to the UV illumination mode.

FIG. 40 is a flowchart of the aforesaid WL-illumination-modes-witching routine, which is executed in the system controller 72 after being-commanded at step 3808 of the illumination-mode-selection-switch-monitoring routine of FIG. 38.

At step 4001, stating the execution of the UV-exposure-mode-selection routine (FIG. 41) is commanded, because the UV-exposure-mode-selection routine is necessary only when the UV-illumination mode is selected.

At step 4002, all the manual switches (except for the power ON/OFF switch $152_{PW}$), provided on the front panel 88', are disabled. At step 4003, the WL lamp 24 is turned ON. Then, at step 4004, the LED $158_{WL}$, is blinked ON and OFF, and the LED $158_{UV}$ is turned OFF, thereby indicating that the UV illumination mode is being switched to the WL illumination mode. Subsequently, at step 4005, the LED's $158_{U1}$, $158_{U2}$ and $158_{U3}$ are prohibited from being lit.

At step 4006, the motor 116d is driven such that the mirror 114 is moved from the second operative position toward the first operative position. Then, at step 4007, it is monitored at suitable regular intervals of, for example, 50 ms whether the first limit switch $118_1$ has been turned ON. When it is confirmed that the first limit switch $118_1$ is turned ON, the control proceeds to step 4008, in which the motor 116d is stopped, thereby positioning the mirror 114 at the first operative position.

At step 4009, it is determined whether the OFF/reduction-mode-indication flag CF2 is "0" or "1". If CF2=0, i.e. if the OFF mode is selected, the control proceeds to step 4010, in which the UV lamp 26 is turned OFF. At step 4009, if CF2=1, i.e. if the illumination reduction mode is selected, the control proceeds to step 4011, in which the UV lamp 26 is turned ON at a low-light-emission level, i.e. the UV lamp 26 is lit such that the amount of light-emission therefrom is reduced.

At step 4012, the amplification factor of the preamplifier 60 is set in accordance with the WL illumination mode. Then, at step 4013, the initial processing circuit 62 is set in accordance with the WL illumination mode.

At step 4014, all the manual switches are enabled. Then, at step 4015, the blinked LED $158_{WL}$ is continuously turned ON, thereby indicating that the LTV illumination mode has beer switched to the WL illumination mode.

Figure 41:
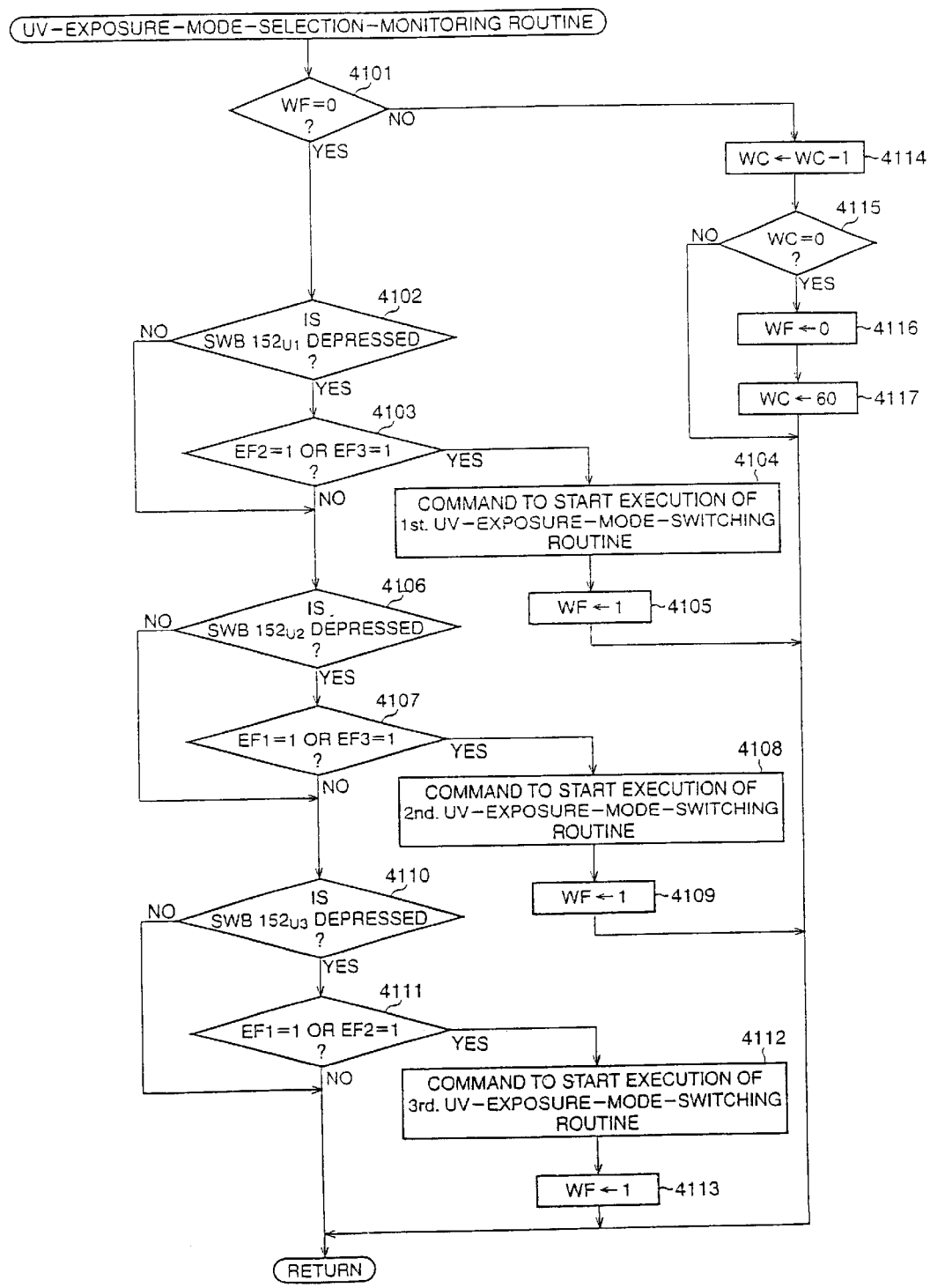
FIG. 41 is a flowchart of a UV-exposure-mode-selection-monitoring routine executed in the second embodiment.

FIG. 41 is a flowchart of the aforesaid UV-exposure-mode-selection-monitoring routine, which is formed as a time-interruption routine executed in the system controller 72 at regular suitable intervals of, for example, 50 ms. Note that this routine is executed after being commanded at step 3914 of the TV-illumination-modes-witching-monitoring routine of FIG. 39, and the execution is stopped after being commanded at step 4001 of the WL-illumination-modes-witching-monitoring routine of FIG. 40.

At step 4101, it is determined whether the standby-indication flag WF is "0" or "1". At the initial stage, since WF=0 (step 3410); the control proceeds to step 4102, in which it is monitored whether the switch button 152$_{U1}$ has been depressed. When depression of the switch button 152$_{U1}$ is not detected, the control skips step 4103 to step 4106, in which it is monitored whether the switch button 152$_{U2}$ has been depressed. When depression of the switch button 152$_{U2}$ is not detected, the control skips step 4107 to step 4110, in which it is monitored whether the switch button 152$_{U3}$ has been depressed. When depression of the switch button 152$_{U3}$ is not detected, the routine ends. In short, every 50 ms, it is monitored whether either switch button 152$_{U1}$, 152$_{U2}$ or 152$_{U3}$ has been depressed.

At step 4102, when the depression of the switch button 152$_{U1}$ is confirmed, the control proceeds to step 4103, it is determined whether either the second UV-exposure-mode-indication flag EF2 or the third UV-exposure-mode-indication flag EF3 is "1". If EF2=1 (i.e. the second UV-exposure mode is selected) or if EF3=1, (i.e. the third UV-exposure mode is selected), the control proceeds to step 4104, in which starting execution of a first UV-exposure-modes-witching routine is commanded. Then, at step 4105, the standby-indication flag WF is set to "1". Note that the first UV-exposure-modes-witching routine is explained in detail hereinafter with reference to FIG. 42.

At step 4103, if both the flags EF2 and EF3 are "0", i.e. if the flag EF1 is "1", the control proceeds to step 4106. Namely, the depression of the switch button 152$_{U1}$ (step 4102) is ignored because the first UV-exposure mode is already selected (EF1=1).

At step 4106, when the depression of the switch button 152$_{U2}$ is confirmed, the control proceeds to step 4107, it is determined whether either the first UV-exposure-mode-indication flag EF1 or the third UV-exposure-mode-indication flag EF3 is "1". If EF1=1 (i.e. the first UV-exposure mode is selected) or if EF3=1, (i.e. the third UV-exposure mode is selected), the control proceeds to step 4108, in which starting execution of a second UV-exposure-modes-witching routine is commanded. Then, at step 4109, the standby-indication flag WF is set to "1". Note that the second UV-exposure-modes-witching routine is explained in detail hereinafter with reference to FIG. 43.

At step 4107, if both the flags EF1 and EF3 are "0", i.e. if the flag EF2 is "1", the control proceeds to step 411. Namely, the depression of the switch button 152$_{U2}$ (step 4106) is ignored because the second UV-exposure mode is already selected (EF2=1).

At step 4110, when the depression of the switch button 152$_{U3}$ is confirmed, the control proceeds to step 4111, it is determined whether either the first UV-exposure-mode-indication flag EF1 or the second UV-exposure-mode-indication flag EF2 is "1". If EF1 =1, (i.e. the first UV-exposure mode is selected) or if EF2=1, (i.e. the third UV-exposure mode is selected), the control proceeds to step 4112, in which starting execution of a third UV-exposure-modes-witching routine is commanded. Then, at step 4113, the standby-indication flag WF is set to "1". Note that the third UV-exposure-modes-witching routine is explained in detail hereinafter with reference to FIG. 44.

At step 4111, if both the flags EF1 and EF2 are "0", i.e. if the flag EF3 is "1", the control ends. Namely, the depression of the switch button 152$_{U3}$ (step 4110) is ignored because the third UV-exposure mode is already selected (EF3=1).

After the setting of "1" is given to the flag WF at either step 4105, 4109 or 4113, the control proceeds from step 4101 to step 4114 (WF=1), in which the value of the standby-time counter WC, which has a setting of "60" as the initial value (step 3411), is decremented by "1". Then, at step 4115, it is determined whether the value of the counter WC has reached "0". If WC>0, the control skips steps 4116 and 4117, and thus the routine ends. Thereafter, although the routine is repeatedly executed every 50 ms, there is no progress until the counter WC reaches "0".

At step 4115, when it is confirmed that the value of the counter WC has reached "0", i.e. when it is confirmed that a time period of 3 sec (50 ms×60) has elapsed, the control proceeds from step 4115 to step 4116, in which the standby-indication flag WF is set to "0". Then, at step 4117, the standby-time counter WC is reset to "60", and the routine ends.

In short, during the elapse of the 3 sec time period, either the first UV-exposure-modes-witching routine (FIG. 42), the second UV-exposure-modes-witching routine (FIG. 43) or the third UV-exposure-modes-witching routine (FIG. 44) is executed (step 4104, 4108 or 4112).

Figure 42:
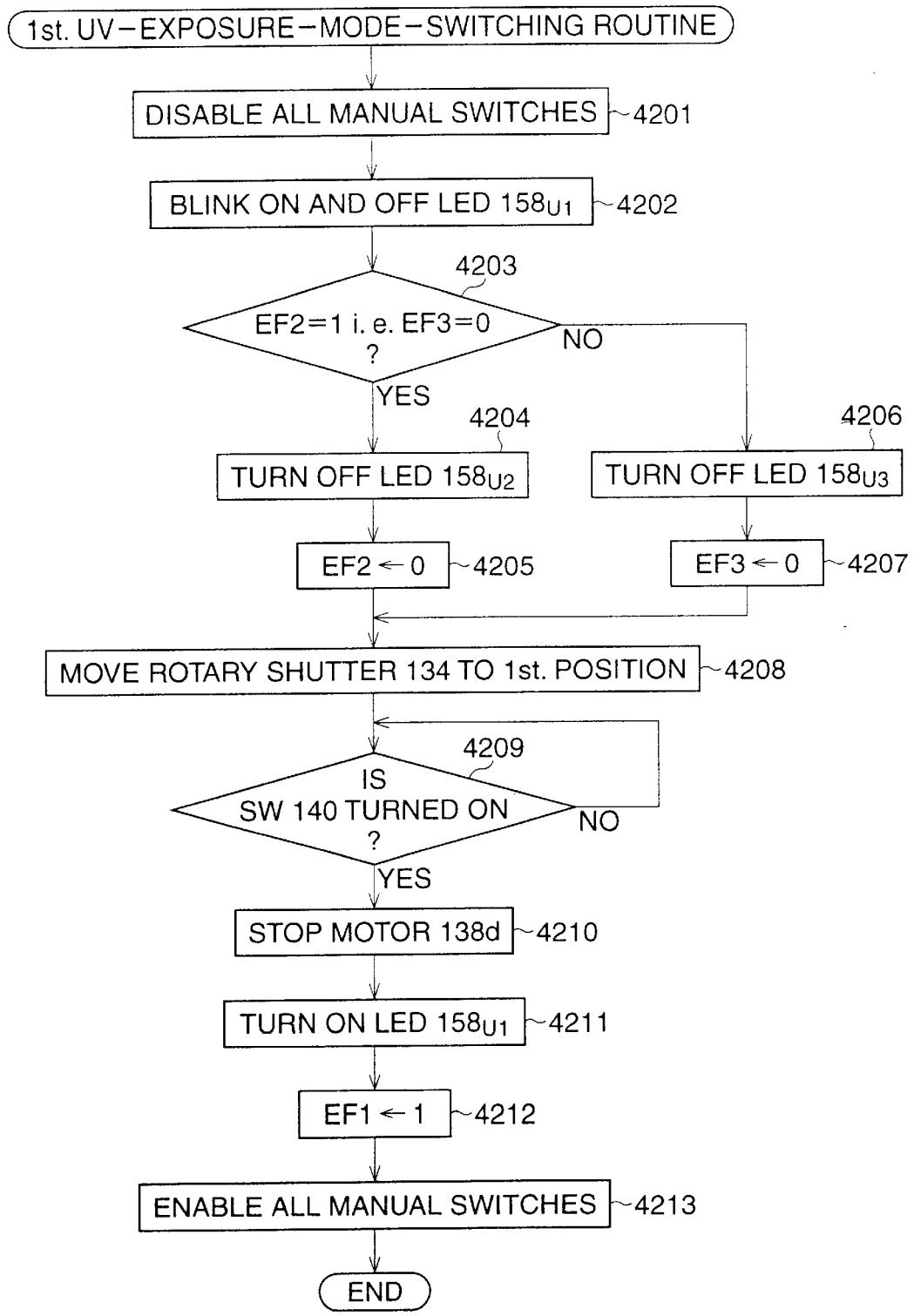
FIG. 42 is a flowchart of a first UV-exposure-mode-switching routine executed in the second embodiment.

FIG. 42 is a flowchart of the first UV-exposure-modes-witching routine, which is executed in the system controller 72 after being commanded at step 4104 of the UV-exposure-mode-selection-monitoring routine of FIG. 41.

At step 4201, all the manual switches (except for the power ON/OFF switch 152$_{PW}$), provided on the front panel 88', are disabled. Then, at step 4202, the LED 158$_{U1}$ is blinked ON and OFF, thereby indicating that the first UV-exposure mode is being selected.

At step 4203, it is determined whether the second UV-exposure-mode-indication flag EF2 is "1", i.e. whether the third UV-exposure-mode-indication flag EF3 is "0". If EF2=1, and EF3 =0 (i.e. the second UV-exposure mode is selected), the control proceeds to step 4204, in which the LED 158$_{U2}$ is turned OFF. Then, at step 4205, the flag EF2 is set to "0". On the other hand, If EF2=0 and EF3=1, (i.e. the third UV-exposure mode is selected), the control proceeds from step 4203 to step 4206, in which the LED 158$_{U3}$ is turned OFF. Then, at step 4207, the flag EF3 is set to 0".

In either case, at step 4208, the motor 138d is driven such that the rotary shutter 134 is moved toward the first operative position. Then, at step 4209, it is monitored at suitable regular intervals of, for example, 50 ms whether the limit switch 140 has been turned ON. When it is confirmed that the limit switch 140 is turned ON, the control proceeds to step 4210, in which the motor 138d is stopped, thereby positioning the rotary shutter 134 at the first operative position.

At step 4211, the blinked LED 158$_{U1}$ is continuously turned N, thereby visually indicating that the first UV-exposure mode has been selected. Then, at step 4212, the flag EF1 is set to "1", thereby indicating that the selection of the first UV-exposure mode is completed. Subsequently, at step 4213, all the manual switches are enabled, and thus the routine ends.

Figure 43:
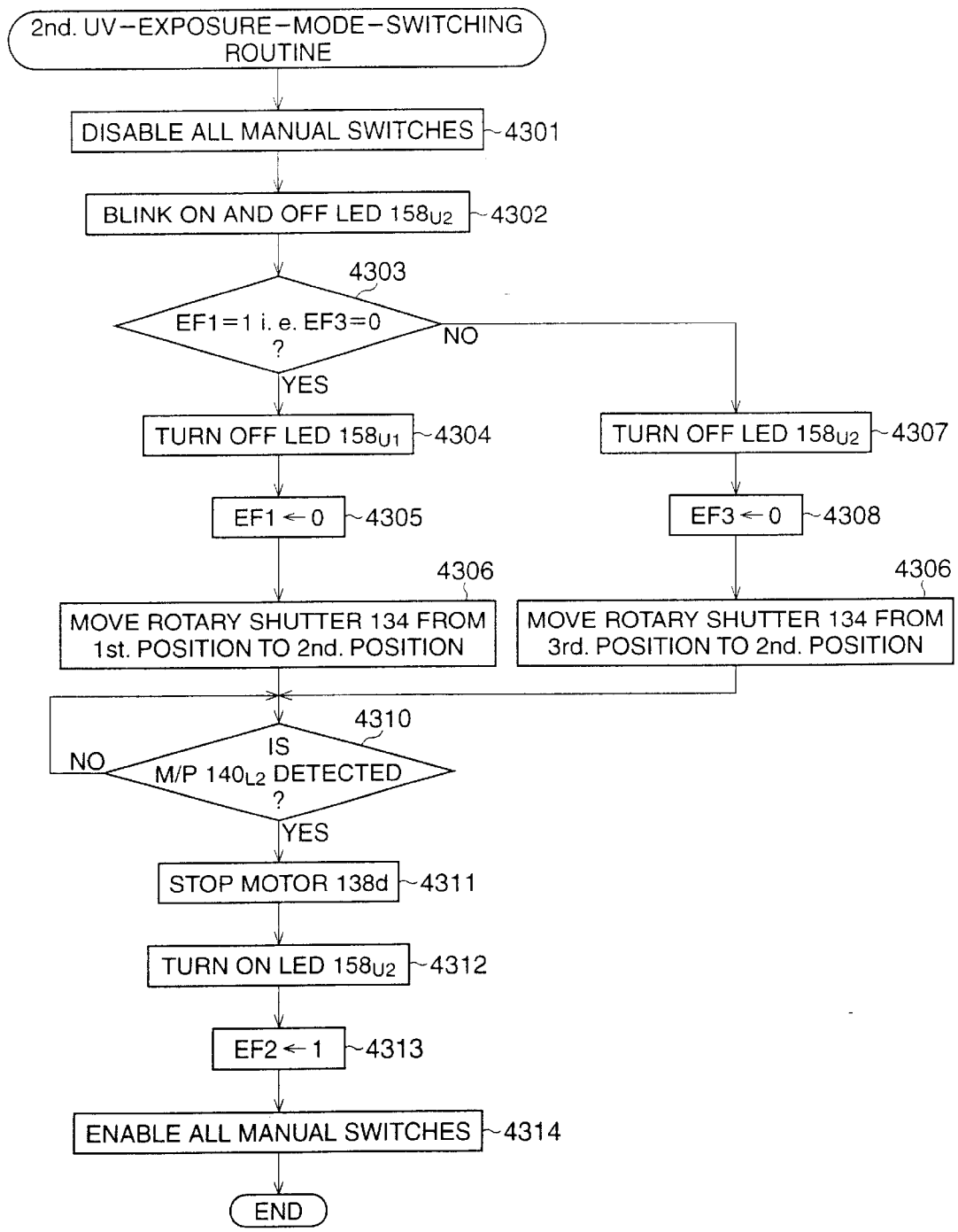
FIG. 43 is a flowchart of a second UV-exposure-mode-switching routine executed in the second embodiment.

FIG. 43 is a flowchart of the second UV-exposure-mode-switching routine, which is executed in the system controller 72 after being commanded at step 4108 of the UV-exposure-mode-selection-monitoring routine of FIG. 41.

At step 4301, all the manual switches (except for the power ON/OFF switch 152$_{PW}$), provided on the front panel 88', are disabled. Then, at step 4302, the LED 158$_{U2}$ is blinked ON and OFF, thereby indicating that the second UV-exposure mode is being selected.

At step 4303, it is determined whether the first UV-exposure-mode-indication flag EF1 is "1", i.e. whether the third UV-exposure-mode-indication flag EF3 is "0".

If EF1=1, and EF3=0 (i.e. the first UV-exposure mode is selected), the control proceeds from 4303 to step 4304, in which the LED 158$_{U1}$ is turned OFF. Then, at step 4305, the flag EF1 is set to "0". Subsequently, at step 4306, the motor 138d is driven such that the rotary shutter 134 is moved from the first operative position toward the second operative position.

On the other hand, If EF1=0 and EF3=1, (i.e. the third UV-exposure mode is selected), the control proceeds from step 4303 to step 4307, in which the LED 158$_{U3}$ is turned OFF. Then, at step 308, the flag EF3 is set to "0". Subsequently, at step 4309, the motor 138d is driven such that the rotary shutter 134 is moved from the third operative position toward the second operative position.

In either case, at step 4310, it is monitored at suitable regular intervals of, for example, 50 ms whether the detective magnet piece 146$_{L2}$ has been detected by the magnetic position detector 144. When the detection of the detective magnet piece 146$_{L2}$ by the magnetic position-detector 144 is confirmed, the control proceeds to step 4211, in which the motor 138d is stopped, thereby positioning the rotary shutter 134 at the second operative position.

At step 4312, the blinked LED 158$_{U2}$ is continuously turned ON, thereby visually indicating that the second UV-exposure mode has been selected. Then, at step 4313, the flag EF2 is set to "1", thereby indicating that the selection of the second UV-exposure mode is completed. Subsequently, at step 4314, all the manual switches are enabled, and thus the routine ends.

Figure 44:
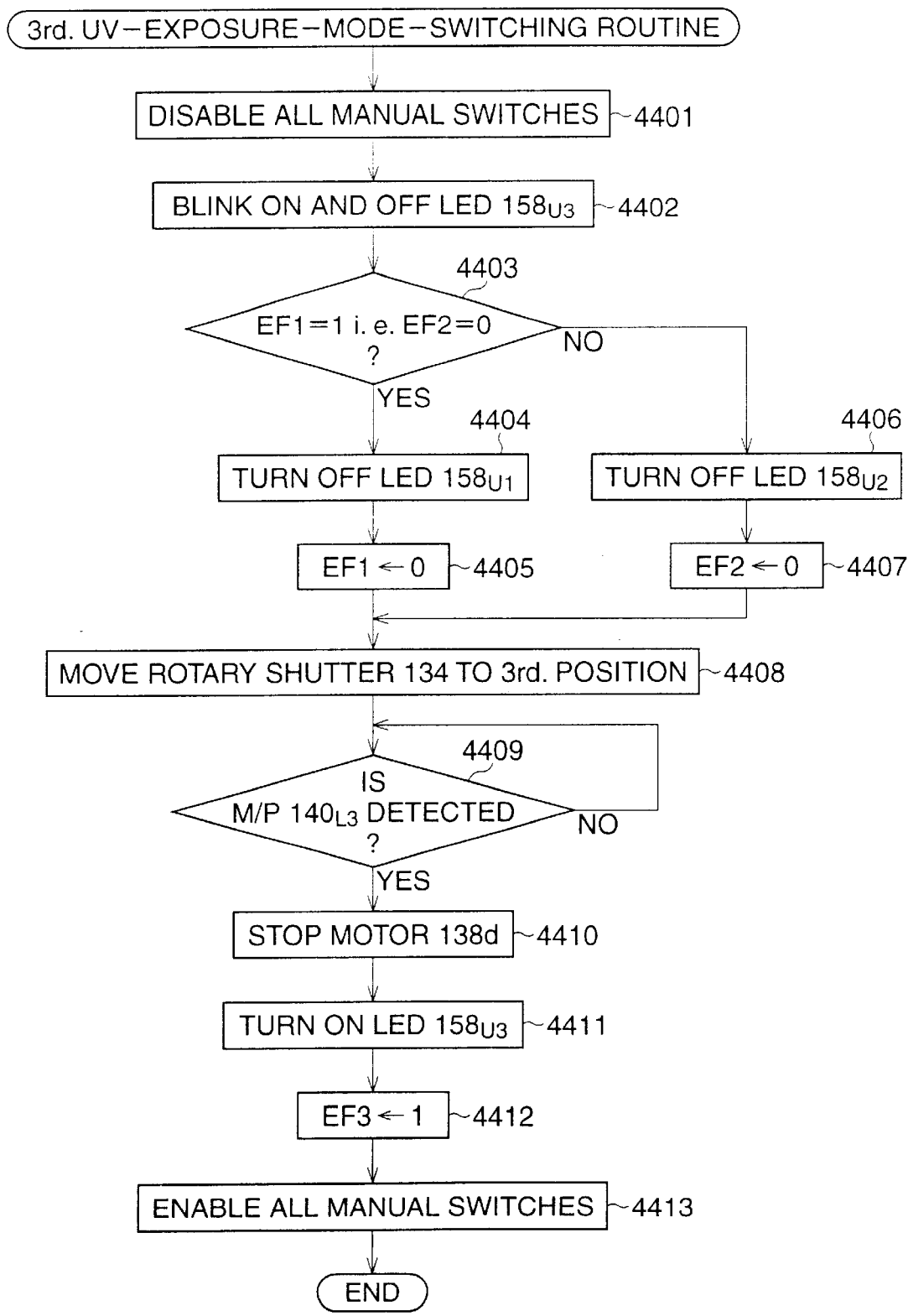
FIG. 44 is a flowchart of a third UV-exposure-mode-switching routine executed in the second embodiment.

FIG. 44 is a flowchart of the third UV-exposure-modes-witching routine, which is executed in the system controller 72 after being commanded at step 4112 of the UV-exposure-mode-selection-monitoring routine of FIG. 41.

At step 4401, all the manual switches (except for the power ON/OFF switch 152$_{PW}$), provided on the front panel 88', are disabled. Then, at step 4402, the LED 158$_{U3}$ is blinked ON and OFF, thereby indicating that the third UV-exposure mode is being selected.

At step 4403, it is determined whether the first UV-exposure-mode-indication flag EF1 is "1", i.e. whether the second UV-exposure-mode-indication flag EF2 is "0". If EF1=1, and EF2 =0 (i.e. the first UV-exposure mode is selected), the control proceeds to step 4404, in which the LED 158$_{U1}$ is turned OFF. Then, at step 4405, the flag EF1 is set to "0". On the other hand, If EF1=0 and EF2=1 (i.e. the second UV-exposure mode is selected), the control proceeds from step 4403 to step 4406, in which the LED 158$_{U2}$ is turned OFF. Then, at step 4407, the flag EF2 is set to In either case, at step 4408, the motor 138d is driven such that the rotary shutter 134 is moved toward the third operative position. Then, at step 4409, it is monitored at suitable regular intervals of, for example, 50 ms whether the detective magnet piece 146$_{L3}$ has been detected by the magnetic position-detector 144. When the detection of the detective magnet piece 146$_{L3}$ by the magnetic position-detector 144 is confirmed, the control proceeds to step 4410, in which the motor 138d is stopped, thereby positioning the rotary shutter 134 at the third operative position.

At step. 4411, the blinked LED 158$_{U3}$ is continuously turned ON, thereby visually indicating that the third UV-exposure mode has been selected. Then, at step 4412, the flag EF3 is set to "1", thereby indicating that the selection of the third UV-exposure mode is completed. Subsequently, at step 4413, all the manual switches are enabled, and thus the routine ends.

In the aforesaid embodiments, although the specific wavelength light source is represented by the ultra-violet lamp, another specific wavelength light source, such as an infrared lamp, may be used for medical treatment.

Finally, it will be understood by those skilled in the art that the foregoing description is of preferred embodiments of the system, and that various changes and modifications may be made to the present invention without departing from the spirit and scope thereof.

The present disclosure relates to subject matters contained in Japanese Patent Applications No. 2000-005674 (filed on Jan. 14, 2000) and No. 2000-242554 (filed on Aug. 10, 2000) which are expressly incorporated herein, by reference, in their entireties.

What is claimed is:

1. An electronic endoscope system comprising:
   a scope having an image sensor provided at a distal end thereof to generate image-pixel signals;
   an image-signal processing unit, to which a proximal end of said scope is connected, that processes the image-pixel signals to thereby produce a video signal;
   a light source device provided in said image-signal processing unit; and
   an optical light guide that extends through said scope, said optical light guide being optically connected to said light source device when the connection is established between said scope and said image-signal processing unit, wherein said light source device includes:
   a first light source that emits white light;
   a second light source that emits a specific wavelength light;
   a light source switcher that selectively introduces one of said white light and said specific wavelength light into said optical light guide along a light path;
   a rotary color-filter/shutter; and
   a filter/shutter driver that moves said color-filter/shutter in a direction substantially transverse to the light path between a first operative position and a second operative position.

2. An electronic endoscope system as set forth in claim 1, wherein said light source switcher includes:
   a light deflector; and
   a deflector driver that moves said light deflector between a first operative position and a second operative position, the white light, emitted from said first light source, being directly introduced into said optical light guide when said light deflector is positioned at said first operative position, the white light, emitted from said first light source, being blocked off by said light deflector and the specific wavelength light, emitted from said second light source, being introduced by said light deflector into said optical light guide when said light deflector is positioned at said second operative position.

3. An electronic endoscope system as set forth in claim 2, wherein said light source switcher further includes:
   an illumination mode selection system that selects one of a first illumination mode, in which said white light is introduced into said optical light guide, and a second illumination mode, in which said specific wavelength light is introduced into said optical light guide; and
   a controller that controls said deflector driver such that said light deflector is positioned at said first operative position when said first illumination mode is selected by said illumination mode selection system, and such that said light deflector is positioned at said second operative position when said second illumination mode is selected by said illumination mode selection system.

4. An electronic endoscope system as set forth in claim 1, wherein said color-filter/shutter functions as a rotary color filter when moved to said first operative position by said filter/shutter driver and said color-filter/shutter functions as a rotary shutter when moved to said second operative position by said filter/shutter driver, said white light being converted into three primary color lights through said color-filter/shutter, positioned at said first operative position, whereby said three primary color lights are cyclically and sequentially introduced into said optical light guide, said specific wavelength light being cyclically and sequentially introduced into said optical light guide through said color-filter/shutter positioned at said second operative position.

5. An electronic endoscope system as set forth in claim 4, wherein said light source device further includes:
   an illumination mode selection system that selects one of a first illumination mode, in which said white light is introduced into said optical light guide, and a second illumination mode, in which said specific wavelength light is introduced into said optical light guide; and
   a controller that controls said filter/shutter driver such that said color-filter/shutter is positioned at said first operative position when said first illumination mode is selected by said illumination mode selection system, and such that said color-filter/shutter is positioned at said second operative position when said second illumination mode is selected by said illumination mode selection system.

6. An electronic endoscope system as set forth in claim 4, wherein said rotary color-filter/shutter comprises a disk element having three primary color filters circumferentially spaced from each other at regular angular intervals, areas between adjacent color filters being formed as light-shielding areas, said light-shielding areas extending radially outwardly beyond said color filters such that the extended areas form said rotary shutter.

7. An electronic endoscope system as set forth in claim 4, wherein said rotary color-filter/shutter comprises a disk element having three primary color filters circumferentially spaced from each other at regular angular intervals, areas between adjacent color filters being formed as light-shielding areas, one of said light-shielding areas extending radially outwardly beyond said color filters such that the extended area forms said rotary shutter.

8. A rotary color-filter/shutter comprising: a disk element having three primary color filters circumferentially spaced from each other at regular angular intervals, areas between adjacent color filters being formed as light-shielding areas, at least one of said light-shielding areas extending radially outwardly beyond said color filters such that the extended area forms a rotary shutter.

9. An electronic endoscope system comprising:
   a scope having an image sensor provided at a distal end thereof to generate image-pixel signals;
   an image-signal processing unit, to which a proximal end of said scope is connected, that processes the image-pixel signals to thereby produce a video signal;
   a light source device provided in said image-signal processing unit; and
   an optical light guide that extends through said scope, said optical light guide being optically connected to said light source when the connection is established between said scope and said image-signal processing unit,
   wherein said light source device comprises:
   a first light source that emits white light;
   a second light source that emits a specific wavelength light;
   a light source switcher that selectively introduces one of said white light and said specific wavelength light into said optical light guide;
   a rotary shutter associated with said second light source such that said rotary shutter is interposed in a specific-wavelength-light path through which said specific wavelength light passes, said rotary shutter including at least two light-shielding elements circumferentially spaced from each other at regular angular intervals and having different radial lengths; and
   a shutter driver that relatively moves and positions said rotary shutter with respect to said specific-wavelength-light path such that said specific-wavelength-light path is selectively blocked off by said light-shielding elements having the different radial lengths, whereby an exposure time, during which said image sensor is illuminated with said specific wavelength light, is varied.

10. An electronic endoscope system as set forth in claim 9, wherein said light source device further comprises a rotary color filter interposed in a white-light path through which said white light passes, a rotational frequency of said color filter being an integral multiple of a rotational frequency of said rotary shutter.

11. An electronic endoscope system as set forth in claim 9, wherein said light source switcher includes:
   a light deflector; and
   a deflector driver that moves said light deflector between a first operative position and a second operative position, the white light, emitted from said first light source, being directly introduced into said optical light guide when said light deflector is positioned at said first operative position, the white light, emitted from said first light source, being blocked off by said light deflector and the specific wavelength light, emitted from said second light source, being introduced-by said light deflector into said optical light guide when said light deflector is positioned at said second operative position.

12. An electronic endoscope system as set forth in claim 11, wherein said light source switcher further includes:
   an illumination mode selection system that selects one of a first illumination mode, in which said white light is introduced into said optical light guide, and a second illumination mode, in which said specific wavelength light is introduced into said optical light guide; and
   a controller that controls said deflector driver such that said light deflector is positioned at said first operative position when said first illumination mode is selected by said illumination mode selection system, and such that said light deflector is positioned at said second operative position when said second illumination mode is selected by said illumination mode selection system.

13. An electronic endoscope system as set forth in claim 9, wherein said rotary shutter is moved by said shutter driver between first and second relative positions with respect to said specific-wavelength-light path, said specific-wavelength-light path being blocked off by a longer one of said light-shielding elements when said rotary shutter is positioned at said first relative position, said specificwavelength-light path being blocked off by both of said light-shielding elements when said rotary shutter is positioned at said second relative position.

14. An electronic endoscope system as set forth in claim 13, wherein said light source device further includes:

an exposure mode selection system that selects one of a first exposure mode, in which said specific-wavelength-light path is blocked off by the longer one of said light-shielding elements, and a second exposure mode, in which said specific-wavelength-light path is blocked off by both of said light-shielding elements; and a controller that controls said shutter driver such that said rotary shutter is positioned at said first relative position when said first exposure mode is selected by said exposure mode selection system, and such that said rotary shutter is positioned at said second relative position when said second exposure mode is selected by said exposure mode selection system.

* * * * *